United States Patent
Himmler et al.

(10) Patent No.: US 10,385,118 B2
(45) Date of Patent: Aug. 20, 2019

(54) SYNTHETIC IMMUNOGLOBULIN DOMAINS WITH BINDING PROPERTIES ENGINEERED IN REGIONS OF THE MOLECULE DIFFERENT FROM THE COMPLEMENTARITY DETERMINING REGIONS

(71) Applicant: F-star Biotechnologische Forschungs- und Entwicklungsges.m.b.H, Cambridge (GB)

(72) Inventors: Gottfried Himmler, Gross-Enzersdorf (AT); Florian Rüker, Vienna (AT); Gordana Wozniak-Knopp, Vienna (AT)

(73) Assignee: F-star Biotechnologische Forschungs- und Entwicklungsges.m.b.H, Vienna (AT)

(*) Notice: Subject to any disclaimer, the term of this patent is extended or adjusted under 35 U.S.C. 154(b) by 224 days.

(21) Appl. No.: 15/476,029

(22) Filed: Mar. 31, 2017

(65) Prior Publication Data
US 2017/0204164 A1    Jul. 20, 2017

Related U.S. Application Data

(63) Continuation of application No. 13/149,871, filed on May 31, 2011, now Pat. No. 9,856,311, which is a
(Continued)

(51) Int. Cl.
*C40B 40/10* (2006.01)
*C07K 16/00* (2006.01)
(Continued)

(52) U.S. Cl.
CPC .............. *C07K 16/00* (2013.01); *C07K 16/28* (2013.01); *C07K 16/40* (2013.01); *C07K 19/00* (2013.01);
(Continued)

(58) Field of Classification Search
None
See application file for complete search history.

(56) References Cited

U.S. PATENT DOCUMENTS

| 5,223,409 A | 6/1993 | Ladner et al. |
| 5,395,750 A | 3/1995 | Dillon et al. |

(Continued)

FOREIGN PATENT DOCUMENTS

| AU | 2005/289685 | 9/2005 |
| AU | 2006/204459 | 1/2006 |

(Continued)

OTHER PUBLICATIONS

Adachi M., et al., "Interaction between the antigen and antibody is controlled by the constant domains: Normal mode dynamics of the HEL-HyHEL-10 complex," *Protein Science*, vol., Issue No. 10, pp. 2125-2131 (Oct. 2003).

(Continued)

*Primary Examiner* — Christian C Boesen
(74) *Attorney, Agent, or Firm* — Nutter McClennen & Fish LLP

(57) ABSTRACT

Libraries of immunoglobulins which each have one or more amino acid modifications in at least one structural loop region of such immunoglobulins, where the modified loop region specifically binds to an epitope of an antigen to which an unmodified immunoglobulin does not significantly bind.

6 Claims, 20 Drawing Sheets

Figure 1A:
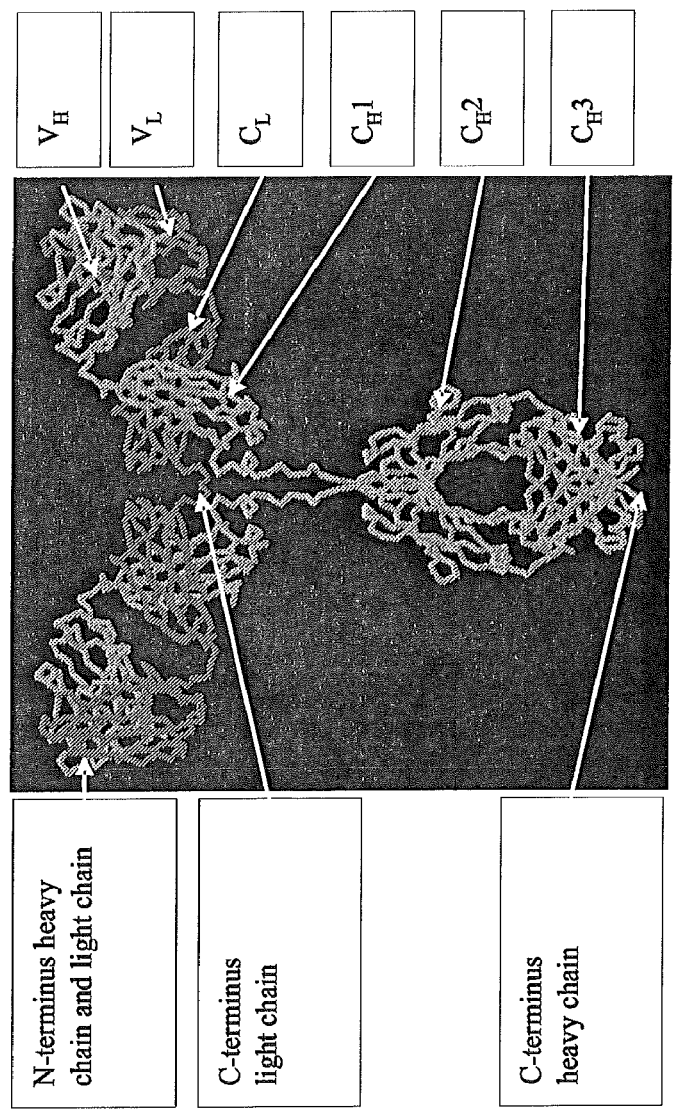

Specification includes a Sequence Listing.

Related U.S. Application Data continuation of application No. 11/722,517, filed as application No. PCT/EP2006/050059 on Jan. 5, 2006, now abandoned.

(60) Provisional application No. 60/641,144, filed on Jan. 5, 2005.

(51) Int. Cl.
  *C07K 19/00* (2006.01)
  *C07K 16/28* (2006.01)
  *C07K 16/40* (2006.01)

(52) U.S. Cl.
  CPC ...... *C07K 2317/21* (2013.01); *C07K 2317/31* (2013.01); *C07K 2317/52* (2013.01); *C07K 2317/522* (2013.01); *C07K 2317/526* (2013.01); *C07K 2317/55* (2013.01); *C07K 2318/20* (2013.01); *C07K 2319/30* (2013.01); *C40B 40/10* (2013.01)

(56) References Cited

U.S. PATENT DOCUMENTS

| | | |
|---|---|---|
| 5,475,100 A | 12/1995 | Hashino et al. |
| 5,536,814 A | 7/1996 | Ruoslahti et al. |
| 5,723,323 A | 3/1998 | Kauffman et al. |
| 5,759,817 A | 6/1998 | Barbas et al. |
| 5,763,192 A | 6/1998 | Kauffman et al. |
| 5,814,476 A | 9/1998 | Kauffman et al. |
| 5,817,483 A | 10/1998 | Kauffman et al. |
| 5,824,514 A | 10/1998 | Kauffman et al. |
| 5,844,094 A | 12/1998 | Hudson et al. |
| 5,892,019 A | 4/1999 | Schlom et al. |
| 6,057,098 A | 5/2000 | Buechler et al. |
| 6,180,104 B1 | 1/2001 | Davis et al. |
| 6,294,654 B1 | 9/2001 | Bogen et al. |
| 6,352,842 B1 | 3/2002 | Short et al. |
| 6,358,709 B1 | 3/2002 | Short et al. |
| 6,361,974 B1 | 3/2002 | Short et al. |
| 6,365,377 B1 | 4/2002 | Patten et al. |
| 6,376,246 B1 | 4/2002 | Crameri et al. |
| 6,562,617 B1 | 5/2003 | Anderson et al. |
| 6,602,684 B1 | 8/2003 | Umaña et al. |
| 7,442,778 B2 | 10/2008 | Gegg et al. |
| 7,632,497 B2 | 12/2009 | Stavenhagen |
| 7,645,861 B2 | 1/2010 | Gegg et al. |
| 7,655,764 B2 | 2/2010 | Gegg et al. |
| 7,655,765 B2 | 2/2010 | Gegg et al. |
| 7,662,931 B2 | 2/2010 | Gegg et al. |
| 7,750,127 B2 | 7/2010 | Gegg et al. |
| 7,750,128 B2 | 7/2010 | Gegg et al. |
| 7,858,090 B2 | 12/2010 | Koide |
| 8,008,453 B2 | 8/2011 | Gegg et al. |
| 8,580,927 B2 | 11/2013 | Dimitrov |
| 8,859,738 B2 | 10/2014 | Himmler et al. |
| 8,921,279 B2 | 12/2014 | Himmler et al. |
| 9,045,528 B2 | 6/2015 | Ruker et al. |
| 9,133,274 B2 | 9/2015 | Himmler et al. |
| 9,255,149 B2 | 2/2016 | Himmler et al. |
| 9,651,559 B2 | 5/2017 | Himmler et al. |
| 9,856,311 B2 | 1/2018 | Ruker et al. |
| 2002/0103345 A1 | 8/2002 | Zhu |
| 2002/0106370 A1 | 8/2002 | Cardy et al. |
| 2003/0027213 A1 | 2/2003 | Zhu et al. |
| 2003/0129188 A1 | 7/2003 | Barbas et al. |
| 2003/0148372 A1 | 8/2003 | Tomlinson et al. |
| 2003/0157091 A1 | 8/2003 | Hoogenboom |
| 2004/0018508 A1 | 1/2004 | Friedman |
| 2004/0043424 A1 | 3/2004 | Baughn et al. |
| 2004/0063924 A1 | 4/2004 | Tang et al. |
| 2004/0071690 A1 | 4/2004 | Hudson et al. |
| 2004/0082508 A1 | 4/2004 | Yue et al. |
| 2004/0097711 A1 | 5/2004 | Yue et al. |
| 2004/0101905 A1 | 5/2004 | Brekke et al. |
| 2004/0132101 A1 | 7/2004 | Lazar et al. |
| 2004/0146976 A1 | 7/2004 | Wittrup et al. |
| 2005/0009025 A1 | 1/2005 | Jakobsen et al. |
| 2005/0054832 A1 | 3/2005 | Lazar et al. |
| 2005/0069549 A1 | 3/2005 | Herman |
| 2005/0158829 A1 | 7/2005 | Fandl et al. |
| 2005/0244403 A1 | 11/2005 | Lazar et al. |
| 2005/0255548 A1 | 11/2005 | Lipovsek et al. |
| 2005/0266000 A1 | 12/2005 | Bond et al. |
| 2006/0140934 A1 | 6/2006 | Gegg et al. |
| 2008/0227958 A1 | 9/2008 | Thompson et al. |
| 2009/0298195 A1 | 12/2009 | Ruker et al. |
| 2010/0009863 A1 | 1/2010 | Himmler et al. |
| 2010/0048877 A1 | 2/2010 | Ruker et al. |
| 2011/0046355 A1 | 2/2011 | Himmler et al. |
| 2011/0251375 A1 | 10/2011 | Rüker et al. |
| 2012/0010388 A1 | 1/2012 | Himmler |
| 2012/0028839 A1 | 2/2012 | Rüker et al. |
| 2012/0094874 A1 | 4/2012 | Rüker et al. |
| 2012/0276104 A1 | 11/2012 | Woisetschlager |
| 2013/0040836 A1 | 2/2013 | Himmler et al. |
| 2014/0087957 A1 | 3/2014 | Vuskovic et al. |
| 2014/0364592 A1 | 12/2014 | Himmler et al. |
| 2015/0153359 A1 | 6/2015 | Himmler et al. |
| 2015/0376603 A1 | 12/2015 | Himmler et al. |
| 2016/0176984 A1 | 6/2016 | Himmler et al. |
| 2016/0289336 A1 | 10/2016 | Leung et al. |
| 2017/0015727 A1 | 1/2017 | Himmler et al. |
| 2017/0204164 A1 | 7/2017 | Himmler et al. |
| 2017/0247432 A1 | 8/2017 | Himmler et al. |
| 2017/0369868 A1 | 12/2017 | Himmler et al. |
| 2018/0051095 A1 | 2/2018 | Ruker et al. |

FOREIGN PATENT DOCUMENTS

| | | |
|---|---|---|
| CN | 1606566 | 4/2005 |
| EP | 1 752 471 | 2/2007 |
| EP | 1 772 465 | 4/2007 |
| EP | 2 028 193 | 2/2009 |
| EP | 1 699 826 | 3/2009 |
| EP | 2 407 487 | 1/2012 |
| JP | 2002-058479 | 2/2002 |
| JP | 2003-518377 | 6/2003 |
| JP | 2008-526809 A | 7/2008 |
| JP | 2010-531144 A | 9/2010 |
| JP | 2015-028078 | 2/2015 |
| WO | WO 90/07861 | 7/1990 |
| WO | WO 92/09690 | 6/1992 |
| WO | WO 93/08278 | 4/1993 |
| WO | WO 93/23537 | 11/1993 |
| WO | WO 96/22377 | 7/1996 |
| WO | WO 97/20858 | 6/1997 |
| WO | WO 97/34631 | 9/1997 |
| WO | WO 98/39482 | 9/1998 |
| WO | WO 00/42561 | 7/2000 |
| WO | WO 00/44788 | 8/2000 |
| WO | WO 00/71694 | 11/2000 |
| WO | WO 01/01748 | 1/2001 |
| WO | WO 01/48145 | 7/2001 |
| WO | WO 01/55366 | 8/2001 |
| WO | WO 01/57211 | 8/2001 |
| WO | WO 01/62908 | 8/2001 |
| WO | WO 01/70947 | 9/2001 |
| WO | WO 01/83525 | 11/2001 |
| WO | WO 01/88159 | 11/2001 |
| WO | WO 02/06469 | 1/2002 |
| WO | WO 02/32925 | 4/2002 |
| WO | WO 02/44215 | 6/2002 |
| WO | WO 02/059263 | 8/2002 |
| WO | WO 02/060919 | 8/2002 |
| WO | WO 02/066636 | 8/2002 |
| WO | WO 02/088171 | 11/2002 |
| WO | WO 03/012100 | 2/2003 |
| WO | WO 03/029456 | 4/2003 |
| WO | WO 2003/075840 | 9/2003 |
| WO | WO 2004/018674 | 3/2004 |
| WO | WO 2004/033685 | 4/2004 |
| WO | WO 2004/041862 | 5/2004 |
| WO | WO 2004/044004 | 5/2004 |

(56) References Cited

FOREIGN PATENT DOCUMENTS

| WO | WO 2004/044011 | 5/2004 |
|---|---|---|
| WO | WO 2004/050705 | 6/2004 |
| WO | WO 2004/074322 | 9/2004 |
| WO | WO 2005/021595 | 3/2005 |
| WO | WO 2005/113595 | 12/2005 |
| WO | WO 2005/114215 | 12/2005 |
| WO | WO 2005/116646 | 12/2005 |
| WO | WO 2006/033700 | 3/2006 |
| WO | WO 2006/036834 | 4/2006 |
| WO | WO 2006/037960 | 4/2006 |
| WO | WO 2006/054096 | 5/2006 |
| WO | WO 2006/056733 | 6/2006 |
| WO | WO 2006/072620 | 7/2006 |
| WO | WO 2006/087637 | 8/2006 |
| WO | WO 2008/003103 | 1/2008 |
| WO | WO 2008/003116 | 1/2008 |
| WO | WO 2008/119096 | 10/2008 |
| WO | WO 2009/000006 | 12/2008 |
| WO | WO 2009/099961 | 8/2009 |
| WO | WO 2009/132876 | 11/2009 |
| WO | WO 2011/003811 | 1/2011 |
| WO | WO 2012/007167 | 1/2012 |
| WO | WO 2015/049537 | 4/2015 |
| WO | WO 2016/162505 A1 | 10/2016 |

OTHER PUBLICATIONS

Adib-Conquy M. et al., "Effect of amino acid substitutions in the heavy chain CDR3 of an autoantibody on its reactivity," *International Immunology*, vol. 10, Issue No. 3, pp. 341-346 (Mar. 1998).
Altschul S.F., et al, "Local Alignment Statistics," *Methods in Enzymology*, vol. 266, pp. 460-480 (1996).
Amstutz P., et al., "In vitro display technologies: novel developments and applications," *Current Opinion Biotechnology*, vol. 12, Issue No. 4, pp. 400-405 (Aug. 2001).
Asano R., et al., "Humanization of the Bispecific Epidermal Growth Factor Receptor×CD3 Diabody and Its Efficacy as a Potential Clinical Reagent," *Clinical Cancer Research*, vol. 12, No. 13, pp. 4036-4042 (2006).
Auf der Maur A., et al., "Antigen-independent selection of intracellular stable antibody frameworks," *Methods*, vol. 34, No. 2, pp. 215-224 (Oct. 2004).
Barbas II., C.F. et al., "Semisynthetic combinatorial antibody libraries: a chemical solution to the diversity problem," *Proceedings of the National Academy of Sciences of the USA*, vol. 89, No. 10, pp. 4457-4461 (May 15, 1992).
Barclay A.N., "Membrane proteins with immunoglobulin-like domains—a master superfamily of interaction molecules," *Seminars in Immunology*, vol. 15, No. 4, pp. 215-223 (Aug. 2003).
Batey S., et al., "Abstract B123: Preclinical evaluation of FS102: A HER2-specific Fcab with a novel mechanism of action," *Molecular Cancer Therapeutics*, vol. 12, 1 page (Nov. 12, 2013) (Abstract).
Batey S., et al., Poster: "Preclinical evaluation of FS102: A HER2-specific Fcab with a novel mechanism of action," AACR-NCI-EORTC International Conference on Molecular Targets and Cancer Therapeutics, Boston, 1 page (Oct. 21, 2013).
Benhar I., et al., "Highly Efficient Selection of Phage Antibodies Mediated by Display of Antigen as Lpp-OmpA' Fusions on Live Bacteria," *Journal of Molecular Biology*, vol. 301, Issue No. 4, pp. 893-904 (Aug. 2000).
Berntzen G., et al., "Characterization of an FcγRI-binding peptide selected by phage display," *Protein Engineering, Design & Selection*, vol. 19, Issue No. 3, pp. 121-128 (Jan. 2006).
Berntzen G., et al., "Prolonged and increased expression of soluble Fc receptors, IgG and a TCR-Ig fusion protein by transiently transfected adherent 293E cells," *Journal Immunological Methods*, vol. 298, Issue Nos. 1-2, pp. 93-104 (Mar. 200).
Berry J.D., et al., "Development of Functional Human Monoclonal Single-Chain Variable Fragment Antibody Against HIV-1 from Human Cervical B Cells," *Hybridoma and Hybridomaics*, vol. 22, Issue No. 2, pp. 97-108 (Apr. 2003).
Binz H.K., et al., "High-affinity binders selected from designed ankyrin repeat protein libraries," *Nature Biotechnology*, vol. 22, Issue No. 5, pp. 575-582 (May 2004).
Binz H.K., et al., "Engineering novel binding proteins from nonimmunoglobulin domains," *Nature Biotechnology*, vol. 23, Issue No. 10, pp. 1257-1268 (Oct. 2005).
Bird R.E., et al., "Single-Chain Antigen-Binding Proteins," *Science*, vol. 242, Issue No. 4877, pp. 423-426 (Oct. 1988).
Boder E.T., et al., "Yeast surface display for screening combinatorial polypeptide libraries," *Nature Biotechnology*, vol. 15, Issue No. 6, pp. 553-557 (Jun. 1997).
Boder E.T., et al., "Yeast Surface Display for Directed Evolution of Protein Expression, Affinity, and Stability," *Methods in Enzymology*, vol. 328, pp. 430-444 (2000).
Boder E.T., et al., "Directed evolution of antibody fragments with monovalent femtomolar antigen-binding affinity," *Proceedings of the National Academy of Sciences of the USA*, vol. 97, Issue No. 20, pp. 10701-10705 (Sep. 2000).
Bork P., et al., "The Immunoglobulin Fold. Structural Classification, Sequence Patterns and Common Core," *Journal of Molecular Biology*, vol. 242, pp. 309-320 (1994).
Boulter J.M., et al., "Stable, soluble, high-affinity, engineered T cell receptors: novel antibody-like proteins for specific targeting of Peptide antigens," *Clinical and Experimental Immunology*, pp. 454-460 (2005).
Bowie J.U., et al., "Deciphering the Message in Protein Sequences: Tolerance to Amino Acid Substitutions," *Science*, vol. 247, Issue No. 4948, pp. 1306-1310 (Mar. 1990).
Braren I., et al., "Comparative expression of different antibody formats in mammalian cells and *Pichia pastoris*," *Biotechnology and Applied Biochemistry*, vol. 47, Part 4, pp. 205-214 (Aug. 2007).
Brawley J.V., et al., "Complementarity-Determining Region 1 Sequence Requirements Drive Limited Vα Usage in Response to Influenza Hemagglutinin 307-319 Peptide" *The Journal of Immunology*, vol. 168, Issue No. 8, pp. 3894-3901 (Apr. 2002).
Brekke O.H., et al., "Therapeutic Antibodies for Human Diseases at the Dawn of the Twenty-First Century," *Nature Reviews Drug Discovery*, vol. 2, Issue No. 1, pp. 52-62 (Jan. 2003).
Bunn P.A., Jr., et al., "Expression of Her-2/neu in Human Lung Cancer Cell Lines by Immunohistochemistry and Fluorescence in Situ Hybridization and its Relationship to in Vitro Cytotoxicity by Trastuzumab and Chemotherapeutic Agents," *Clinical Cancer Research*, vol. 7, pp. 3239-3250 (Oct. 2001).
Burgess W.H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *Journal of Cell Biology*, vol. 111, pp. 2129-2138 (Nov. 1990).
Cabilly S., et al., "Generation of antibody activity from immunoglobulin polypeptide chains produced in *Escherichia coli*," *Proceedings of National Academy of Sciences of the USA*, vol. 81, pp. 3273-3277 (Jun. 1984).
Caldas C., et al., "Humanization of the anti-CD18 antibody 6.7: an unexpected effect of a framework residue in binding to antigen," *Molecular Immunology*, vol. 39, Issue No. 15, pp. 941-952 (May 2003).
Calman A.F., et al., "Expression of T Cell Receptor Genes in Human B Cells", *The Journal of Experimental Medicine*, vol. 164, Issue No. 6, pp. 1940-1957 (Dec. 1986).
Carter P., "Bispecific human IgG by design," *Journal of Immunological Methods*, vol. 248, pp. 7-15 (Feb. 2001).
Carter P., et al., "High Level *Escherichia coli* Expression and Production of a Bivalent Humanized Antibody Fragment," *Biotechnology*, vol. 10, Issue No. 2, pp. 163-167 (Feb. 1992).
Chen G., et al., "Isolation of high-affinity ligand-binding proteins by periplasmic expression with cytometric screen (PECS)," *Nature Biotechnology*, vol. 19, pp. 537-542 (Jun. 2001).
Chien N.C., et al., "Significant structural and functional change of an antigen-binding site by a distant amino acid substitution: Pro-

(56) References Cited

OTHER PUBLICATIONS posal of a structural mechanism," *Proceeding of the National Academy of Sciences of the USA*, vol. 86, Issue No. 14, pp. 5532-5536 (Jul. 1989).
Chirino A.J., et al., "Minimizing the immunogenicity of protein therapeutics," *Drug Discovery Today*, vol. 9, Issue No. 2, pp. 82-90 (Jan. 2004).
Chlewicki L.K., et al., "High-affinity, Peptide-specific T Cell Receptors can be Generated by Mutations in CDR1, CDR2 or CDR3," *Journal of Molecular Biology*, vol. 346, Issue No. 1, pp. 223-239 (Feb. 2005).
Cho H.S., et al., "Structure of the extracellular region of HER2 alone and in complex with the Herceptin Fab," *Nature*, vol. 421, pp. 756-760 (Feb. 2003).
Coco W.M., et al., "DNA shuffling method for generating highly recombined genes and evolved enzymes," *Nature Biotechology*, vol. 19, pp. 354-359 (Apr. 2001).
Conrath K., et al., "Antigen Binding and Solubility Effects upon the Veneering of a Camel VHH in Framework-2 to Mimic a VH", *Journal of Molecular Biology*, vol. 350, pp. 112-125 (2005).
Cornish-Bowden A., "Nomenclature for incompletely specified bases in nucleic acid sequences: recommendations 1984," *Nucleic Acids Research*, vol. 3, Issue No. 9, pp. 3021-3030 (May 10, 1985).
Cortez-Retamozo V., et al., "Efficient Tumor Targeting by Single-Domain Antibody Fragments of Camels", International *Journal of Cancer*, vol. 98, pp. 456-462 (2002).
Crameri A., et al., "DNA shuffling of a family of genes from diverse species accelerates directed evolution," *Nature*, vol. 391, pp. 288-291 (Jan. 1998).
Dall'Acqua W.F., et al., "Modulation of the Effector Functions of a Human IgG1 through Engineering of Its Hinge Region," *The Journal of Immunology*, vol. 177, pp. 1129-1138 (2006).
Dall'Acqua W.F., et al., "Increasing the Affinity of a Human IgG1 for the Neonatal Fc Receptor: Biological Consequences," *The Journal of Immunology*, vol. 169, pp. 5171-5180 (2002).
De Jager et al., "Simultaneous Detection of 15 Human Cytokines in a Single Sample of Stimulated Peripheral Blood Mononuclear Cells, " *Clinical Diagnostic Laboratory Immunology*, vol. 10, Issue No. 1, pp. 133-139 (2003).
DiGiusto D.L., "An Analysis of Sequence Variation in the β Chain Framework and Complementarity Determining Regions of an Allo-Reactive T Cell Receptor," *Molecular Immunology*, vol. 31, Issue No. 9, pp. 693-699 (Jan. 1994).
Doi N., et al., "Screening of conformationally constrained random polypeptide libraries displayed on a protein scaffold," *Cellular and Molecular Life Sciences*, vol. 54, Issue No. 5, pp. 394-404 (May 1998).
Dottorini T., et al., "Crystal Structure of a Human VH: Requirements for Maintaining a Monomeric Fragment," *Biochemistry*, vol. 43, Issue No. 3, pp. 622-628 (Jan. 2004).
Dunn S.M., et al., "Directed evolution of human T cell receptor CDR2 residues by phage display dramatically enhances affinity for cognate peptide-MHC without increasing apparent cross-reactivity," *Protein Science*, vol. 15, pp. 710-721 (2006).
Esteva F.J., et al., "Molecular predictors of response to trastuzumab and lapatinib in breast cancer," *Nature Reviews Clinical Oncology*, vol. 7, Issue No. 2, pp. 98-107 (Feb. 2010).
Ewert S., et al., "Stability improvement of antibodies for extracellular and intracellular applications: CDR grafting to stable frameworks and structure-based framework engineering," *Methods*, vol. 34, pp. 184-199 (2004).
F-star, "F-star Alpha: A new asset centric company," 15 pages (Feb. 11, 2014).
Felgenhauer M., et al., "Nucleotide sequences of the cDNAs encoding the V-regions of H- and L-chains of a human monoclonal antibody specific to HIV-1—gp41," *Nucleic Acids Research*, vol. 18, Issue No. 16, p. 4927 (1990).
Fellouse F.A., et al., "Synthetic antibodies from a four-amino-acid code: A dominant role for tyrosine in antigen recognition," *Proceeding of the National Academy of Sciences of the USA*, vol. 101, Issue No. 34, pp. 12467-12472 (Aug. 2004).
Fellouse F.A., et al., "Molecular Recognition by a Binary Code," *The Journal of Molecular Biology*, vol. 348, Issue No. 5, pp. 1153-1162 (May 2005).
Fellouse F.A., et al., "Tyrosine Plays a Dominant Functional Role in the Paratope of a Synthetic Antibody Derived from a Four Amino Acid Code," *The Journal of Molecular Biology*, vol. 357, pp. 100-114 (2006).
Fields S., et al., "A novel genetic system to detect protein-protein interactions," *Nature*, vol. 340, pp. 245-246 (Jul. 1989).
Fitzgerald K., "In vitro display technologies—new tools for drug discovery," *Drug Discovery Today*, vol. 5, Issue No. 6, pp. 253-258 (Jun. 2000).
Foote J., et al., "Antibody Framework Residues Affecting the Conformation of the Hypervariable Loops," *Journal of Molecular Biology*, vol. 224, Issue No. 2, pp. 487-499 (Mar. 1992).
Fountzilas G., et al., "A randomized phase III study comparing three anthracycline-free taxane-based regimens, as first line chemotherapy, in metastatic breast cancer," *Breast Cancer Research and Treatment*, vol. 115, pp. 87-99 (2009).
Gao C., et al., "Making artificial antibodies: A format for phage display of combinatorial heterodimeric arrays," *Proceedings of the National Academy of Sciences of the USA*, vol. 96, Issue No. 11 pp. 6025-6030 (May 1999).
Georgiou G., et al., "Practical applications of engineering Gram-negative bacterial cell surfaces," *Trends in Biotechnology*, vol. 11, Issue No. 1, pp. 6-10 (Jan. 1993).
Georgiou G., et al., "Display of heterologous proteins on the surface of microorganisms: From the screening of combinatorial libraries to live recombinant vaccines," *Nature Biotechnology*, vol. 15, Issue No. 1, pp. 29-34 (Jan. 1997).
Ghahroudi Arabi M., et al., "Selection and identification of single domain antibody fragments from camel heavy-chain antibodies," *FEBS Letters*, vol. 414, Issue No. 3, pp. 521-526 (Sep. 1997).
Giusti A.M., et al., "Somatic diversification of S107 from an antiphosphocholine to an anti-DNA autoantibody is due to a single base change in its heavy chain variable region," *Proceedings of the National Academy of Sciences of the USA*, vol. 84, Issue No. 9, pp. 2926-2930 (May 1987).
Gonçalves M.S.T., "Fluorescent Labeling of Biomolecules with Organic Probes," *Chemical Review*, vol. 109, Issue No. 1, pp. 190-212 (2009).
Gram H., et al., "In vitro selection and affinity maturation of antibodies from a naïve combinatorial immunoglobulin library," *Proceedings of the National Academy of Sciences of the USA*, vol. 89, Issue No. 8, pp. 3576-3580 (Apr. 1992).
Halaby D.M., et al., "The immunoglobulin fold family: sequence analysis and 3D structure comparisons," *Protein Engineering*, vol. 12, Issue No. 7, pp. 563-571 (Jul. 1999).
Hanes J., et al., "In vitro selection and evolution of functional proteins by using ribosome display," *Proceedings of the National Academy of Sciences of the USA*, vol. 94, Issue No. 19, pp. 4937-4942 (May 1997).
Harriman W.D, et al., "Multiplexed Elispot Assay," *Journal Immunology Methods*, vol. 341, Issue No. 1-2, pp. 127-134 (Feb. 2009).
Hasenhindl C., et al., "Stability assessment on a library scale: a rapid method for the evaluation of the commutability and insertion of residues in C-terminal loops of the CH3 domains of IgG1-Fc," *Protein Engineering, Design and Selection*, vol. 26, Issue No. 10, pp. 675-682 (Oct. 2013).
Hasenhindl C., et al., "Creating stable stem regions for loop elongation in Fcabs—Insights from combining yeast surface display, in silico loop reconstruction and molecular dynamics simulations", *Biochimica et Biophysica Acta*, vol. 1844, Issue No. 9, pp. 1530-1540 (Sep. 2014).
Haurum J., Poster: "How to Leverage Oncogene Addiction: Targeted Biological Therapy Inducing Growth Factor Receptor Internalization and Degradation," Pipeline 2: Antibody Therapeutics, Inaugural Cancer Targets for Antibody Therapeutics. Discovery, Engineering and Optimization of Next-Generation Oncology Targets, 1 page (Jan. 19-20, 2015).

(56) References Cited

OTHER PUBLICATIONS

Hayhurst A., et al., "High-throughput antibody isolation," *Current Opinion in Chemical Biology*, vol. 5, Issue No. 6, pp. 683-689 (Dec. 2001).
He X.M., et al., "Structure of a human monoclonal antibody Fab fragment against gp41 of human immunodeficiency virus type 1," *Proceedings of the National Academy of Science of the USA*, vol. 89, Issue No. 15, pp. 7154-7158 (Aug. 1992).
Hermeling S., et al., "Structure-Immunogenicity Relationships of Therapeutic Proteins," *Pharmaceutical Research*, vol. 21, Issue No. 6, pp. 897-903 (Jun. 2004).
Holler P.D., et al., "In vitro evolution of a T cell receptor with high affinity for peptide/MHC," *Proceedings of the National Academy of Sciences of the USA*, vol. 97, Issue No. 10, pp. 5387-5392 (May 2000).
Holliger P., et al., "Engineered antibody fragments and the rise of single domains," *Nature Biotechnology*, vol. 23, Issue No. 9, pp. 1126-1136 (Sep. 2005).
Hoogenboom H.R., et al., "Multi-subunit proteins on the surface of filamentous phage: methodologies for displaying antibody (Fab) heavy and light chains," *Nucleic Acids Research*, vol. 19, Issue No. 15, pp. 4133-4137 (Aug. 1991).
Hoogenboom H.R., "Selecting and screening recombinant antibody libraries," *Nature in Biotechnology*, vol. 23, Issue No. 9, pp. 1105-1116 (Sep. 2005).
Hoover D.M., et al., "DNAWorks: an automated method for designing oligonucleotides for PCR-based gene synthesis," *Nucleic Acids Research*, vol. 30, Issue No. 10 (May 2002).
Hosse R.J., et al., "A new generation of protein display scaffolds for molecular recognition," *Protein Science*, vol. 15, Issue No. 1, pp. 14-27 (Jan. 2006).
Hufton S.E., et al., "Development and application of cytotoxic T lymphocyte-associated antigen 4 as a protein scaffold for the generation of novel binding ligand," *FEBS Letters*, vol. 465, Issue No. 3, pp. 225-231 (Jun. 2000).
Huston J. S., et al., "Protein engineering of antibody binding sites: Recovery of specific activity in an anti-digoxin single-chain Fv analogue produced in *Escherichia coli,*" *Proceedings of the National Academy of Sciences of the USA*, vol. 85, Issue No. 16, pp. 5879-5883 (Aug. 1988).
Isaac S., et al., Poster: "Pre-clinical evaluation of FS102: A HER2-specific Fcab with a novel mechanism of action," *AstraZeneca-MedImmune-Cambridge Cancer Centre Symposium*, 1 page (Mar. 25, 2014).
Iyengar N.M., et al., "A Pilot Study of Dose-Dense Paclitaxel With Trastuzumab and Lapatinib for Node-negative HER2-Overexpressed Breast Cancer," *Clinical Breast Cancer*, vol. 16, Issue No. 2, pp. 87-94 (Apr. 2016).
Janeway, Jr., C.A., et al., "The domains of an immunoglobulin molecule having similar structures," *Immunobiology, the Immune System in Health and Disease*, 6th edition, 3 pages (2005).
Jez J., et al., "Significant Impact of Single N-Glycan Residues on the Biological Activity of Fc-Based Antibody-Like Fragments," *The Journal of Biological Chemistry*, vol. 287, Issue No. 29, pp. 24313-24319 (Jul. 2012).
Johnsson N., et al., "Split ubiquitin as a sensor of protein interactions in vivo," *Proceedings of the National Academy of Sciences of the USA*, vol. 91, Issue No. 22, pp. 10340-10344 (Oct. 1994).
Jones P.T., et al., "Replacing the complementarity-determining regions in a human antibody with those from a mouse," *Nature*, vol. 321, Issue No. 6069, pp. 522-525 (May 1986).
Jung H.C., et al., "Surface display of *Zymomonas mobilis* levansucrase by using the ice-nucleation protein of *Pseudomonas syringae,*" *Nature Biotechnology*, vol. 16, Issue No. 6, pp. 576-580 (Jun. 1998).
Kainer M., et al., "Correlation between CD16a binding and immuno effector functionality of an antigen specific immunoglobulin Fc fragment (Fcab)," *Archives of Biochemistry and Biophysics*, vol. 526, Issue No. 2, pp. 154-158 (Oct. 2012).
Kang A.S., et al., "Linkage of recognition and replication functions by assembling combinatorial antibody Fab libraries along phage surfaces," *Proceedings of the National Academy of Sciences of the USA*, vol. 88, Issue No. 10, pp. 4363-4366 (May 1991).
Kang X., et al., "Human Neutralizing Fab Molecules against Severe Acute Respiratory Syndrome Coronavirus Generated by Phage Display," *Clinical and Vaccine Immunology*, vol. 13, Issue No. 8, pp. 953-957 (Aug. 2006).
Kashmiri S.V.S., et al., "SDR grafting—a new approach to antibody humanization," *Methods*, vol. 36, Issue No. 1, pp. 25-34 (May 2005).
Kay B.K., et al. (Edtrs.), "Phage Display of Peptides and Proteins: A Laboratory Manual," 10 pages, 1996.
Kettleborough C.A., et al., "Humanization of a mouse monoclonal antibody by CDR-grafting: the importance of framework residues on loop conformation," *Protein Engineering*, vol. 4, Issue No. 7, pp. 773-783 (Oct. 1991).
Kieke M.C., et al., "Selection of functional T cell receptor mutants from a yeast surface-display library," *Proceedings of the National Academy of Sciences of the USA*, vol. 96, Issue No. 10, pp. 5651-5656 (May 1999).
Kikuchi M., et al., "Novel family shuffling methods for the in vitro evolution of enzymes," *Gene*, vol. 236, Issue No. 1, pp. 159-167 (Aug. 1999).
Kikuchi M., et al., "An effective family shuffling method using single-stranded DNA," *Gene*, vol. 243, Issue No. 1-2, pp. 133-137 (Feb. 2000).
Kohl J., et al., "Cloning and Expression of an HIV-1 Specific Single-Chain Fv Region Fused to *Escherichia coli* Alkaline Phosphatase," *Annals of the New York Academy of Sciences*, vol. 646, pp. 106-114 (Dec. 1991).
Koide A., et al., "High-affinity single-domain binding proteins with a binary-code interface," *Proceedings of the National Academy of Sciences of the USA*, vol. 104, Issue No. 16, pp. 6632-6637 (Apr. 2007).
Koivunen E., et al., "Selection of Peptides Binding to the $\alpha_5\beta_1$ Integrin from Phage Display Library," *The Journal of Biological Chemistry*, vol. 268, Issue No. 27, pp. 20205-20210 (Sep. 1993).
Kolkman J.A., et al., "Directed evolution of proteins by exon shuffling," *Nature Biotechnology*, vol. 19, pp. 423-428 (May 2001).
König R., "Interactions between MHC molecules and co-receptors of the TCR," *Current Opinion in Immunology*, pp. 75-83 (Mar. 2002).
Kontermann R.E., "Dual targeting strategies with bispecific antibodies," *mAbs*, vol. 4, Issue No. 2, pp. 182-197 (Mar. 2012).
Koren E., et al., "Immune Responses to Therapeutic Proteins in Humans—Clinical Significance, Assessment and Prediction," *Current Pharmaceutical Biotechnology*, vol. 3, pp. 349-360 (2002).
Krebber C., et al., "Selectively-infective Phage (SIP): A Mechanistic Dissection of a Novel in vivo Selection for Protein-ligand Interactions," *Journal of Molecular Biology*, vol. 268, Issue No. 9, pp. 607-618 (May 1997).
Kunkel T.A., "Rapid and efficient site-specific mutagenesis without phenotype selection," *Proceedings of National Academy of Sciences of the USA*, vol. 82, pp. 488-492 (Jan. 1985).
Kufer P., et al., "A revival of bispecific antibodies," *Trends in Biotechnology*, vol. 22, Issue No. 5, pp. 238-244 (May 2004).
Laffly E., et al., "Monoclonal and recombinant antibodies, 30 years after . . . ," *Human Antibiotics*, vol. 14, pp. 33-55 (2005).
Laugel B., et al., "Design of Soluble Recombinant T Cell Receptors for Antigen Targeting and T Cell Inhibition," *The Journal of Biological Chemistry*, vol. 280, Issue No. 3, pp. 1882-1892 (Jan. 2005).
Lauvrak V., et al., "Identification and Characterisation of C1q-Binding Phage Displayed Peptides," *Biology Chemistry*, vol. 378, Issue No. 12, pp. 1509-1519 (Dec. 1997).
Lazar E., et al., "Transforming Growth Factor $\alpha$: Mutation of Aspartic Acid 47 and Leucine 48 Results in Different Biological Activities," *Molecular and Cellular Biology*, pp. 1247-1252 (Mar. 1988).
Le Gall F., et al., "Effect of linker sequences between the antibody variable domains on the formation, stability and biological activity of a bispecific tandem diabody," *Protein Engineering, Design & Selection*, vol. 17, Issue No. 4, pp. 357-366 (2004).

(56) References Cited

OTHER PUBLICATIONS

Lea S., et al., "Analysis of antigenic surfaces of proteins," *The FASEB Journal*, vol. 9, Issue No. 1, pp. 87-93 (Jan. 1995).

Lederman S., et al., "A Single Amino Acid Substitution in a Common African Allele of the CD4 Molecule Ablates Binding of the Monoclonal Antibody, OKT4," *Molecular Immunology*, vol. 28, Issue No. 11, pp. 1171-1181 (Nov. 1991).

Lee J.S., et al., "Surface-displayed viral antigens on *Salmonella* carrier vaccine," *Nature Biotechnology*, vol. 18, Issue No. 6, pp. 645-648 (Jun. 2000).

Lefranc M.P., et al., "IMGT, the international ImMunoGeneTics database," *Nucleic Acids Research*, vol. 27, Issue No. 1, pp. 209-212 (Jan. 1999).

Lefranc M.P., et al., "IMGT, the international ImMunoGeneTics database," *Nucleic Acids Research*, vol. 29, Issue No. 1, pp. 207-209 (2001).

Lefranc M.P., et al., "IMGT, the international ImMunoGeneTics database," *Nucleic Acids Research*, vol. 31, Issue No. 1, pp. 307-310 (2003).

Lefranc M.P., et al., "IMGT unique numbering for immunoglobulin and T cell receptor constant domains and Ig superfamily C-like domains," *Developmental and Comparative Immunology*, vol. 27, pp. 55-77 (2003).

Lefranc M.P., et al., "IMGT, the international ImMunoGeneTics Information System," *Nucleic Acids Research*, vol. 33, Database issue, pp. D593-D597 (2005).

Lefranc M.P., et al., "IMGT unique numbering for immunoglobulin and T cell receptor constant domains and Ig superfamily C-like domains," *Developmental and Comparative Immunology*, vol. 29, pp. 185-203 (2005).

Leung K.M., et al., "A HER2-specific Modified Fc Fragment (Fcab) Induces Antitumor Effects Through Degradation of HER2 and Apoptosis," *Molecular Therapy*, vol. 23, Issue No. 11, pp. 1722-1733 (Nov. 2015).

Li C.H., et al., "β-Endorphin omission analogs: Dissociation of immunoreactivity from other biological activities," *Proceedings of the National Academy of Sciences of the USA*, vol. 77, Issue No. 6, pp. 3211-3214 (Jun. 1980).

Li Y., et al., "Directed evolution of human T-cell receptors with picomolar affinities by phage display," *Nature Biotechnology*, vol. 23, Issue No. 3, pp. 349-354 (Mar. 2005).

Liang W.C., et al., "Cross-species Vascular Endothelial Growth Factor (VEGF)-blocking Antibodies Completely Inhibit the Growth of Human Tumor Xenografts and Measure the Contribution of Stromal VEGF," *The Journal of Biological Chemistry*, vol. 28, Issue No. 2, pp. 951-961 (Jan. 2006).

Lo Conte L., et al., "The Atomic Structure of Protein-Protein Recognition Sites," *Journal of Molecular Biology*, vol. 285, pp. 2177-2198 (Feb. 1999).

Lowman H.B., et al., "Selecting High-Affinity Binding Proteins by Monovalent Phage Display," *Biochemistry*, vol. 30, pp. 10832-10838 (Nov. 1991).

Lutz S., et al., "Creating multiple-crossover DNA libraries independent of sequence identity," *Proceedings of the National Academy of Sciences of the USA*, vol. 98, Issue No. 20, pp. 11248-11253 (Sep. 2001).

Malmborg A.C., et al., "Selective Phage Infection Mediated by Epitope Expression on F Pilus," *Journal of Molecular Biology*, vol. 273, pp. 544-551 (Oct. 1997).

Mrhalova M., et al., "Relative Quantification of ERBB2 mRNA in Invasive Duct Carcinoma of the Breast: Correlation with ERBB-2 Protein Expression and ERBB2 Gene Copy Number," *Pathology Research and Practice*, vol. 199, pp. 453-461 (2003).

Marvin J. S., et al., "Recombinant approaches to IgG-like bispecific antibodies," *Acta Pharmacologica Sinica*, vol. 6, pp. 649-658 (Jun. 2005).

Masuda K., et al., "The role of interface framework residues in determining antibody $V_H/V_L$ interaction strength and antigen-binding affinity," *The FEBS Journal*, vol. 273, pp. 2184-2194 (May 2006).

Mattheakis L.C., et al., "An in vitro polysome display system for identifying ligands from very large peptide libraries," *Proceedings of the National Academy of Sciences of the USA*, vol. 91, pp. 9022-9026 (Sep. 1994).

Maynard J., et al., "Antibody Engineering," *Annual Review of Biomedical Engineering*, vol. 2, pp. 339-376 (2000).

McCall A.M., et al., "Increasing the Affinity for Tumor Antigen Enhances Bispecific Antibody Cytotoxicity," *The Journal of Immunology*, vol. 6, pp. 6112-6117 (2001).

McCall A.M., et al., "Isolation and characterization of an anti-CD16 single-chain Fv fragment and construction of an anti-HER2/neu/anti-CD16 bispecific scFv that triggers CD16-dependent tumor cytolysis," *Molecular Immunology*, vol. 36, pp. 433-446 (1999).

Miyazaki C., et al., "Changes in the specificity of antibodies by site-specific mutagenesis followed by random mutagenesis," *Protein Engineering*, vol. 12, Issue No. 5, pp. 407-415 (1999).

Molloy P.E., et al., "Soluble T cell receptors: novel immunotherapies," *Current Opinion in Pharmacology*, vol. 5, Issue No. 4, pp. 438-443 (Aug. 2005).

Mosquera L.A., et al., "In Vitro and In Vivo Characterization of a Novel Antibody-Like Single-Chain TCR Human IgG1 Fusion Protein," *The Journal of Immunology*, vol. 174, Issue No. 7, pp. 4381-4388 (Apr. 2005).

Moza B., et al., "Long-range cooperative binding effects in a T cell receptor variable domain," *Proceedings of the National Academy of Sciences of the USA*, vol. 103, Issue No. 26, pp. 9867-9872 (Jun. 2006).

Munoz-Olaya J.M., "Advancing Novel Bispecific Antibody Biologics," Cambridge Healthtech Institute's Inaugural Phase and Yeast Display of Antibodies, Empowering Novel Biologics, *Seventh Annual PEGS Europe Protein & Antibody Engineering Summit*, 6 pages (Nov. 3-4, 2014).

Nakauchi H., et al., "Molecular cloning of Lyt-2, a membrane glycoprotein marking a subset of mouse T lymphocytes: Molecular homology to its human counterpart, Leu-2/T8, and to immunoglobulin variable regions," *Proceeding of the National Academy of Sciences of the USA*, vol. 82, Issue No. 15, pp. 5126-5130 (Aug. 1985).

National Science Foundation, "ABI Innovation: Predicting the combined impact of multiple mutations on protein functional adaptation," Award Abstract #1262435, 2 pages (2012).

Nemoto N., et al., "In vitro virus: Bonding of mRNA bearing puromycin at the 3'-terminal end to the C-terminal end of its encoded protein on the ribosome in vitro," *FEBS Letters*, vol. 414, pp. 405-408 (Sep. 1997).

Ngo, J.T., et al., "Computational Complexity, Protein Structure Prediction, and the Levinthal Paradox," Chapter 14, excerpts from *The Protein Folding Problem and Tertiary Structure Prediction* (including cover and title pages), pp. 491-495 (1994).

Nygren P.A., et al., "Scaffold for engineering novel binding sites in proteins," *Current Biology, Engineering and Design*, vol. 7, pp. 463-469 (1997).

Park B.W., et al., "Rationally designed anti-HER2/neu peptide mimetic disables $P185^{HER2/neu}$ tyrosine kinases in vitro and in vivo," *Nature Biotechnology*, vol. 18, pp. 194-198 (Feb. 2000).

Paul W.E. (Edtr.), "Structure and Function of Immunoglobulins", *Fundamental Immunology*, Chapter 9, Third Edition, Raven Press, pp. 292-295 (1993).

Pelletier J.N., et al., "Oligomerization domain-directed reassembly of active dihydrofolate reductase from rationally designed fragments," *Proceedings of the National Academy of Sciences of the USA*, vol. 95, pp. 12141-12146 (Oct. 1998).

Perosa F., et al., "CD20 Mimicry by a mAb Rituximab-Specific Linear Peptide. A Potential Tool for Active Immunotherapy of Autoimmune Diseases," *Annals New York Academy of Sciences*, pp. 672-683 (2005).

Philippidis A., "Companion Diagnostics: 52 Pick-Up," *Genetic Engineering & Biotechnology News, Insight & Intelligence*, 6 pages (May 2013).

Presta L.G., et al., "Engineering therapeutic antibodies for improved function," *Biochemical Society*, vol. 30, Issue No. 4, pp. 487-490 (Mar. 2002).

(56) References Cited

OTHER PUBLICATIONS

Privezentzev C.V., Poster: "F-star: Advancing Novel Bispecific Antibody Biologics," *Gordon Research Conference; Antibody Biology & Engineering*, 1 page (Mar. 2014).
Reiter Y., et al., "Construction of a Functional Disulfide-Stabilized TCR Fv Indicates that Antibody and TCR Fv Frameworks Are Very Similar in Structure," *Immunity*, vol. 2, Issue No. 3, pp. 281-287 (Mar. 1995).
Richman S.A., et al., "Development of a novel strategy for engineering high-affinity proteins by yeast display," *Protein Engineering, Design & Selection*, vol. 19, Issue No. 6, pp. 255-264 (2006).
Richman S.A., et al., "Structural features of T cell receptor variable regions that enhance domain stability and enable expression as single-chain VαVβ fragments," *Molecular Immunology*, vol. 46, Issue No. 5, pp. 902-916 (Feb. 2009).
Riechmann L., et al., "Single domain antibodies: comparison of camel VH and camelised human VH domains," *Journal of Immunological Methods*, vol. 231, pp. 25-38 (1999).
Roberts R.W., et al., "RNA-peptide fusions for the in vitro selection of peptides and proteins," *Proceedings of the National Academy of Sciences of the USA*, vol. 94, pp. 12297-12302 (Nov. 1997).
Roitberg A., et al., "Modeling Side Chains in Peptides and Proteins with Locally Enhanced Sampling/Simulated Annealing Method", Chapter 1, excerpts from *The Protein Folding Problem and Tertiary Structure Prediction* (including cover and title pages), pp. 1-51, Merz K.M., et al. (Edtrs.) (1994).
Rondot S., et al., "A helper phage to improve single-chain antibody presentation in phage display," *Nature Biotechnology*, vol. 19, pp. 75-78 (Jan. 2001).
Roovers R.C., et al., "Efficient inhibition of EGFR signalling and of tumour growth by antagonistic anti-EFGR Nanobodies," *Cancer Immunology, Immunotherapy*, vol. 56, pp. 303-317 (2007).
Rudikoff S., et al., "Single amino acid substitution altering antigen-binding specificity," *Proceedings of the National Academy of Sciences of the USA*, vol. 79, pp. 1979-1983 (Mar. 1982).
Ruiz M., et al., "IMGT, the international ImMunoGeneTics database," *Nucleic Acids Research*, vol. 28, Issue No. 1, pp. 219-221 (2000).
Rüker F., et al., "Expression of a Human Monoclonal Anti-HIV-1 Antibody in CHO Cells," *Annals of New York Academy of Sciences*, vol. 646, pp. 212-219 (Dec. 1991).
Rüker F., "Modular Antibody Technology", F-Star Fact Sheet, 2 pages (Feb. 2008) Retrieved online: [www.boku.ac.at/fileadmin/BOKU-Topstories/20080702_Rueker_Factsheet.pdf].
Rüker F., "Modular Antibody Technology", F-Star Fact Sheet, 2 pages (Feb. 2008) Retrieved online: [www.boku.ac.atifileadmin/BOKU-Topstories/20080702_Rueker_Factsheet.pdf] [English Translation].
Salfield J.G., "Isotype selection in antibody engineering," *Nature Biotechnology*, vol. 25, Issue No. 12, pp. 1369-1372 (Dec. 2007).
Saerens D., et al., "Identification of a Universal VHH Framework to Graft Non-canonical Antigen-binding Loops of Camel Single-domain Antibodies," *Journal of Molecular Biology*, vol. 352, pp. 597-607 (2005).
Schaffitzel C., et al., "Ribosome display: an in vitro method for selection and evolution of antibodies from libraries," *Journal of Immunological Methods*, vol. 231, pp. 119-135 (1999).
Schmittel A., et al., "Application of the IFN-γ ELISPOT assay to quantify T cell responses against proteins," *Journal of Immunological Methods*, vol. 247, pp. 17-24 (Jan. 2001).
Shao Z., et al., "Random-priming in vitro recombination: an effective tool for directed evolution," *Nucleic Acids Research*, vol. 26, Issue No. 2, pp. 681-683 (1998).
Shields R.L., et al., "High Resolution Mapping of the Binding Site on Human IgG1 for FcγRI, FcγRII, FcγRIII, and FcRn and Design of IgG1 Variants with Improved Binding to the FcγR," *The Journal of Biological Chemistry*, vol. 276, Issue No. 9, pp. 6591-6604 (Mar. 2001).
Short M.K., et al., "Contribution of Antibody Heavy Chain CDR1 to Digoxin Binding Analyzed by Random Mutagenesis of Phage-displayed Fab 26-10," *The Journal of Biologival Chemistry*, vol. 270, Issue No. 48, pp. 28541-28550 (Dec. 1995).
Shusta E.V., et al., "Directed evolution of a stable scaffold for T-cell receptor engineering," *Nature Biotechnology*, vol. 18, No. 7, pp. 754-759 (Jul. 2000).
Sidhu S.S., et al., "Synthetic therapeutic antibodies," *Nature Chemical Biology*, vol. 2, Issue No. 12, pp. 682-688 (Dec. 2006).
Simon T., et al., "A functional antibody mutant with an insertion in the framework region 3 loop of the $V_H$ domain: implications for antibody engineering," *Protein Engineering*, vol. 5, Issue No. 3, pp. 229-234 (1992).
Skolnick J., et al., "From genes to protein structure and function: novel applications of computational approaches in the genomic era," *Trends in Biotechnology*, vol. 18, pp. 34-39 (Jan. 2000).
Smith G.P., "Filamentous Fusion Phage: Novel Expression Vectors That Display Cloned Antigens on the Virion Surface," *Science*, vol. 228, Issue No. 4705, pp. 1315-1317 (Jun. 1985).
Spiridon C.I., et al., "Targeting Multiple Her-2 Epitopes with Monoclonal Antibodies Results in Improved Antigrowth Activity of a Human Breast Cancer Cell Line in Vitro and in Vivo," *Clinical Cancer Research*, vol. 8, pp. 1720-1730 (Jun. 2002).
Stagg J., et al., "Anti-ErbB-2 mAb therapy requires type I and II interferons and synergizes with anti-PD-1 or anti-CD137 mAb therapy," *Proceedings of the National Academy of Sciences of the USA*, vol. 108, Issue No. 17, pp. 7142-7147 (Apr. 2011).
Tangri S., et al., "Rationally Engineered Therapeutic Proteins with Reduced Immunogenicity," *The Journal of Immunology*, vol. 174, Issue No. 6, pp. 3187-3196 (Mar. 2005).
Tolaney S.M., et al., "Adjuvant Paclitaxel and Trastuzumab for Node-Negative, HER2-Positive Breast Cancer," *The New England Journal of Medicine*, vol. 372, pp. 134-141 (Jan. 2015).
Traxlmayr M.W., et al., "Directed evolution of Her2/neu-binding IgG1-Fc for improved stability and resistance to aggregation by using yeast surface display," *Protein Engineering, Design & Selection*, vol. 26, Issue No. 4, pp. 255-265 (2013).
Traxlymayr M.W., et al., "Construction of pH-Sensitive Her2-binding IgG1-Fc by Directed Evolution," *Biotechnology*, vol. 9, pp. 1013-1022 (2014).
Uhlenbroich S., Poster: "F-star: Advancing Novel Bispecific Antibody Biologics," *Empowered Antibodies Congress*, 1 page (Jun. 18-19, 2014) [Abstract].
Vajdos F.F., et al., "Comprehensive Functional Maps of the Antigen-binding Site of an Anti-ErbB2 Antibody Obtained with Shotgun Scanning Mutagenesis," *Journal of Molecular Biology*, vol. 320, Issue No. 2, pp. 415-428 (Jul. 2002).
Virnekäs B., et al., "Trinucleotide Phosphoramidites: Ideal Reagents for the Synthesis of Mixed Oligonucleotides for Random Mutagenesis," *Nucleic Acids Research*, vol. 22, Issue No. 25, pp. 5600-5607 (1994).
Visintin M., et al., "Selection of antibodies for intracellular function using a two-hybrid in vivo system," *Proceedings of the National Academy of Sciences of the USA*, vol. 96, Issue No. 21, pp. 11723-11728 (Oct. 1999).
Vogt M., et al., "Construction of an Artificial Receptor Protein ("Anticalin") Based on the Human Apolipoprotein D," *ChemBioChem*, vol. 5, Issue No. 2, pp. 191-199 (Feb. 2004).
Wang W., et al., "Expression Patterns and Transcript Processing of ftt-1 and ftt-2, two *C. elegans* 14-3-3 Homologues," *Journal of Molecular Biology*, vol. 268, pp. 619-630 (1997).
Wang L., et al., "Retargeting T Cells for HER2-Positive Tumor Killing by a Bispecific Fv-Fc Antibody," *PLOS One*, vol. 8, Issue No. 9, pp. e75589-1-e75589-11 (Sep. 2013).
Weaver-Feldhaus J.M., et al., "Yeast mating or combinatorial Fab library generation and surface display," *FEBS Letters*, vol. 564, Issue Nos. 1-2, pp. 24-34 (Apr. 2004).
Weber K.S., et al., "Class II-restricted T cell receptor engineered in vitro for higher affinity retains peptide specificity and function," *Proceedings of the National Academy of Sciences of the USA*, vol. 102, Issue No. 52, pp. 19033-19038 (Dec. 2005).
Weiner M.P., et al., "Site-directed mutagenesis of double-stranded DNA by the polymerase chain reaction," *Gene*, vol. 151, Issue No. 1-2, pp. 119-124 (Dec. 1994).

(56) References Cited

OTHER PUBLICATIONS

Whitehorn E.A., et al., "A Generic Method for Expression and Use of "Tagged" Soluble Versions of Cell Surface Receptors," *Biotechnology*, vol. 13, Issue No. 11, pp. 1215-1219 (Nov. 1995).
Willcox B.E., et al., "Production of soluble αβ T-cell receptor heterodimers suitable for biophysical analysis of ligand binding," *Protein Science*, vol. 8, Issue No. 11, pp. 2418-2423 (Nov. 1999).
Winter G., et al., "Humanized antibodies," *Immunology Today*, vol. 14, Issue No. 6, pp. 243-246 (1993).
Winkler K., et al., "Changing the Antigen Binding Specificity by Single Point Mutations of an Anti-p24 (HIV-1) Antibody," *The Journal of Immunology*, vol. 165, Issue No. 8, pp. 4505-4514 (Oct. 2000).
Wittrup K.D., "Protein engineering by cell-surface display," *Current Opinion in Biotechnology*, vol. 12, Issue No. 4, pp. 395-399 (Aug. 2001).
Woisetschläger M., et al., "In vivo and in vitro activity of an immunoglobulin Fc fragment (Fcab) with engineered Her-2/neu binding sites," *Biotechnology Journal*, vol. 9, Issue No. 6, pp. 844-851 (Jun. 2014).
Wolff A.C., et al., "American Society of Clinical Oncology/College of American Pathologists Guideline Recommendations for Human Epidermal Growth Factor Receptor 2 Testing in Breast Cancer," *Journal of Clinical Oncology*, vol. 25(1), pp. 118-145 (Jan. 2007).
Wozniak-Knopp G., et al., "Introducing antigen-binding sites in structural loops of immunoglobulin constant domains: Fc fragments with engineered HER2/neu-binding sites and antibody properties," *Protein Engineering, Design & Selection*, vol. 23, Issue No. 4, pp. 289-297 (Apr. 2010).
Wu H., et al., "Humanization of a Murine Monoclonal Antibody by Simultaneous Optimization of Framework and CDR Residues," *Journal of Molecular Biology*, vol. 294, Issue No. 1, pp. 151-162 (Nov. 1999).
Wülfing C., et al., "Correctly Folded T-cell Receptor Fragments in the Periplasm of *Escherichia coli*: Influence of Folding Catalysts," *Journal of Molecular Biology*, vol. 242, Issue No. 5, pp. 655-669 (Oct. 1994).
Xiao X., et al., "A large library based on a novel (CH2) scaffold: identification of HIV-1 inhibitors," *Biochemical and Biophysical Research Communications*, vol. 387, Issue No. 2, pp. 387-392 (Sep. 2009).
Yánez J., et al. "Combinatorial condon-based amino acid substitutions," *Nucleic Acids Research*, vol. 32, Issue No. 20, pp. 1-10 (Nov. 2004).
Yau K.Y.F., et al., "Affinity maturation of a VHH by mutational hotspot randomization," *Journal of Immunological Methods*, vol. 297, Issue Nos. 1-2, pp. 213-224 (Feb. 2005).
Ying T., et al., "Soluble Monomeric IgG1 Fc," *The Journal of Biological Chemistry*, vol. 287, issue No. 3, pp. 19399-19408 (Jun. 2003).
Zemlin M., et al., "Expressed Murine and Human CDR-H3 Intervals of Equal Length Exhibit Distinct Repertoires that Differ in their Amino Acid Composition and Predicted Range of Structures," *Journal of Molecular Biology*, vol. 334, Issue No. 4, pp. 733-749 (Dec. 2003).
Zhou J.M., et al., "A Novel Strategy by the Action of Ricin that Connects Phenotype and Genotype without Loss of the Diversity of Libraries," *Journal of American Chemical Society*, vol. 124, Issue No. 4, pp. 538-543 (Jan. 2002).
Zhao H., et al., "Molecular evolution by staggered extension process (StEP) in vitro recombination," *Nature Biotechnology*, vol. 16, pp. 258-261 (Mar. 1998).
Canadian Intellectual Property Office, Official Action—Application No. 2,721,614, dated Mar. 16, 2015 (3 pages).
State Intellectual Property Office of People's Republic of China, Initial Search Report—Application No. 200780032991.X, 2 pages (dated May 18, 2015) [English Translation].
Michael Huang Chemical & Biotech Dept. China Patent Agent (H.K.) Ltd., Response to Office Action—Application No. 200780032991X, 7 pages, filed Oct. 6, 2015.

State Intellectual Property Office of People's Republic of China, Third Office Action—Application No. 200780032857, 4 pages (dated Sep. 23, 2015).
State Intellectual Property Office of People's Republic of China, Third Office Action—Application No. 200780032857, 4 pages (dated Sep. 23, 2015) [English Translation].
Archana Shanker Anand and Anand, Response to First Examination Report—Application No. 4657/DELNP/2007, 8 pages (dated Jan. 17, 2014).
European Patent Office, Communication pursuant to Article 94(3) EPC—Application No. 08 756 842.4, 7 pages (dated Jun. 14, 2010).
European Patent Office—The Hague, Extended European Search Report—Application No. EP 14191631.2-1405, 11 pages (dated Jun. 16, 2015).
European Patent Office, Communication Under Rule 71(3) EPC—Application No. 14 781 645.8-1403, 7 pages (dated Aug. 14, 2017).
European Patent Office, Munich, Extended European Search Report—Application No. EP 17 18 2619.1, 9 pages (dated Nov. 23, 2017).
Japanese Patent Office, Office Action—Application No. 2013-246485, 2 pages (dated Mar. 3, 2015).
Japanese Patent Office, Office Action—Application No. 2013-246485, 2 pages (dated Mar. 3, 2015) [English Translation].
Rebecca Hix, Authorized officer International Searching Authority, International Search Report—International Application No. PCT/AT2007/000313, 3 pages (dated Feb. 29, 2008).
Rebecca Hix, Authorized officer International Searching Authority, Written Opinion of the International Searching Authority, Application No. PCT/AT2007/000313, 9 pages (dated Jan. 5, 2009).
Yolaine Cussac, Authorized officer International Bureau of WIPO, International Preliminary Report on Patentability, International Application PCT/AT2007/000313, 10 pages (dated Jan. 6, 2009), together along with the Written Opinion of the International Searching Authority.
European Patent Office, International Search Report—International Application No. PCT/AT2008/000232, 4 pages (dated Oct. 13, 2008), together along with the Written Opinion of the International Searching Authority.
Yolaine Cussac, Authorized officer, International Bureau of WIPO, International Preliminary Report on Patentability, International Application PCT/AT2008/000232, 10 pages (dated Jan. 5, 2010), together along with the Written Opinion of the International Searching Authority.
Zoran Cilensek, Authorized officer, International Searching Authority, International Search Report—Application No. PCT/EP2009/052509, 14 pages (dated Jun. 3, 2009), together with the Written Opinion of the International Searching Authority.
The International Bureau of WIPO, International Preliminary Report on Patentability, Application No. PCT/EP2009/052509, 8 pages (dated Nov. 2, 2010).
Miguel Aguilera, Authorized officer European Patent Officer, International Search Report—Application No. PCT/GB2014/052994, 5 pages (dated Jan. 9, 2015).
International Searching Authority, Written Opinion of International Searching Authority, Application No. PCT/GB2014/052994, 6 pages (dated Jan. 9, 2015).
Athina-Nickitas-Etienne, Authorized officer The International Bureau of WIPO, International Preliminary Report on Patability—Application PCT/GB2014/052994, 7 pages (dated Apr. 5, 2016), together with the Written Opinion of the International Searching Authority.
Rebecca Hix, Authorized officer European Patent Office, International Search Report—Application No. PCT/EP2016/057800, 15 pages (dated Jun. 24, 2016), together with the Written Opinion of the International Searching Authority.
Fu Yiloong (Dr.), Authorized officer Intellectual Property Office of Singapore, Written Opinion—Application No. 11201602605T, 7 pages (dated Dec. 20, 2016).
U.S. Appl. No. 12/307,578, filed Jun. 26, 2007.
U.S. Appl. No. 12/307,569, filed Jul. 5, 2007 (now U.S. Pat. No. 9,133,274, issued on Sep. 15, 2015).
U.S. Appl. No. 12/307,582, filed Jul. 5, 2007.
U.S. Appl. No. 12/666,618, filed Dec. 23, 2009 (now U.S. Pat. No. 8,921,279, issued on Dec. 30, 2014).

(56) References Cited

OTHER PUBLICATIONS

U.S. Appl. No. 12/990,119, filed Oct. 28, 2010 (now U.S. Pat. No. 8,859,738, issued on Oct. 14, 2014).
U.S. Appl. No. 13/149,871, filed May 31, 2011 (now U.S. Pat. No. 9,856,311 issued on Jan. 2, 2018).
U.S. Appl. No. 13/151,195, filed Jun. 1, 2011 (now U.S. Pat. No. 9,045,528, issued on Jun. 2, 2015).
U.S. Appl. No. 13/228,559, filed Sep. 9, 2011.
U.S. Appl. No. 14/470,425, filed Aug. 27, 2014.
U.S. Appl. No. 14/556,662, filed Dec. 1, 2014 (now U.S. Pat. No. 9,651,559, issued on May 16, 2017).
U.S. Appl. No. 14/629,760, filed Feb. 24, 2015 (now U.S. Pat. No. 9,255,149, issued on Feb. 9, 2016).
U.S. Appl. No. 14/853,919, filed Sep. 14, 2015.
U.S. Appl. No. 15/004,692, filed Jan. 22, 2016.
U.S. Appl. No. 15/087,272, filed Mar. 31, 2016.
U.S. Appl. No. 15/284,471, filed Oct. 3, 2016.
U.S. Appl. No. 15/596,596, filed May 16, 2017.
U.S. Appl. No. 15/676,737, filed Aug. 14, 2017.
U.S. Appl. No. 15/677,667, filed Aug. 15, 2017.
Haurum J., Poster: "How to Leverage Oncogene Addiction: Targeted Biological Therapy Inducing Growth Factor Receptor Internalization and Degradation," PEPtalk: The Protein Science Week, 1 page, Jan. 19, 2015.
European Patent Office, Extended European Search Report—Application No. 17159886, 17 pages (dated Aug. 16, 2017).
Japanese Patent Office, Notice of Reasons for Rejection—Application No. 2016-546183, dated Jul. 31, 2018, 5 pages [English Translation].
Gong R., et al., "Engineered Human Antibody Constant Domains with Increased Stability," *The Journal of Biological Chemistry*, vol. 284, Issue No. 28, pp. 14203-14210 (May 2009).
Ruediger Grosskopf, Authorized officer European Patent Office, International Search Report—International Application No. PCT/AT2007/000342, 12 pages (dated Sep. 20, 2007), together along with the Written Opinion of the International Searching Authority.
Elena Armandola, Authorized officer European Patent Office, International Search Report—International Application No. PCT/AT2007/000343, 11 pages (dated Mar. 10, 2008), together along with the Written Opinion of the International Searching Authority.
W. van Klompenburg, Authorized officer European Patent Office, International Search Report—Application No. PCT/EP2006/050059, 8 pages, dated Jun. 19, 2006, together with the Written Opinion of the International Searching Authority.
René Wagner, Authorized officer European Patent Office, International Search Report—International Application No. PCT/EP2010/059408, 14 pages (dated Aug. 31, 2010), together along with the Written Opinion of the International Searching Authority.
Rob Chapman, Authorized officer European Patent Office, International Search Report—International Application No. PCT/EP2011/003518, 14 pages (dated Aug. 31, 2011), together along with the Written Opinion of the International Searching Authority.
U.S. Appl. No. 13/086,897, filed Apr. 14, 2011.

```
                                                                                                    BssS1
     R   E   P   Q   V   Y   T   L   P   P   S   R   D   E   L   Q   V   S   L   T   C   L   V   K   G   F
 +3  NNSCGAGAAC CACAGGTGTA CACCCTGCCC CCATCCCGTG ACGAGCTCNN SNNSNNSCAA GTCAGCCTGA CCTGCCTNGT GAAAGGCTTC NNSNNSNNSN
  1  NNSGCTCTTG GTGTCCACAT GTGGGACGGG GGTAGGGCAC TGCTCGAGNN SNNSNNSGTT CAGTCGGACT GGACGGAGCA CTTTCCGAAG NNSNNSNNSN
                                                                    XbaI                               S   F
     I   A   V   E   W   E   S   N   G   Q   P   E   N   Y   K   T   T   P   P   V   L   D   S   D   G
+3   NSATCGCCGT GGAGTGGGAG AGCAATGGGC AGCCCGAGAA CAACTACAAG ACCACGCCTC CCGTTCTNGA CTCCGACGGC NNSNNSNNSN NSNNSTCCTT
101  NSTAGCGGCA CCTCACCCTC TCGTTACCCG TCGGGCTCTT GTTGATGTTC TGGTGCGGAG GGCAAGATCT GAGGCTGCCG NNSNNSNNSN NSNNSAGGAA

BtsI
     F   L   Y   S   K   L   T   V           R   W       G   N   V   F   S   C   S   V   M           L   H   N   H   Y   F
+3   CTTCCCTAC AGCAAGCTTA CCGTGNNSNN SNNSAGGTGG NNSNNSGGGA ACGTCTTCTC ATGCNNSGTG ATGNNSNNSN NSCTGCACAA CCACTACACA
201  GAAGGAGATG TCGTTCGAAT GGCACNNSNN SNNSTCCACC NNSNNSCCCT TGCAGAAGAG TACGTCACAC TACNNSNNSN NSGACGTGTT GGTGATGTGT

NotI
     Q   K   S   L   S   L   S   P   G   K   A   A   A
+3   CAGAAGAGCC TCTCCCTGTC TCCGGGTAAA GCGGCCGCA       (SEQ ID NO:66)
301  GTCTTCTCGG AGAGGGACAG AGGCCCATTT CGCCGGCGT       (SEQ ID NO:67)
```

Fig. 7

Fig. 8

SEQ ID No. 1: Amino acid sequence of C$_H$3 domain of antibody 1oqo.pdb

1   P R E P Q V Y T L P P S R D E L T K N Q V S L T C L V K G F
31  Y P S D I A V E W E S N G Q P E N N Y K T T P P V L D S D G
61  S F F L Y S K L T V D K S R W Q Q G N V F S C S V M H E A L
91  H N H Y T Q K S L S L S P G K A A A

SEQ ID No. 2: Nucleotide sequence of the engineered C$_H$3 domain of Example 1

1 CCATGGCCCC CCGAGAACCA CAGGTGTACA CCCTGCCCCC ATCCCGGGAT GAGCTCNNSN NSNNSCAGGT
71 CAGCCTGACC TGCCTGGTCA AAGGCTTCTA TCCCAGCGAC ATCGCCGTGG AGTGGGAGAG CAATGGGCAG
141 CCGGAGAACA ACTACAAGAC CACGCCTCCC GTGCTGGACT CCGACGGCTC CTTCTTCCTC TACAGCAAGC
211 TTACCGTGNN SNNSNNSAGG TGGNNSNNSG GGAACGTCTT CTCATGCTCC GTGATGCATG AGGCTCTGCA
281 CAACCACTAC ACACAGAAGA GCCTCTCCCT GTCTCCGGGT AAAGCGGCCG CA

SEQ ID No. 3: Amino acid sequence of the engineered C$_H$3 domain of Example 1

1   M A P R E P Q V Y T L P P S R D E L X X X Q V S L T C L V K
31  G F Y P S D I A V E W E S N G Q P E N N Y K T T P P V L D S
61  D G S F F L Y S K L T V X X X R W X X G N V F S C S V M H E
91  A L H N H Y T Q K S L S L S P G K A A A

SEQ ID No. 4: PCR primer C$_H$3LNCO cttgccatgg cccccgaga accacaggtg tac

SEQ ID No. 5: PCR primer C$_H$3LSAC agtcgagctc gtcacgggat ggggcaggg

SEQ ID No. 6: PCR primer C$_H$3CSAC

Fig. 8 continued gtacgagctc nnsnnsnnsc aagtcagcct gacctgcctg g

SEQ ID No. 7: PCR primer C$_H$3CHIN tgccaagctt gctgtagagg aagaaggagc cg

SEQ ID No. 8: PCR primer C$_H$3RHIN tgccaagctt accgtgnnsn nsnnsaggtg gnnsnnsggg aacgtcttct catgctccg SEQ ID No. 9: PCR primer C$_H$3RNOT agttgcggcc gctttacccg gagacaggga gag SEQ ID No. 10: Amino acid sequence of the engineered C$_H$3+3 domain

```
  1  M A P R E P Q V Y T L P P S R D E L X X X Q V S L T C L V K
 31  G F Y P S D I A V E W E S N G Q P E N N Y K T T P P V L D S
 61  D G S F F L Y S K L T V X X X X X X X R W X X G N V F S C S V
 91  M H E A L H N H Y T Q K S L S L S P G K A A A
```

SEQ ID No. 11: Nucleotide sequence of the engineered C$_H$3+3 domain

```
  1  ccatggcccc ccgagaacca caggtgtaca ccctgccccc atcccgtgac gagctcnnsn
 61  nsnnscaagt cagcctgacc tgcctggtca aaggcttcta tcccagcgac atcgccgtgg
121  agtgggagag caatgggcag ccggagaaca actacaagac cacgcctccc gtgctggact
181  ccgacggctc cttcttcctc tacagcaagc ttaccgtgnn snnsnnsnns nnsnnsaggt
241  ggnnsnnsgg gaacgtcttc tcatgctccg tgatgcatga ggctctgcac aaccactaca
301  cacagaagag cctctccctg tctccgggta aagcggccgc a
```

SEQ ID No. 12: PCR primer C$_H$3RHIN3

```
  1  tgccaagctt accgtgnnsn nsnnsnnsnn snnsaggtgg nnsnnsggga acgtcttctc
 61  atgctccg
```

SEQ ID No. 13: Amino acid sequence of the engineered C$_H$3+5 domain

Fig. 8 continued

```
  1 MAPREPQVYTLPPSRDELXXXQVSLTCLVK
 31 GFYPSDIAVEWESNGQPENNYKTTPPVLDS
 61 DGSFFLYSKLTVXXXXXXXXRWXXGNVFSC
 91 SVMHEALHNHYTQKSLSLSPGKAAA
```

SEQ ID No. 14: Nucleotide sequence of the engineered C$_H$3+5 domain

```
  1 ccatggcccc cgagaacca caggtgtaca ccctgccccc atcccgtgac gagctcnnsn
 61 nsnnscaagt cagcctgacc tgcctggtca aaggcttcta tcccagcgac atcgccgtgg
121 agtgggagag caatgggcag ccggagaaca actacaagac cacgcctccc gtgctggact
181 ccgacggctc cttcttcctc tacagcaagc ttaccgtgnn snnsnnsnns nnsnnsnnsn
241 nsaggtggnn snnsgggaac gtcttctcat gctccgtgat gcatgaggct ctgcacaacc
301 actacacaca gaagagcctc tccctgtctc cgggtaaagc ggccgca
```

SEQ ID No. 15: PCR primer C$_H$3RHIN5

```
  1 tgccaagctt accgtgnnsn nsnnsnnsnn snnsnnsnns aggtggnnsn nsgggaacgt
 61 cttctcatgc tccg
```

SEQ ID No. 16: Amino acid sequence of anti-EpCAM clone D07

PREPQVYTLPPSRDEL<u>GWP</u>QVSLTCLVKGFYPSDIAVEWESNGQPENNYKTTPPVLDSDGSFFLYSKL
TV<u>PKRWCVSVRWPP</u>GNVFSCSVMHEALHNHYTQKSLSLSPGK

SEQ ID No. 17: Nucleotide sequence of anti-EpCAM clone D07

CCCCGAGAACCACAGGTGTACACCCTGCCCCCATCCCGTGACGAGCTCGGCTGGCCGCAAGTCA
GCCTAACCTGCCTGGTCAAAGGCTTCTATCCCAGCGACATCGCCGTGGAGTGGGAGAGCAATGG
GCAGCCGGAGAACAACTACAAGACCACGCCTCCCGTGCTGGACTCCGACGGCTCCTTCTTCCTCT
ACAGCAAGCTTACCGTGCCCAAGCGGTGGTGCGTGAGCGTCAGGTGGCCCCGGGGAACGTCTT
CTCATGCTCCGTGATGCATGAGGCTCTGCACAACCACTACACACAGAAGAGCCTCTCCCTGTCTC
CGGGTAAA

SEQ ID No. 18: Amino acid sequence of anti-EpCAM clone C67

Fig. 8 continued

PREPQVYTLPPSRDEL<u>SVS</u>QVSPTCLVKGFYPSDIAVEWESNGQPENNYKTTPPVLDSDGSFFLYSKL
TV<u>IPFCRMSPRWW</u>IGNVFSCSVMHEALHNHYTQKSLSLSPGK

SEQ ID No. 19: Nucleotide sequence of anti-EpCAM clone C67
CCCCGAGAACCACAGGTGTACACCCTGCCCCCATCCCGTGACGAGCTCTCGGTGTCGCAAGTCA
GCCCGACCTGCCTGGTCAAAGGCTTCTATCCCAGCGACATCGCAGTGGAGTGGGAGAGCAATGG
GCAGCCGGAGAACAACTACAAGACCACGCCTCCCGTGCTGGACTCCGACGGCTCCTTCTTCCTCT
ACAGCAAGCTTACCGTGATCCCCTTCTGCAGGATGAGCCCCAGGTGGTGGATCGGGAACGTCTTC
TCATGCTCCGTGATGCATGAGGCTCTGCACAACCACTACACACAGAAGAGCCTCTCCCTGTCTCC
GGGTAAA SEQ ID No. 20: Amino acid sequence of anti-Fluorescein clone D64C3
PREPQVYTLPPSRDEL<u>EAL</u>QVSLTCLVKGFYPSDIAVEWESNGQPENNYKTTPPVLDSDGSFFLYSKLT
V<u>RRNRWSW</u>GNVFSCSVMHEALHNHYTQKSLSLSPGK SEQ ID No. 21: Nucleotide sequence of anti-Fluorescein clone D64C3
CCTCGAGAACCACAGGTGTACACCCTGCCCCCATCCCGTGACGAGCTCGAGGCGCTGCAAGTCA
GCCTGACCTGCCTGGTCAAAGGCTTCTATCCCAGCGACATCGCCGTGGAGTGGGAGAGCAATGG
GCAGCCGGAGAACAACTACAAGACCACGCCTCCCGTGCTGGACTCCGACGGCTCCTTCTTCCTCT
ACAGCAAGCTTACCGTGCGGCGCAACAGGTGGTCCTGGGGGAACGTCTTCTCATGCTCCGTGATG
CATGAGGCTCTGCACAACCACTACACACAGAAGAGCCTCTCCCTGTCTCCGGGTAAA SEQ ID No. 22: Amino acid sequence of anti-Lysozyme clone A68
PREPQVYTLPPSRDEL<u>QGS</u>QVSLTCLVKGFYPSDIAVEWESNGQPENNYKTTPPVLDSDGSFFLYSKL
TV<u>KSRATRRWVV</u>GNVFSCSVMHEALHNHYTQKNLSLSPGK SEQ ID No. 23: Nucleotide sequence of anti-Lysozyme clone A68
CCCCGAGAACCACAGGTGTACACCCTGCCCCCATCCCGTGACGAGCTCCAGGGGAGCCAAGTCA
GCCTGACCTGCCTGGTCAAAGGCTTCTATCCCAGCGACATCGCCGTGGAGTGGGAGAGCAATGG
GCAGCCGGAGAACAACTACAAGACCACGCCTCCCGTGCTGGACTCCGACGGCTCCTTCTTCCTCT

Fig. 8 continued

ACAGCAAGCTTACCGTGAAGTCGCGCGCCACCCGGAGGTGGGTGGTGGGGAACGTCTTTTCTTG
CTCCGTGATGCATGAGGCTCTGCACAACCACTACACACAGAAGAACCTCTCCCTGTCTCCGGGTA
AA

SEQ ID No. 24: Amino acid sequence of anti-Lysozyme clone B23
PREPQVYTLPPSRDEL<u>AIG</u>QVSLTCLVKGFYPSDIAVEWESNGQPENNYKTTPPVLDSDGSFFLYSKLT
V<u>RSTRDNRWL</u>VGNVFSCSVMHEALHNHYTQKSLSLSPG SEQ ID No. 25: Nucleotide sequence of anti-Lysozyme clone B23
CCCCGAGAACCACAGGTGTACACCCTGCCCCCATCCCGTGACGAGCTCGCGATCGGCCAAGTCA
GCCTGACCTGCCTGGTCAAAGGCTTCTATCCCAGCGACATCGCCGTGGAGTGGGAGAGCAATGG
GCAGCCGGAGAACAACTACAAGACCACGCCTCCCGTGCTGGACTCCGACGGCTCCTTCTTCCTCT
ACAGCAAGCTTACCGTGCGCTCGACGAGGGACAACAGGTGGCTGGTGGGGAACGTCTTCTCATG
CTCCGTGATGCATGAGGCTCTGCACAACCACTACACACAGAAGAGCCTCTCCCTGTCTCCGGGTA
AA SEQ ID No. 26: Amino acid sequence of anti-Lysozyme clone B40
PREPQVYTLPPSRDEL<u>SGA</u>QVSLTCLVKGFYPSDIAVEWESNGQPENNYKTTPPVLDSDGSFFLYSKL
TV<u>WFRQEGGMRWF</u>AGNVFSCSVMHEALHNHYTQKSLSLSPGK SEQ ID No. 27: Nucleotide sequence of anti-Lysozyme clone B40
CCCCGAGAACCACAGGTGTACACCCTGCCCCCATCCCGTGACGAGCTCAGCGGGGCGCAAGTCA
GCCTGACCTGCCTGGTCAAAGGCTTCTATCCCAGCGACATCGCCGTGGAGTGGGAGAGCAATGG
GCAGCCGGAGAACAACTACAAGACCACGCCTCCCGTGCTGGACTCCGACGGCTCCTTCTTCCTCT
ACAGCAAGCTTACCGTGTGGTTCAGGCAGGAGGGCGGCATGAGGTGGTTCGCGGGGAACGTCTT
CTCATGCTCCGTGATGCATGAGGCTCTGCACAACCACTACACACAGAAGAGCCTCTCCCTGTCTC
CGGGTAAA SEQ ID No. 28: Amino acid sequence of anti-Lysozyme clone C24

Fig. 8 continued

PREPQVYTLPPSRDELVLGQVSPTCLVKGFYPSDIAVEWESNGQPENNYKTTPPVLDSDGSFFLYGKL
TVPPRLKGWPRWGWGNVFSCSVMHEALHNHYTQKSLSLSPGK

SEQ ID No. 29: Nucleotide sequence of anti-Lysozyme clone C24

CCCCGAGAACCACAGGTGTACACCCTGCCCCCATCCCGTGACGAGCTCGTCTTGGGGCAAGTCA
GCCCGACCTGCCTGGTCAAAGGCTTCTATCCCAGCGACATCGCCGTGGAGTGGGAGAGCAATGG
GCAGCCGGAGAACAACTACAAGACCACGCCTCCCGTGCTGGACTCCGACGGCTCCTTCTTCCTCT
ACGGCAAGCTTACCGTGCCCCCGCGGTTGAAGGGCTGGCCGAGGTGGGGCTGGGGGAACGTCT
TCTCATGCTCCGTGATGCATGAGGCTCTGCACAACCACTACACACAGAAGAGCCTCTCCCTGTCTC
CGGGTAAA

SEQ ID No. 30: Amino acid sequence of anti-Lysozyme clone D46

PREPQVYTLPPSRDELLAYQVSLTCLVKGFYPSDIAVEWESNGQPENNYKTTPPVLDSDGSFFLYSKLT
VVAGRWTCGNVFSCSVMHEALHNHYTQKSLSLSPGK

SEQ ID No. 31: Nucleotide sequence of anti-Lysozyme clone D46

CCCCGAGAACCACAGGTGTACACCCTGCCCCCATCCCGTGACGAGCTCCTGGCGTACCAAGTCA
GCCTGACCTGCCTGGTCAAAGGCTTCTATCCCAGCGACATCGCCGTGGAGTGGGAGAGCAATGG
GCAGCCGGAGAACAACTACAAGACCACGCCTCCCGTGCTGGACTCCGACGGCTCCTTCTTCCTCT
ACAGCAAGCTTACCGTGGTGGCCGGCAGGTGGACGTGCGGGAACGTCTTCTCATGCTCCGTGAT
GCATGAGGCTCTGCACAACCACTACACACAGAAGAGCCTCTCCCTGTCTCCGGGTAAA

SEQ ID No. 32: Amino acid sequence of anti-Lysozyme clone D56

PREPQVYTLPPSRDELCVPQVSLTCLVKGFYPSDIAVEWESNGQPENNYKTTPPVLDSDGSFFLYSKL
TVVLKVVQARRWEVGNVFSCSVMHEALHNHYTQKSLSLSPGK

SEQ ID No. 33: Nucleotide sequence of anti-Lysozyme clone D56

CCCCGAGAACCACAGGTGTACACCCTGCCCCCATCCCGTGACGAGCTCTGCGTCCCGCAAGTCA
GCCTGACCTGCCTGGTCAAAGGCTTCTATCCCAGCGACATCGCCGTGGAGTGGGAGAGCAATGG
GCAGCCGGAGAACAACTACAAGACCACGCCTCCCGTGCTGGACTCCGACGGCTCCTTCTTCCTCT

Fig. 8 continued

ACAGCAAGCTTACCGTGGTGCTCAAGGTCGTGCAGGCGCGCAGGTGGGAGGTGGGGAACGTCTT
CTCATGCTCCGTGATGCATGAGGCTCTGCACAACCACTACACACAGAAGAGCCTCTCCCTGTCTC
CGGGTAAA

SEQ ID No. 34: Amino acid sequence of anti-TLR9 clone A23
PREPQVYTLPPSRDELGIAQVSLTCLVKGFYPSDIAVEWESNGQPENNYKTTPPVLDSDGSFFLYSKLT
VLGRRWTLGNVFSCSVMHEALHNHYTQKSLSLSPGK SEQ ID No. 35: Nucleotide sequence of anti-TLR9 clone A23
CCCCGAGAACCACAGGTGTACACCCTGCCCCCATCCCGGGACGAGCTCGGCATCGCGCAAGTCA
GCCTGACCTGCCTGGTCAAAGGCTTCTATCCCAGCGACATCGCCGTGGAGTGGGAGAGCAACGG
GCAGCCGGAGAACAACTACAAGACCACGCCTCCCGTGCTGGACTCCGACGGCTCTTTCTTCCTCT
ACAGCAAGCTTACCGTGTTGGGCCGCAGGTGGACCCTGGGGAACGTCTTCTCATGCTCCGTGATG
CATGAGGCTCTGCACAACCACTACACACAGAAGAGCCTCTCCCTGTCTCCGGGTAAA SEQ ID No. 36: Amino acid sequence of anti-TLR9 clone A33
PREPQVYTLPPSRDELGIAQVSLTCLVKGFYPSDIAVEWESNGQPENNYKTTPPVLDSDGSFFLYSKLT
VLGRRWTLGNVFSCSVMHEALHNHYTQKSLSLSPGK SEQ ID No. 37: Nucleotide sequence of anti-TLR9 clone A33
CCCCGAGAACCACAGGTGTACACCCTGCCCCCATCCCGTGACGAGCTCGGCATCGCGCAAGTCA
GCTTGACCTGCCTGGTCAAAGGCTTTTATCCCAGCGACATCGCCGTGGAGTGGGAGAGCAACGG
GCAGCCGGAGAACAACTACAAGACCACGCCTCCCGTGCTGGACTCCGACGGCTCCTTCTTCCTCT
ACAGCAAGCTTACCGTGTTGGGCCGCAGGTGGACCCTGGGGAACGTCTTCTCATGCTCCGTGATG
CATGAGGCTCTGCACAACCACTACACACAGAAGAGCCTCTCCCTGTCTCCGGGTAAA SEQ ID No. 38: Amino acid sequence of anti-TLR9 clone D2
PREPQVYTLPPSRDELLPCQVSLTCLVKGFYPSDIAVEWESNGQPENNYKTTPPVLDSDGSFFLYSKLT
VFCPRWLGGNVFSCSVMHEALHNHYTQKSLSLSPGK

Fig. 8 continued

SEQ ID No. 39: Nucleotide sequence of anti-TLR9 clone D2

CCCCGAGAACCACAGGTGTACACCCTGCCCCCATCCCGTGACGAGCTCTTGCCCTGCCAAGTCAG
CCTGACCTGCCTGGTCAAAGGCTTCTATCCCAGCGACATCGCCGTGGAGTGGGAGAGCAATGGG
CAGCCGGAGAACAACTACAAGACCACGCCTCCCGTGCTGGACTCCGACGGCTCTTTCTTCCTCTA
CAGCAAGCTTACCGTGTTCTGCCCCAGGTGGCTGGGGGGAACGTCTTCTCATGCTCCGTGATGC
ATGAGGCTCTGCACAACCACTACACACAGAAGAGCCTCTCCCTGTCTCCGGGTAAA

SEQ ID No. 40: Amino acid sequence of anti-TLR9 clone D68

PREPQVYTLPPSRDEL<u>TKN</u>QVSLTCLVKGFYPSDIAVEWESNGQPENNYKTTPPVLDSDGSFFLYSKLT
VP<u>CMR</u>W<u>W</u>GGNVFSCSVMHEALHNHYTQKSLSLSPGK

SEQ ID No. 41: Nucleotide sequence of anti-TLR9 clone D68

CCCCGAGAACCACAGGTGTACACCCTGCCCCCATCCCGGGATGAGCTGACCAAGAACCAGGTCA
GCCTGACCTGCCTGGTCAAAGGCTTCTATCCCAGCGACATCGCCGTGGAGTGGGAGAGCAATGG
GCAGCCGGAGAACAACTACAAGACCACGCCTCCCGTGCTGGACTCCGACGGCTCCTTCTTCCTCT
ACAGCAAGCTTACCGTGCCCTGCATGAGGTGGTGGGGCGGGAACGTCTTCTCATGCTCCGTGATG
CATGAGGCTCTGCACAACCACTACACACAGAAGAGCCTCTCCCTGTCTCCGGGTAAA

SEQ ID No. 42: Amino acid sequence of bispecific CH3 domain, mutated on both sides, binding to lysozyme and to Erythropoietin, clone D72

<u>R</u>REPQVYTLPPSRDEL<u>VLG</u>QVSLACLVKGF<u>VVRL</u>IAVEWESNGQPENNYKTTPPVLDSDG<u>RQLAD</u>SFF
LYSKLTV<u>PPRLKGWPR</u>W<u>GW</u>GNVFSCSVM<u>FLA</u>LHNHYTQKSLSLSPGK

Fig. 8 continued

SEQ ID No. 43: Nucleotide sequence of bispecific CH3 domain, mutated on both sides, binding to lysozyme and to Erythropoietin, clone D72

CGGCGAGAACCACAGGTGTACACCCTGCCCCCATCCCGTGACGAGCTCGTCTTGGGGCAAGTCA
GCCTGGCCTGCCTCGTGAAAGGCTTCGTGGTCCGGTTGATCGCCGTGGAGTGGGAGAGCAATGG
GCAGCCGGAGAACAACTACAAGACCACGCCTCCCGTTCTAGACTCCGACGGCCGGCAGTTGGCG
GACTCCTTCTTCCTCTACAGCAAGCTTACCGTGCCCCGCGGTTGAAGGGCTGGCCGAGGTGGG
GCTGGGGGAACGTCTTCTCATGCAGTGTGATGTTCCTGGCGCTGCACAACCACTACACACAGAAG
AGCCTCTCCCTGTCTCCGGGTAAA

SEQ ID No. 44: Amino acid sequence of bivalent Fab-like construct, consisting of VH and VL from anti-HIV1-gp41 antibody 3D6 and anti-Lysozyome clone C24 (3D6-VH – C24)

EVQLVESGGGLVQPGRSLRLSCAASGFTFNDYAMHWVRQAPGKGLEWVSGISWDSSSIGYADSVKG
RFTISRDNAKNSLYLQMNSLRAEDMALYYCVKGRDYYDSGGYFTVAFDIWGQGTMVTVSSASTKGPQ
VYTLPPSRDEL<u>VL</u>GQVSPTCLVKGFYPSDIAVEWESNGQPENNYKTTPPVLDSDGSFFLYGKLTV<u>PPRL
KGWPRW</u><u>GW</u>GNVFSCSVMHEALHNHYTQKSLSLSPGK

SEQ ID No. 45: Nucleotide sequence of bivalent Fab-like construct, consisting of VH and VL from anti-HIV1-gp41 antibody 3D6 and anti-Lysozyome clone C24 (3D6-VH – C24)

GAAGTGCAGCTGGTGGAGTCTGGGGGAGGCTTGGTACAGCCTGGCAGGTCCCTGAGACTCTCCT
GTGCAGCCTCTGGATTCACCTTTAATGATTATGCCATGCACTGGGTCCGGCAAGCTCCAGGGAAG
GGCCTGGAGTGGGTCTCAGGTATAAGTTGGGATAGTAGTAGTATAGGCTATGCGGACTCTGTGAA
GGGCCGATTCACCATCTCCAGAGACAACGCCAAGAACTCCCTGTATCTGCAAATGAACAGTCTGA
GAGCTGAGGACATGGCCTTATATTACTGTGTAAAAGGCAGAGATTACTATGATAGTGGTGGTTATT
TCACGGTTGCTTTTGATATCTGGGGCCAAGGGACAATGGTCACCGTCTCTTCAGCCTCCACCAAG
GGCCCACAGGTGTACACCCTGCCCCCATCCCGTGACGAGCTCGTCTTGGGGCAAGTCAGCCCGA
CCTGCCTGGTCAAAGGCTTCTATCCCAGCGACATCGCCGTGGAGTGGGAGAGCAATGGGCAGCC
GGAGAACAACTACAAGACCACGCCTCCCGTGCTGGACTCCGACGGCTCCTTCTTCCTCTACGGCA
AGCTTACCGTGCCCCGCGGTTGAAGGGCTGGCCGAGGTGGGGCTGGGGGAACGTCTTCTCATG
CTCCGTGATGCATGAGGCTCTGCACAACCACTACACACAGAAGAGCCTCTCCCTGTCTCCGGGTA
AA

Fig. 8 continued

SEQ ID No. 46: Amino acid sequence of bivalent Fab-like construct, consisting of VH and VL from anti-HIV1-gp41 antibody 3D6 and anti-Lysozyome clone C24 (3D6-VL – C24)

DIQMTQSPSTLSASVGDRVTITCRASQSISRWLAWYQQKPGKVPKLLIYKASSLESGVPSRFSGSGSGT
EFTLTISSLQPDDFATYYCQQYNSYSFGPGTKVDIKRTVAEPQVYTLPPSRDELVLGQVSPTCLVKGFY
PSDIAVEWESNGQPENNYKTTPPVLDSDGSFFLYGKLTVPPRLKGWPRWGWGNVFSCSVMHEALHN
HYTQKSLSLSPGK

SEQ ID No. 47: Nucleotide sequence of bivalent Fab-like construct, consisting of VH and VL from anti-HIV1-gp41 antibody 3D6 and anti-Lysozyome clone C24 (3D6-VL – C24)

GACATCCAGATGACCCAGTCTCCTTCCACCCTGTCTGCATCTGTAGGAGACAGAGTCACCATCACT
TGCCGGGCCAGTCAGAGTATTAGTAGGTGGTTGGCCTGGTATCAGCAGAAACCAGGGAAAGTCCC
TAAGCTCCTGATCTATAAGGCATCTAGTTTAGAAAGTGGGGTCCCATCAAGGTTCAGCGGCAGTGG
ATCTGGGACAGAATTCACTCTCACCATCAGCAGCCTGCAGCCTGATGATTTTGCAACTTATTACTG
CCAACAGTATAATAGTTATTCTTTCGGCCCTGGGACCAAAGTGGATATCAAACGAACTGTGGCTGA
ACCACAGGTGTACACCCTGCCCCCATCCCGTGACGAGCTCGTCTTGGGGCAAGTCAGCCCGACC
TGCCTGGTCAAAGGCTTCTATCCCAGCGACATCGCCGTGGAGTGGGAGAGCAATGGGCAGCCGG
AGAACAACTACAAGACCACGCCTCCCGTGCTGGACTCCGACGGCTCCTTCTTCCTCTACGGCAAG
CTTACCGTGCCCCCGCGGTTGAAGGGCTGGCCGAGGTGGGGCTGGGGGAACGTCTTCTCATGCT
CCGTGATGCATGAGGCTCTGCACAACCACTACACACAGAAGAGCCTCTCCCTGTCTCCGGGTAAA

SEQ ID No. 48: Amino acid sequence of CL Library

1   MKYLLPTAAAGLLLLAAQPAMAVAAPSVFIFPPSXXQXXXXXASVVCLLN
51  NFYPREAKVQWKVDNALQSGNSQESVTEQDSKDSTYSLSSTLTLXXXXYE
101 KHKVYACEVTHQGLSSPVTKSFNRGEAAA

SEQ ID No. 49: Nucleotide sequence of CL Library

1   ATGAAATACCTATTGCCTACGGCAGCCGCTGGATTGTTATTACTCGCGGC
51  CCAGCCGGCCATGGCCGTGGCTGCACCATCTGTCTTCATCTTCCCGCCAT
101 CTNNSNNSCAGNNSNNSNNSNNSNNSGCCTCTGTTGTGTGCCTGCTGAAT
151 AACTTCTATCCCAGAGAGGCCAAAGTACAGTGGAAGGTGGATAACGCCCT

Fig. 8 continued

201 CCAATCGGGTAACTCCCAGGAGAGTGTCACAGAGCAGGACAGCAAGGACA
251 GCACCTACAGCCTCAGCAGCACCCTGACGTTGNNSNNSNNSNNSTACGAG
301 AAACACAAAGTCTACGCCTGCGAAGTCACCCATCAGGGCCTGAGCTCGCC
351 CGTCACAAAGAGCTTCAACAGGGGAGAGGCGGCCGCA

SEQ ID No. 50: Amino acid sequence of CL+3 Library

1 MKYLLPTAAAGLLLLAAQPAMAVAAPSVFIFPPSXXQXXXXXASVVCLLN
51 NFYPREAKVQWKVDNALQSGNSQESVTEQDSKDSTYSLSSTLTLXXXXXX
101 XYEKHKVYACEVTHQGLSSPVTKSFNRGEAAA

SEQ ID No. 51: Nucleotide sequence of CL+3 Library

1 ATGAAATACCTATTGCCTACGGCAGCCGCTGGATTGTTATTACTCGCGGC
51 CCAGCCGGCCATGGCCGTGGCTGCACCATCTGTCTTCATCTTCCCGCCAT
101 CTNNSNNSCAGNNSNNSNNSNNSNNSGCCTCTGTTGTGTGCCTGCTGAAT
151 AACTTCTATCCCAGAGAGGCCAAAGTACAGTGGAAGGTGGATAACGCCCT
201 CCAATCGGGTAACTCCCAGGAGAGTGTCACAGAGCAGGACAGCAAGGACA
251 GCACCTACAGCCTCAGCAGCACCCTGACGTTGNNSNNSNNSNNSNNSNNS
301 NNSTACGAGAAACACAAAGTCTACGCCTGCGAAGTCACCCATCAGGGCCT
351 GAGCTCGCCCGTCACAAAGAGCTTCAACAGGGGAGAGGCGGCCGCA

SEQ ID No. 52: Amino acid sequence of CL+5 Library

1 MKYLLPTAAAGLLLLAAQPAMAVAAPSVFIFPPSXXQXXXXXASVVCLLN
51 NFYPREAKVQWKVDNALQSGNSQESVTEQDSKDSTYSLSSTLTLXXXXXX
101 XXXYEKHKVYACEVTHQGLSSPVTKSFNRGEAAA

SEQ ID No. 53: Nucleotide sequence of CL+5 Library

1 ATGAAATACCTATTGCCTACGGCAGCCGCTGGATTGTTATTACTCGCGGC
51 CCAGCCGGCCATGGCCGTGGCTGCACCATCTGTCTTCATCTTCCCGCCAT
101 CTNNSNNSCAGNNSNNSNNSNNSNNSGCCTCTGTTGTGTGCCTGCTGAAT
151 AACTTCTATCCCAGAGAGGCCAAAGTACAGTGGAAGGTGGATAACGCCCT

Fig. 8 continued

201 CCAATCGGGTAACTCCCAGGAGAGTGTCACAGAGCAGGACAGCAAGGACA

251 GCACCTACAGCCTCAGCAGCACCCTGACGTTGNNSNNSNNSNNSNNSNNS

301 NNSNNSNNSTACGAGAAACACAAAGTCTACGCCTGCGAAGTCACCCATCA

351 GGGCCTGAGCTCGCCCGTCACAAAGAGCTTCAACAGGGGAGAGGCGGCCG

401 CA

SEQ ID No. 54: Amino acid sequence of CH Library

1   MKYLLPTAAAGLLLLAAQPAMAASTKGPSVFPLAPSSXXXXXXXXXALGCL

51  VKDYFPEPVTVSWNSGALTSGVHTFPAVLQSSGLYSLSSVVTVPXXXXXX

101 XTYICNVNHKPSNTKVDKKVEPKSAAA

SEQ ID No. 55: Nucleotide sequence of CH Library

1   ATGAAATACCTATTGCCTACGGCAGCCGCTGGATTGTTATTACTCGCGGC

51  CCAGCCGGCCATGGCCGCCTCCACCAAGGGCCCATCGGTCTTCCCCCTGG

101 CACCCTCCTCCNNSNNSNNSNNSNNSNNSNNSGCCCTGGGCTGCCTG

151 GTCAAGGACTACTTCCCCGAACCGGTGACGGTGTCGTGGAACTCAGGCGC

201 CCTGACCAGCGGCGTGCACACCTTCCCGGCTGTCCTACAGTCCTCAGGAC

251 TCTACTCCCTCAGCAGCGTGGTGACCGTGCCCNNSNNSNNSNNSNNS

301 NNSACCTACATCTGCAACGTGAATCACAAGCCCAGCAACACCAAGGTGGA

351 CAAGAAAGTTGAGCCCAAATCTGCGGCCGCA

SYNTHETIC IMMUNOGLOBULIN DOMAINS WITH BINDING PROPERTIES ENGINEERED IN REGIONS OF THE MOLECULE DIFFERENT FROM THE COMPLEMENTARITY DETERMINING REGIONS

CROSS REFERENCE TO RELATED APPLICATIONS

This application is a continuation of U.S. patent application Ser. No. 13/149,871 filed on Feb. 2, 2012, which is a continuation of U.S. patent application Ser. No. 11/722,517, filed on Jun. 21, 2007, which is the U.S. national phase under 35 U.S.C. § 371 of PCT International Application No. PCT/EP2006/050059, filed on Jan. 5, 2006, which claims the benefit of priority under 35 U.S.C. 119(e) to U.S. Provisional Patent Application No. 60/641,144, filed on Jan. 5, 2005. The entire contents of the foregoing patent applications are incorporated herein by reference in their entireties.

INCORPORATION-BY-REFERENCE OF MATERIAL SUBMITTED ELECTRONICALLY

The entire contents of a Sequence Listing titled 3906_1036_seq_listing," created on Mar. 31, 2017 and having a size of 64 kilobytes, is being filed herewith in electronic form in connection with the present application, and is hereby incorporated by reference in its entirety.

FIELD OF THE INVENTION

The present invention relates to libraries of immunoglobulins which each have one or more amino acid modifications in at least one structural loop region of such immunoglobulins, wherein the modified loop region specifically binds to an epitope of an antigen to which an unmodified immunoglobulin does not significantly bind.

BACKGROUND OF THE INVENTION

The general field is the engineering of proteins with the aim to impart them with specific binding properties. More specifically, the engineered proteins of relevance here are immunoglobulins (antibodies), and even more specifically, single domains or pairs or combinations of single domains of immunoglobulins. The specific binding properties of immunoglobulins are important features since they control the interaction with other molecules such as antigens, and render immunoglobulins useful for diagnostic and therapeutic applications.

The basic antibody structure will be explained here using as example an intact IgG1 immunoglobulin.

Two identical heavy (H) and two identical light (L) chains combine to form the Y-shaped antibody molecule. The heavy chains each have four domains. The amino terminal variable domains (VH) are at the tips of the Y. These are followed by three constant domains: CH1, CH2, and the carboxy terminal CH3, at the base of the Y's stem. A short stretch, the switch, connects the heavy chain variable and constant regions. The hinge connects CH2 and CH3 (the Fc fragment) to the remainder of the antibody (the Fab fragments). One Fc and two identical Fab fragments can be produced by proteolytic cleavage of the hinge in an intact antibody molecule. The light chains are constructed of two domains, variable (VL) and constant (CL), separated by a switch.

Disulfide bonds in the hinge region connect the two heavy chains. The light chains are coupled to the heavy chains by additional disulfide bonds. Asn-linked carbohydrate moieties are attached at different positions in constant domains depending on the class of immunoglobulin. For IgG1 two disulfide bonds in the hinge region, between Cys235 and Cys238 pairs, unite the two heavy chains. The light chains are coupled to the heavy chains by two additional disulfide bonds, between Cys229s in the CH1 domains and Cys214s in the CL domains. Carbohydrate moieties are attached to Asn306 of each CH2, generating a pronounced bulge in the stem of the Y.

These features have profound functional consequences. The variable regions of both the heavy and light chains (VH) and (VL) lie at the "tips" of the Y, where they are positioned to react with antigen. This tip of the molecule is the side on which the N-terminus of the amino acid sequence is located. The stem of the Y projects in a way to efficiently mediate effector functions such as the activation of complement and interaction with Fc receptors, or ADCC and ADCP. Its CH2 and CH3 domains bulge to facilitate interaction with effector proteins. The C-terminus of the amino acid sequence is located on the opposite side of the tip, which can be termed "bottom" of the Y. The structure of an intact IgG1 is illustrated in FIG. 1a.

Two types of light chain, termed lambda (λ) and kappa (κ), are found in antibodies. A given immunoglobulin either has κ chains or λ chains, never one of each. No functional difference has been found between antibodies having λ or κ light chains.

Figure 1B:
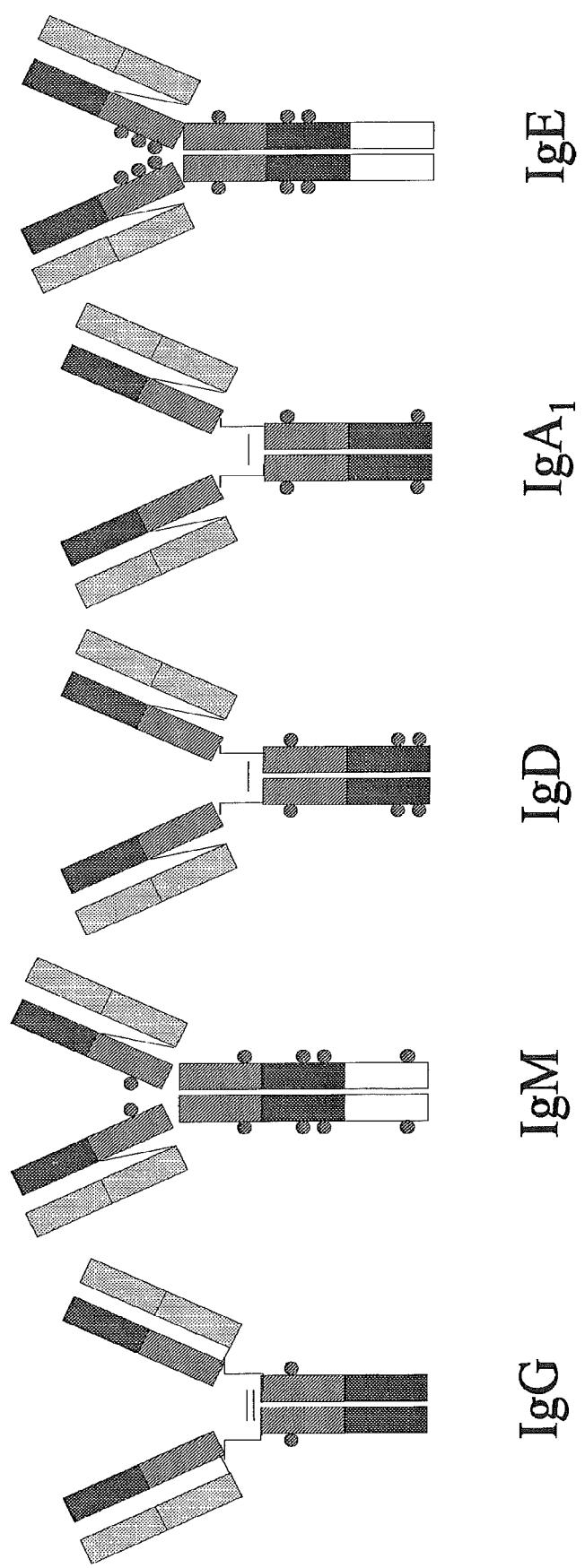

The structural organization of the main human immunoglobulin class monomers is shown in FIG. 1b. The classes differ in the composition and sequence of their respective heavy chains. Both IgM and IgE lack a hinge region but each contains an extra heavy-chain domain (CH4). Numbers and locations of the disulfide bonds (lines) linking the chains differ between the isotypes. They also differ in the distribution of N-linked carbohydrate groups, symbolically shown as circles.

Each domain in an antibody molecule has a similar structure of two beta sheets packed tightly against each other in a compressed antiparallel beta barrel. This conserved structure is termed the immunoglobulin fold. The immunoglobulin fold of constant domains contains a 3-stranded sheet packed against a 4-stranded sheet. The fold is stabilized by hydrogen bonding between the beta strands of each sheet, by hydrophobic bonding between residues of opposite sheets in the interior, and by a disulfide bond between the sheets. The 3-stranded sheet comprises strands C, F, and G, and the 4-stranded sheet has strands A, B, E, and D. The letters A through G denote the sequential positions of the beta strands along the amino acid sequence of the immunoglobulin fold.

Figure 2:
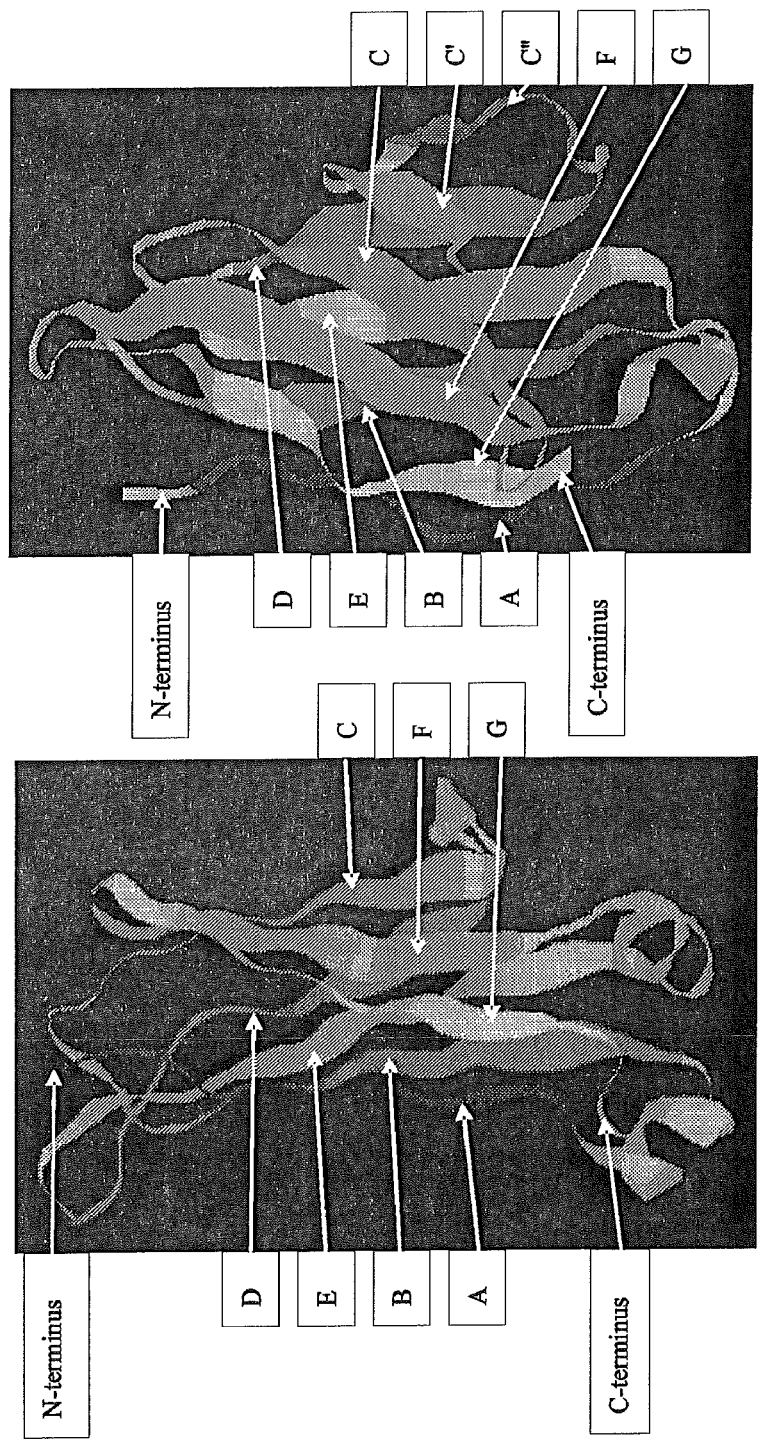

The fold of variable domains has 9 beta strands arranged in two sheets of 4 and 5 strands. The 5-stranded sheet is structurally homologous to the 3-stranded sheet of constant domains, but contains the extra strands C' and C". The remainder of the strands (A, B, C, D, E, F, G) have the same topology and similar structure as their counterparts in constant domain immunoglobulin folds. A disulfide bond links strands B and F in opposite sheets, as in constant domains. The immunoglobulin fold is illustrated in FIG. 2 for a constant and a variable domain of an immunoglobulin.

The variable domains of both light and heavy immunoglobulin chains contain three hypervariable loops, or complementarity-determining regions (CDRs). The three CDRs of a V domain (CDR1, CDR2, CDR3) cluster at one end of the beta barrel. The CDRs are loops that connect beta strands B-C, C'-C", and F-G of the immunoglobulin fold. The residues in the CDRs vary from one immunoglobulin molecule to the next, imparting antigen specificity to each antibody.

The VL and VH domains at the tips of antibody molecules are closely packed such that the 6 CDRs (3 on each domain) cooperate in constructing a surface (or cavity) for antigen-specific binding. The natural antigen binding site of an antibody thus is composed of the loops which connect strands B-C, C'-C", and F-G of the light chain variable domain and strands B-C, C'-C", and F-G of the heavy chain variable domain.

Using the 3D structure of a protein as an aid for design, amino acid residues located on the surface of many proteins have been randomized using the core structure of the protein as scaffold. Examples for this strategy are described or reviewed in the following references incorporated herein by reference: Nygren P A, Uhlen M., Curr Opin Struct Biol. (1997) 7:463-9; Binz H K, Amstutz P, Kohl A, Stumpp M T, Briand C, Forrer P, Grutter M G, Pluckthun A. Nat Biotechnol. (2004) 22:575-82; Vogt M, Skerra A. Chembiochem. (2004) 5:191-9; U.S. Pat. No. 6,562,617.

The basic principle of this technique is based on the observation that many proteins have a stable core, formed by specific arrangements of secondary structure elements such as beta sheets or alpha helices, which are interconnected by structures such as loops, turns, or random coils. Typically, these latter three structure elements are less crucial for the overall structure of the protein, and amino acid residues in these structure elements can be exchanged often without destroying the general fold of the protein. A naturally occurring example for this design principle are the CDRs of antibodies. Artificial examples include lipocalins, ankyrins and other protein scaffolds.

The loops which are not CDR-loops in a native immunoglobulin do not have antigen binding or epitope binding specificity but contribute to the correct folding of the entire immunoglobulin molecule and/or its effector or other functions and are therefore called structural loops for the purpose of this invention.

In U.S. Pat. No. 6,294,654 it is shown that altered antibodies can be made in which a peptide antigen can be incorporated into a non-CDR loop of an antibody (Ab) in the CH1 region between the hinge region and the variable region, and the resulting Ab can be taken up in an APC so that the peptide antigen is presented on the surface of the APC in the context of MHC II, and thereby produce an immune response. These inserted peptides are epitopes and the overall structure of the carrier molecule is not important. It was demonstrated that a ras peptide can be placed on a (non-CDR) loop of an Immunoglobulin and the Immunoglobulin still be secreted. There is stringent "quality control" in the cells which prevent the Immunoglobulin from being secreted unless it is properly folded, and altering the amino acid sequence of the loop might cause the protein to fold into a structure which the cell would detect as incorrect, and hence degrade it. Thus, besides the examples shown it was considered to be difficult to further modify the structural loops without changing the nature of the Immunoglobulin.

US Pat Appl 2004/0101905 describes binding molecules comprising a target binding site and a Fc effector peptide. The Fc effector peptide is a peptide which interacts with effector molecule. The insertion of an effector peptide into a non-CDR loop of a CH1-domain of an immunoglobulin fragment has been shown.

Fc effector peptides are structures which are naturally occurring in non-CDR loops of antibodies and are therefore expected not to disturb the structure of the immunoglobulin if grafted to onto different equivalent locations in an immunoglobulin.

Nevertheless every peptide grafted into a non-CDR loop according to this disclosure has a high chance of being inactive by the different structural environment it has been selected.

It is stated in both prior art documents mentioned above that it is difficult to insert peptides into the loop that should retain its structure and function, as it is critical not to disturb the immunoglobulin folding structure as this is important for function and secretion.

US Patent Applications 2004/0132101 and 2005/0244403 describe mutant immunoglobulins with altered binding affinity to an effector ligand, which are natural ligands for structural loops of antibodies. In this document a number of mutations in various regions across the entire immunoglobulin molecule are described which influence the effector function of the entire antibody.

Other prior art documents show that the immunoglobulin like scaffold has been employed so far for the purpose of manipulating the existing antigen binding site, thereby introducing novel binding properties. So far however, only the CDR regions have been engineered for antigen binding, in other words, in the case of the immunoglobulin fold, only the natural antigen binding site has been modified in order to change its binding affinity or specificity. A vast body of literature exists which describes different formats of such manipulated immunoglobulins, frequently expressed in the form of single-chain Fv fragments (scFv) or Fab fragments, either displayed on the surface of phage particles or solubly expressed in various prokaryotic or eukaryotic expression systems. Among the leading authors in the field are Greg Winter, Andreas Plückthun and Hennie Hoogenboom.

BRIEF SUMMARY OF THE INVENTION

It is an object of the present invention to provide immunoglobulins with new antigen binding sites introduced, and methods for engineering and manufacturing said immunoglobulins.

Therefore, the present invention relates to a method for engineering an immunoglobulin comprising at least one modification in a structural loop region of said immunoglobulin and determining the binding of said immunoglobulin to an epitope of an antigen, wherein the unmodified immunoglobulin does not significantly bind to said epitope, comprising the steps of:

- providing a nucleic acid encoding an immunoglobulin comprising at least one structural loop region,
- modifying at least one nucleotide residue of at least one of said structural loop regions,
- transferring said modified nucleic acid in an expression system,
- expressing said modified immunoglobulin,
- contacting the expressed modified immunoglobulin with an epitope, and
- determining whether said modified immunoglobulin binds to said epitope.

In particular, the present invention relates to a method for engineering an immunoglobulin binding specifically to an epitope of an antigen selected from the group consisting of allergens, tumor associated antigens, self antigens, enzymes, bacterial antigens, fungal antigens, protozooal antigen and viral antigens. Through the modification in the structural loop region the immunoglobulin may be engineered bind to the epitope. In a preferred embodiment the immunoglobulin is binding specifically to at least two such epitopes, that differ from each other, either of the same antigen or of different antigens.

For example, the method according to the invention refers to engineering an immunoglobulin binding specifically to at least one first epitope and comprising at least one modification in at least one structural loop region of said immunoglobulin and determining the specific binding of said at least one loop region to at least one second epitope, the epitope being selected from the group of antigens as mentioned above, wherein the unmodified structural loop region (non-CDR region) does not specifically bind to said at least one second epitope, comprising the steps of:

providing a nucleic acid encoding an immunoglobulin binding specifically to at least one first epitope comprising at least one structural loop region, modifying at least one nucleotide residue of at least one of said loop regions encoded by said nucleic acid, transferring said modified nucleic acid in an expression system, expressing said modified immunoglobulin, contacting the expressed modified immunoglobulin with said at least one second epitope, and determining whether said modified immunoglobulin binds specifically to the second epitope.

BRIEF DESCRIPTION OF THE DRAWINGS

The present invention is further illustrated in the following figures and examples without being restricted thereto.

FIG. 1*a* shows the structure of an intact IgG1. Domains are indicated with arrows.

FIG. 1*b* illustrates the structural organization of the main human immunoglobulin isotype monomers. Disulfide bonds are shown as lines, N-linked carbohydrate groups are shown as circles.

FIG. 2 shows the immunoglobulin fold for a constant (left) and a variable (right) domain of an immunoglobulin. Beta strands are indicated by arrows FIG. 3 shows a molecular model of the engineered CH3 domain according to the present invention, with the randomized part indicated by a solvent accessible surface. The surface is circled.

FIG. 4 shows a schematic presentation of the PCRs used for production of the fragments used for assembly of the mutated CH3 domain. PCR primers are indicated by arrows with their respective 5'-3' orientation, and vertical lines indicate the approximate positions of the introduced restriction sites which were used for assembly of the mutated gene. The following restriction sites are contained on the primers for ligations of the PCR fragments: CH3LNCO: NcoI; CH3LSAC and CH3CSAC: SacI; CH3CHIN and CH3RHIN: HindIII; CH3RNOT: NotI.

FIG. 5 shows some examples of how the immunoglobulin domains of the current application could be used. Randomized regions are indicated by a star symbol. Specificities of the randomized regions in one molecule can either be identical or different.

FIG. 6 shows a schematic presentation of the design of the bispecific engineered CH3 domain. Names of primers are given in boxes and arrows indicate the direction in which the primers are elongated. Boxes with sloping lines indicate the relative positions of regions that are randomized in this construct, boxes with vertical lines indicate the relative positions of regions that were introduced for generation of clone C24, and restriction sites used for the cloning procedure are given.

FIG. 7 shows a schematic presentation of the design of the bispecific engineered CH3 domain. The double stranded nucleotide sequence and its translation is shown of the basic design of the bispecific engineered CH3 domain directed to recombinant human Erythropoietin (rhEPO) and hen egg lysozyme. The gaps in the amino acid sequence encoded by the double stranded nucleotide sequence indicates randomized regions in order to generate the bispecific construct, including regions in which the sequence was randomized in order to generate the hen egg lysozyme specific clone C24. The amino acid segments intervening said gaps from left to right starting in the top row are: REPQVYTLPPSRDEL (residues 4 through 18 of SEQ ID NO:13); QVSLTCLVKGF (residues 22 through 32 of SEQ ID NO:13); IAVEWESNGQPENNYKTTPPVLDSDG (residues 37 through 62 of SEQ ID NO:13); SFFLYSKLTV (residues 63 through 72 of SEQ ID NO:13); RW residues 81 through 82 of SEQ ID NO:13; GNVFSCSVM (residues 85 through 93 of SEQ ID NO:13); and LHNHYTQKSLSLSPGKAAA (residues 97 through 115 of SEQ ID NO:13).

FIG. 8 shows the sequence listing of the sequences disclosed herein.

DETAILED DESCRIPTION OF THE INVENTION

The method according to the invention preferably refers to at least one modification in at least one structural loop region of said immunoglobulin and determining the specific binding of said at least one loop region to at least one antigen selected from the group consisting of allergens, tumor associated antigens, self antigens, enzymes, bacterial antigens, fungal antigens, viral antigens and protozooal antigens, wherein the immunoglobulin containing an unmodified structural loop region does not specifically bind to said at least one antigen.

The term "immunoglobulins" according to the present invention to be modified (as used herein the terms immunoglobulin and antibody are interchangeable) may exhibit mono- or multi-specific, or multivalent binding properties, at least two, preferably at least three specific binding sites for epitopes of e.g. antigens, effector molecules/proteins. Immunoglobulins according to the invention are also functional fragments accepted in the art, such as Fc, Fab, scFv, single chain dimers of CH/CL domains, Fv, or other derivatives or combinations of the immunoglobulins, domains of the heavy and light chains of the variable region (such as Fd, Vl, Vk, Vh) and the constant region of an intact antibody such as CH1, CH2, CH3, CH4, Cl and Ck, as well as mini-domains consisting of two beta-strands of an immunoglobulin domain connected by a structural loop.

It is understood that the term "immunoglobulin", "modified immunoglobulin" or "immunoglobulin according to the invention" includes a derivative of immunoglobulins as well. A derivative is any combination of one or more immunoglobulins of the invention and or a fusion protein in which any domain or minidomain of the immunoglobulin of the invention may be fused at any position of one or more other proteins (such as other immunoglobulins, ligands, scaffold proteins, enzymes toxins and the like). A derivative of the immunoglobulin of the invention may also be obtained by binding to other substances by various chemical techniques such as covalent coupling, electrostatic interaction, disulphide bonding etc.

The other substances bound to the immunoglobulins may be lipids, carbohydrates, nucleic acids, organic and anorganic molecules or any combination thereof (e.g. PEG, prodrugs or drugs). A derivative is also an immunoglobulin with the same amino acid sequence but made completely or partly from non-natural or chemically modified amino acids.

The engineered molecules according to the present invention will be useful as stand-alone proteins as well as fusion proteins or derivatives, most typically fused in such a way as to be part of larger antibody structures or complete antibody molecules, or parts thereof such as Fab fragments, Fc fragments, Fv fragments and others. It will be possible to use the engineered proteins to produce molecules which are monospecific, bispecific, trispecific, and maybe even carry more specificities at the same time, and it will be possible at the same time to control and preselect the valency of binding at the same time according to the requirements of the planned use of such molecules.

According to the present invention, binding regions to antigens or antigen binding sites of all kinds of allergens, tumor associated antigens, self antigens, enzymes, bacterial antigens, fungal antigens, protozooal antigen and viral antigens, may be introduced into a structural loop of a given antibody structure.

The term "antigen" according to the present invention shall mean molecules or structures known to interact or capable of interacting with the CDR-loop region of immunoglobulins. Structural loop regions of the prior art do not interact with antigens but rather contribute to the overall structure and/or to the binding to effector molecules.

The term "allergens, tumor associated antigens, self antigens, enzymes, bacterial antigens, fungal antigens, protozooal antigen and viral antigens" according to the present invention shall include all allergens and antigens capable of being recognised by an antibody structure, and fragments of such molecules (especially substructures generally referred to as "epitopes" (e.g. B-cell epitopes)), as long as they are immunologically relevant, i.e. are also recognisable by natural or monoclonal antibodies.

The term "epitope" according to the present invention shall mean a molecular structure which may completely make up a specific binding partner or be part of a specific binding partner to the binding domain or the immunoglobulin of the present invention.

Chemically, an epitope may either be composes of a carbohydrate, a peptide, a fatty acid, a anorganic substance or derivatives thereof and any combinations thereof. If an epitope is a polypeptide, it will usually include at least 3 amino acids, preferably 8 to 50 amino acids, and more preferably between about 10-20 amino acids in the peptide. There is no critical upper limit to the length of the peptide, which could comprise nearly the full length of the polypeptide sequence. Epitopes can be either linear or conformational epitopes. A linear epitope is comprised of a single segment of a primary sequence of a polypeptide chain. Linear epitopes can be contiguous or overlapping. Conformational epitopes are comprised of amino acids brought together by folding of the polypeptide to form a tertiary structure and the amino acids are not necessarily adjacent to one another in the linear sequence.

Specifically, epitopes are at least part of diagnostically relevant molecules, i.e. the absence or presence of an epitope in a sample is qualitatively or quantitatively correlated to either a disease or to the health status or to a process status in manufacturing or to environmental and food status. Epitopes may also be at least part of therapeutically relevant molecules, i.e. molecules which can be targeted by the specific binding domain which changes the course of the disease.

Preferred "allergens, tumor associated antigens, self antigens, enzymes, bacterial antigens, fungal antigens, protozooal antigen and viral antigens," are those allergens or antigens, which have already been proven to be or are capable of being immunologically or therapeutically relevant, especially those, for which a clinical efficacy has been tested.

On the other hand, according to another aspect of the present invention also other binding capacities may be introduced in the structural loop regions, e.g. binding capacities for small molecules, such as drugs or enzymes, catalytic sites of enzymes or enzyme substrates or for a transition state analog of an enzyme substrate.

Preferably the new antigen binding site in the structural loops is foreign to the unmodified immunoglobulin. Thus targets like effector molecules or Fc-receptors are preferably excluded from the binding molecules and the specificity of the immunoglobulins according to the invention.

Preferably, the new antigen binding sites in the structural loops are introduced by substitution, deletion and/or insertion of the immunoglobulin encoded by the selected nucleic acid.

According to another preferred embodiment of the present invention the modification of at least one nucleotide results in a substitution, deletion and/or insertion of the immunoglobulin encoded by said nucleic acid.

The modification of the at least one loop region may result in a substitution, deletion and/or insertion of 1 or more amino acids, preferably a point mutation, exchange of whole loops, more preferred the change of at least 2, 3, 4, 5, 6, 7, 8, 9, 10 up to 30 amino acids.

Also preferred is the site directed random mutation. With this method one or more specific amino acid residues of the loop are exchanged or introduced using randomly generated inserts into such structural loops. Alternatively preferred is the use of combinatorial approaches.

The at least one loop region is preferably mutated or modified by random, semi-random or, in particular, by site-directed random mutagenesis methods. These methods may be used to make amino acid modifications at desired positions of the immunoglobulin of the present invention. In these cases positions are chosen randomly, or amino acid changes are made using simplistic rules. For example all residues may be mutated to alanine, referred to as alanine scanning. Such methods may be coupled with more sophisticated engineering approaches that employ selection methods to screen higher levels of sequence diversity. A preferred method according to the invention refers to the randomly modified nucleic acid molecule which comprises at least one nucleotide repeating unit having the sequence 5'-NNS-3', 5'-NNN-3' or 5'-NNK-3'.

The randomly modified nucleic acid molecule may comprise the above identified repeating units, which code for all known naturally occurring amino acids.

As is well known in the art, there are a variety of selection technologies that may be used for the identification and isolation of proteins with certain binding characteristics and affinities, including, for example, display technologies such as phage display, ribosome display, cell surface display, and the like, as described below. Methods for production and screening of antibody variants are well known in the art. General methods for antibody molecular biology, expression, purification, and screening are described in Antibody Engineering, edited by Duebel & Kontermann, Springer-Verlag, Heidelberg, 2001; and Hayhurst & Georgiou, 2001, Curr Opin Chem Biol 5:683-689; Maynard & Georgiou, 2000, Annu Rev Biomed Eng 2:339-76.

A "structural loop" or "non-CDR-loop" according to the present invention is to be understood in the following manner: immunoglobulins are made of domains with a so called immunoglobulin fold. In essence, anti-parallel beta sheets are connected by loops to form a compressed anti-parallel beta barrel. In the variable region, some of the loops of the domains contribute essentially to the specificity of the antibody, i.e. the binding to an antigen. These loops are called CDR-loops. All other loops of antibody domains are rather contributing to the structure of the molecule and/or the effector function. These loops are defined herein as structural loops or non-CDR-loops.

The nucleic acid molecules encoding the modified immunoglobulins (and always included throughout the whole specification below: immunoglobulin fragments) may be cloned into host cells, expressed and assayed for their binding specificities. These practices are carried out using well-known procedures, and a variety of methods that may find use in the present invention are described in Molecular Cloning—A Laboratory Manual, 3.sup.rd Ed. (Maniatis, Cold Spring Harbor Laboratory Press, New York, 2001), and Current Protocols in Molecular Biology (John Wiley & Sons). The nucleic acids that encode the modified immunoglobulins of the present invention may be incorporated into an expression vector in order to express said immunoglobulins. Expression vectors typically comprise an immunoglobulin operably linked, that is placed in a functional relationship, with control or regulatory sequences, selectable markers, any fusion partners, and/or additional elements. The modified immunoglobulins of the present invention may be produced by culturing a host cell transformed with nucleic acid, preferably an expression vector, containing nucleic acid encoding the modified immunoglobulins, under the appropriate conditions to induce or cause expression of the modified immunoglobulins. The methods of introducing exogenous nucleic acid molecules into a host are well known in the art, and will vary with the host used. Of course, also acellular or cell free expression systems for the expression of modified immunoglobulins may be employed.

In a preferred embodiment of the present invention, the modified immunoglobulins are purified or isolated after expression. Modified immunoglobulins may be isolated or purified in a variety of ways known to those skilled in the art. Standard purification methods include chromatographic techniques, electrophoretic, immunological, precipitation, dialysis, filtration, concentration, and chromatofocusing techniques. Purification can often be enabled by a particular fusion partner. For example, antibodies may be purified using glutathione resin if a GST fusion is employed, $Ni^{+2}$ affinity chromatography if a His-tag is employed or immobilized anti-flag antibody if a flag-tag is used. For general guidance in suitable purification techniques, see Antibody Purification: Principles and Practice, 3.sup.rd Ed., Scopes, Springer-Verlag, NY, 1994. Of course, it is also possible to express the modified immunoglobulins according to the present invention on the surface of a host, in particular on the surface of a bacterial, insect or yeast cell or on the surface of phages or viruses.

Modified immunoglobulins may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label, for example an enzyme, an immune label, isotopic label, or small molecule label such as a fluorescent or colorimetric dye or a luminogenic molecule.

In a preferred embodiment, the functional and/or biophysical properties of the immunoglobulins are screened in an in vitro assay. In a preferred embodiment, the antibody is screened for functionality, for example its ability to catalyze a reaction or its binding affinity to its target.

Assays may employ a variety of detection methods including but not limited to chromogenic, fluorescent, luminescent, or isotopic labels.

As is known in the art, a subset of screening methods are those that select for favorable members of a library. The methods are herein referred to as "selection methods", and these methods find use in the present invention for screening modified immunoglobulins. When immunoglobulins libraries are screened using a selection method, only those members of a library that are favorable, that is which meet some selection criteria, are propagated, isolated, and/or observed. As will be appreciated, because only the most fit variants are observed, such methods enable the screening of libraries that are larger than those screenable by methods that assay the fitness of library members individually. Selection is enabled by any method, technique, or fusion partner that links, covalently or noncovalently, the phenotype of immunoglobulins with its genotype, that is the function of a antibody with the nucleic acid that encodes it. For example the use of phage display as a selection method is enabled by the fusion of library members to the gene III protein. In this way, selection or isolation of modified immunoglobulins that meet some criteria, for example binding affinity to the immunoglobulin's target, also selects for or isolates the nucleic acid that encodes it. Once isolated, the gene or genes encoding modified immunoglobulins may then be amplified. This process of isolation and amplification, referred to as panning, may be repeated, allowing favorable antibody variants in the library to be enriched. Nucleic acid sequencing of the attached nucleic acid ultimately allows for gene identification.

A variety of selection methods are known in the art that may find use in the present invention for screening immunoglobulin libraries. These include but are not limited to phage display (Phage display of peptides and antibodies: a laboratory manual, Kay et al., 1996, Academic Press, San Diego, Calif., 1996; Lowman et al., 1991, Biochemistry 30:10832-10838; Smith, 1985, Science 228:1315-1317) and its derivatives such as selective phage infection (Malmborg et al., 1997, J Mol Biol 273:544-551), selectively infective phage (Krebber et al., 1997, J Mol Biol 268:619-630), and delayed infectivity panning (Benhar et al., 2000, J Mol Biol 301:893-904), cell surface display (Witrrup, 2001, Curr Opin Biotechnol, 12:395-399) such as display on bacteria (Georgiou et al., 1997, Nat Biotechnol 15:29-34; Georgiou et al., 1993, Trends Biotechnol 11:6-10; Lee et al., 2000, Nat Biotechnol 18:645-648; June et al., 1998, Nat Biotechnol 16:576-80), yeast (Boder & Wittrup, 2000, Methods Enzymol 328:430-44; Boder & Wittrup, 1997, Nat Biotechnol 15:553-557), and mammalian cells (Whitehorn et al., 1995, Bio/technology 13:1215-1219), as well as in vitro display technologies (Amstutz et al., 2001, Curr Opin Biotechnol 12:400-405) such as polysome display (Mattheakis et al., 1994, Proc Natl Acad Sci USA 91:9022-9026), ribosome display (Hanes et al., 1997, Proc Natl Acad Sci USA 94:4937-4942), mRNA display (Roberts & Szostak, 1997, Proc Natl Acad Sci USA 94:12297-12302; Nemoto et al., 1997, FEBS Lett 414:405-408), and ribosome-inactivation display system (Zhou et al., 2002, J Am Chem Soc 124, 538-543).

Other selection methods that may find use in the present invention include methods that do not rely on display, such as in vivo methods including but not limited to periplasmic expression and cytometric screening (Chen et al., 2001, Nat Biotechnol 19:537-542), the antibody fragment complementation assay (Johnsson & Varshavsky, 1994, Proc Natl Acad Sci USA 91:10340-10344; Pelletier et al., 1998, Proc Natl Acad Sci USA 95:12141-12146), and the yeast two hybrid screen (Fields & Song, 1989, Nature 340:245-246) used in selection mode (Visintin et al., 1999, Proc Natl Acad Sci USA 96:11723-11728). In an alternate embodiment, selection is enabled by a fusion partner that binds to a specific sequence on the expression vector, thus linking covalently or noncovalently the fusion partner and associated Fc variant library member with the nucleic acid that encodes them. For example, PCT WO 00/22906; PCT WO 01/49058; PCT WO 02/04852; PCT WO 02/04853; PCT WO 02/08023; PCT WO 01/28702; and PCT WO 02/07466 describe such a fusion partner and technique that may find use in the present invention. In an alternative embodiment, in vivo selection can occur if expression of the antibody imparts some growth, reproduction, or survival advantage to the cell.

A subset of selection methods referred to as "directed evolution" methods are those that include the mating or breeding of favourable sequences during selection, sometimes with the incorporation of new mutations. As will be appreciated by those skilled in the art, directed evolution methods can facilitate identification of the most favourable sequences in a library, and can increase the diversity of sequences that are screened. A variety of directed evolution methods are known in the art that may find use in the present invention for screening antibody variants, including but not limited to DNA shuffling (PCT WO 00/42561 A3; PCT WO 01/70947 A3), exon shuffling (U.S. Pat. No. 6,365,377; Kolkman & Stemmer, 2001, Nat Biotechnol 19:423-428), family shuffling (Crameri et al., 1998, Nature 391:288-291; U.S. Pat. No. 6,376,246), RACHITT™ (Coco et al., 2001, Nat Biotechnol 19:354-359; PCT WO 02/06469), STEP and random priming of in vitro recombination (Zhao et al., 1998, Nat Biotechnol 16:258-261; Shao et al., 1998, Nucleic Acids Res 26:681-683), exonuclease mediated gene assembly (U.S. Pat. Nos. 6,352,842; 6,361,974), Gene Site Saturation Mutagenesis™ (U.S. Pat. No. 6,358,709), Gene Reassembly™ (U.S. Pat. No. 6,358,709), SCRATCHY (Lutz et al., 2001, Proc Natl Acad Sci USA 98:11248-11253), DNA fragmentation methods (Kikuchi et al., Gene 236:159-167), single-stranded DNA shuffling (Kikuchi et al., 2000, Gene 243:133-137), and AMEsystem™ directed evolution antibody engineering technology (Applied Molecular Evolution) (U.S. Pat. Nos. 5,824,514; 5,817,483; 5,814,476; 5,763,192; 5,723,323).

In a preferred embodiment, antibody variants are screened using one or more cell-based or in vivo assays. For such assays, purified or unpurified modified immunoglobulins are typically added exogenously such that cells are exposed to individual immunoglobulins or pools of immunoglobulins belonging to a library. These assays are typically, but not always, based on the function of the immunoglobulin; that is, the ability of the antibody to bind to its target and mediate some biochemical event, for example effector function, ligand/receptor binding inhibition, apoptosis, and the like. Such assays often involve monitoring the response of cells to the antibody, for example cell survival, cell death, change in cellular morphology, or transcriptional activation such as cellular expression of a natural gene or reporter gene. For example, such assays may measure the ability of antibody variants to elicit ADCC, ADCP, or CDC. For some assays additional cells or components, that is in addition to the target cells, may need to be added, for example serum complement, or effector cells such as peripheral blood monocytes (PBMCs), NK cells, macrophages, and the like. Such additional cells may be from any organism, preferably humans, mice, rat, rabbit, and monkey. Immunoglobulins may cause apoptosis of certain cell lines expressing the target, or they may mediate attack on target cells by immune cells which have been added to the assay. Methods for monitoring cell death or viability are known in the art, and include the use of dyes, immunochemical, cytochemical, and radioactive reagents. For example, caspase staining assays may enable apoptosis to be measured, and uptake or release of radioactive substrates or fluorescent dyes such as alamar blue may enable cell growth or activation to be monitored. In a preferred embodiment, the DELFIA® EuTDA-based cytotoxicity assay (Perkin Elmer, MA) may be used. Alternatively, dead or damaged target cells may be monitored by measuring the release of one or more natural intracellular components, for example lactate dehydrogenase. Transcriptional activation may also serve as a method for assaying function in cell-based assays. In this case, response may be monitored by assaying for natural genes or immunoglobulins which may be upregulated, for example the release of certain interleukins may be measured, or alternatively readout may be via a reporter construct. Cell-based assays may also involve the measure of morphological changes of cells as a response to the presence of modified immunoglobulins. Cell types for such assays may be prokaryotic or eukaryotic, and a variety of cell lines that are known in the art may be employed. Alternatively, cell-based screens are performed using cells that have been transformed or transfected with nucleic acids encoding the variants. That is, antibody variants are not added exogenously to the cells. For example, in one embodiment, the cell-based screen utilizes cell surface display. A fusion partner can be employed that enables display of modified immunoglobulins on the surface of cells (Witrrup, 2001, Curr Opin Biotechnol, 12:395-399).

In a preferred embodiment, the immunogenicity of the modified immunoglobulins may be determined experimentally using one or more cell-based assays. In a preferred embodiment, ex vivo T-cell activation assays are used to experimentally quantitate immunogenicity. In this method, antigen presenting cells and naive T cells from matched donors are challenged with a peptide or whole antibody of interest one or more times. Then, T cell activation can be detected using a number of methods, for example by monitoring production of cytokines or measuring uptake of tritiated thymidine. In the most preferred embodiment, interferon gamma production is monitored using Elispot assays (Schmittel et. al., 2000, J. Immunol. Meth., 24: 17-24).

The biological properties of the modified immunoglobulins of the present invention may be characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. The animals may be referred to as disease models. Therapeutics are often tested in mice, including but not limited to nude mice, SCID mice, xenograft mice, and transgenic mice (including knock-ins and knockouts). Such experimentation may provide meaningful data for determination of the potential of the antibody to be used as a therapeutic. Any organism, preferably mammals, may be used for testing. For example because of their genetic similarity to humans, monkeys can be suitable therapeutic models, and thus may be used to test the efficacy, toxicity, pharmacokinetics, or other property of the modified immunoglobulins of the present invention. Tests of the in humans are ultimately required for approval as drugs, and thus of course these experiments are contemplated. Thus the modified immunoglobulins of the present invention may be tested in humans to determine their therapeutic efficacy, toxicity, immunogenicity, pharmacokinetics, and/or other clinical properties.

The modified immunoglobulins of the present invention may find use in a wide range of antibody products. In one embodiment the antibody variant of the present invention is used for therapy or prophylaxis, for preparative or analytic use, as a diagnostic, an industrial compound or a research reagent, preferably a therapeutic. The antibody variant may find use in an antibody composition that is monoclonal or polyclonal. In a preferred embodiment, the modified immunoglobulins of the present invention are used to kill target cells that bear the target antigen, for example cancer cells. In an alternate embodiment, the modified immunoglobulins of the present invention are used to block, antagonize, or agonize the target antigen, for example by antagonizing a cytokine or cytokine receptor. In an alternately preferred embodiment, the modified immunoglobulins of the present invention are used to block, antagonize, or agonize the target antigen and kill the target cells that bear the target antigen.

In an alternately preferred embodiment, the modified immunoglobulins of the present invention are used to block, antagonize, or agonize growth factors or growth factor receptors and kill the target cells that bear or need the target antigen. In an alternately preferred embodiment, the modified immunoglobulins of the present invention are used to block, antagonize, or agonize enzymes and substrate of enzymes.

The modified immunoglobulins of the present invention may be used for various therapeutic purposes. In a preferred embodiment, an antibody comprising the modified immunoglobulins is administered to a patient to treat a specific disorder. A "patient" for the purposes of the present invention includes both humans and other animals, preferably mammals and most preferably humans. By "specific disorder" herein is meant a disorder that may be ameliorated by the administration of a pharmaceutical composition comprising a modified immunoglobulin of the present invention.

In one embodiment, a modified immunoglobulin according to the present invention is the only therapeutically active agent administered to a patient. Alternatively, the modified immunoglobulin according the present invention are administered in combination with one or more other therapeutic agents, including but not limited to cytotoxic agents, chemotherapeutic agents, cytokines, growth inhibitory agents, anti-hormonal agents, kinase inhibitors, anti-angiogenic agents, cardioprotectants, or other therapeutic agents. The modified immunoglobulins may be administered concomitantly with one or more other therapeutic regimens. For example, an antibody variant of the present invention may be administered to the patient along with chemotherapy, radiation therapy, or both chemotherapy and radiation therapy. In one embodiment, the modified immunoglobulins of the present invention may be administered in conjunction with one or more antibodies, which may or may not comprise a antibody variant of the present invention. In accordance with another embodiment of the invention, the modified immunoglobulins of the present invention and one or more other anti-cancer therapies are employed to treat cancer cells ex vivo. It is contemplated that such ex vivo treatment may be useful in bone marrow transplantation and particularly, autologous bone marrow transplantation. It is of course contemplated that the antibodies of the invention can be employed in combination with still other therapeutic techniques such as surgery.

A variety of other therapeutic agents may find use for administration with the modified immunoglobulins of the present invention. In one embodiment, the modified immunoglobulin is administered with an anti-angiogenic agent, which is a compound that blocks, or interferes to some degree, the development of blood vessels. The anti-angiogenic factor may, for instance, be a small molecule or a protein, for example an antibody, Fc fusion, or cytokine, that binds to a growth factor or growth factor receptor involved in promoting angiogenesis. The preferred anti-angiogenic factor herein is an antibody that binds to Vascular Endothelial Growth Factor (VEGF). In an alternate embodiment, the modified immunoglobulin is administered with a therapeutic agent that induces or enhances adaptive immune response, for example an antibody that targets CTLA-4. In an alternate embodiment, the modified immunoglobulin is administered with a tyrosine kinase inhibitor, which is a molecule that inhibits to some extent tyrosine kinase activity of a tyrosine kinase. In an alternate embodiment, the modified immunoglobulins of the present invention are administered with a cytokine. By "cytokine" as used herein is meant a generic term for proteins released by one cell population that act on another cell as intercellular mediators including chemokines.

Pharmaceutical compositions are contemplated wherein modified immunoglobulins of the present invention and one or more therapeutically active agents are formulated. Formulations of the antibody variants of the present invention are prepared for storage by mixing said immunoglobulin having the desired degree of purity with optional pharmaceutically acceptable carriers, excipients or stabilizers (Remington's Pharmaceutical Sciences 16th edition, Osol, A. Ed., 1980), in the form of lyophilized formulations or aqueous solutions. The formulations to be used for in vivo administration are preferably sterile. This is readily accomplished by filtration through sterile filtration membranes or other methods. The modified immunoglobulins and other therapeutically active agents disclosed herein may also be formulated as immunoliposomes, and/or entrapped in microcapsules Administration of the pharmaceutical composition comprising a modified immunoglobulin of the present invention, preferably in the form of a sterile aqueous solution, may be done in a variety of ways, including, but not limited to, orally, subcutaneously, intravenously, intranasally, intraotically, transdermally, topically (e.g., gels, salves, lotions, creams, etc.), intraperitoneally, intramuscularly, intrapulmonary (e.g., AERx™ inhalable technology commercially available from Aradigm, or Inhance™ pulmonary delivery system commercially available from Inhale Therapeutics), vaginally, parenterally, rectally, or intraocularly.

As used herein, the term "specifically binds" refers to a binding reaction which is determinative of the cognate ligand of interest in a heterogeneous population of molecules. Thus, under designated conditions (e.g. immunoassay conditions in the case of an immunoglobulin), the specified antibody binds to its particular "target" and does not bind in a significant amount to other molecules present in a sample. Comparable to CDRs of antibodies the modified structural loop regions are antigen- or molecule-binding protein moieties and not antigens as such.

The term "expression system" refers to nucleic acid molecules containing a desired coding sequence and control sequences in operable linkage, so that hosts transformed or transfected with these sequences are capable of producing the encoded proteins. In order to effect transformation, the expression system may be included on a vector; however, the relevant DNA may than also be integrated into the host chromosome.

According to a preferred embodiment of the present invention the expression system comprises a vector. Any expression vector known in the art may be used for this purpose as appropriate.

The modified immunoglobulin is preferably expressed in a host, preferably in a bacterial, a yeast, a plant cell, in an animal cell or in a plant or animal.

A wide variety of appropriate host cells may be used to express the modified immunoglobulin, including but not limited to mammalian cells (animal cells), plant cells, bacteria (e.g. *Bacillus subtilis, Escherichia coli*), insect cells, and yeast (e.g. *Pichia pastoris, Saccharomyces cerevisiae*). For example, a variety of cell lines that may find use in the present invention are described in the ATCC cell line catalog, available from the American Type Culture Collection. Furthermore, also plants and animals may be used as hosts for the expression of the immunoglobulin according to the present invention. The expression as well as the transfection vectors or cassettes may be selected according to the host used.

Of course also acellular or cell free protein expression systems may be used. In vitro transcription/translation protein expression platforms, that produce sufficient amounts of protein offer many advantages of a cell-free protein expression, eliminating the need for laborious up- and downstream steps (e.g. host cell transformation, culturing, or lysis) typically associated with cell-based expression systems.

Another aspect of the present invention relates to a method for manufacturing an immunoglobulin or a pharmaceutical preparation thereof comprising at least one modification in a structural loop region of said immunoglobulin and determining the binding of said immunoglobulin to an epitope of an antigen, wherein the unmodified immunoglobulin does not significantly bind to said epitope, comprising the steps of:
providing a nucleic acid encoding an immunoglobulin comprising at least one loop region,
- modifying at least one nucleotide residue of at least one of said loop regions,
- transferring said modified nucleic acid in an expression system,
- expressing said modified immunoglobulin,
- contacting the expressed modified immunoglobulin with an epitope,
- determining whether said modified immunoglobulin binds to said epitope, and
- providing the modified immunoglobulin binding to said epitope and optionally finishing it to a pharmaceutical preparation.

In particular the present invention relates to a method for manufacturing a multi-specific immunoglobulin binding specifically to at least one first molecule or a pharmaceutical preparation thereof comprising at least one modification in at least one structural loop region of said immunoglobulin and determining the specific binding of said at least one loop region to at least one second molecule selected from the group consisting of allergens, tumor associated antigens, self antigens, enzymes, bacterial antigens, fungal antigens, protozooal antigens and viral antigens, wherein the immunoglobulin containing an unmodified structural loop region does not specifically bind to said at least one second molecule, comprising the steps of:

- providing a nucleic acid encoding an immunoglobulin binding specifically to at least one first molecule comprising at least one structural loop region,
- modifying at least one nucleotide residue of at least one of said loop regions encoded by said nucleic acid,
- transferring said modified nucleic acid in an expression system,
- expressing said modified immunoglobulin,
- contacting the expressed modified immunoglobulin with said at least one second molecule, and
- determining whether said modified immunoglobulin binds specifically to the second molecule and
- providing the modified immunoglobulin binding specifically to said at least one second molecule and optionally finishing it to a pharmaceutical preparation.

The engineering of more than one specificity into a member of a specific binding pair is preferred (Kufer et al. (2004) Trends in Biotechnology vol. 22 pages 238-244).

Numerous attempts have been made to produce multi-specific, e.g. bispecific, monoclonal antibodies or antibody fragments. One problem in the production of bispecific antibodies made of two different polypeptide chains (heavy and light chain) is the necessity to express four different chains (two heavy and two light chains) in one cell resulting in a number of various combinations of molecules which have to be separated from the desired bispecific molecule in the mixture. Due to their similarity the separation of these molecules is difficult and expensive. A number of techniques have been employed to minimize the occurrence of such unwanted pairings (Carter (2001) Journal of Immunological Methods, vol 248, pages 7-15)

One solution to the problem is the production of one polypeptide chain with two specificities, like e.g. two scFvs linked to each other or the production of so-called diabodies. Such molecules have been shown to be far away from the fold of a natural molecule and are notoriously difficult to produce (LeGall et al. (2004) Protein Engineering, Design & Selection vol 17 pages 357-366).

Another problem of the current design of bispecific antibodies is the fact that even if the parent antibodies are bi-valently binding to their respective binding partner (e.g. IgG), the resulting bispecific antibody is monovalent for each of the respective binding partner.

The preferred multi-specific molecules of the present invention solve these problems:

Expression of a bispecific molecule as one polypeptide chain is possible (a modified Ig domain with two binding specificities, see example section), which is easier to accomplish than the expression of two antibody polypeptide chains (Cabilly et al. Proc. Natl. Acad. Sci. USA 81:3273-3277 (1984)).

It can also be produced as an antibody like molecule (i.e. made of 2 polypeptide chains), due to the fact that the second specificity is located in the non-variable part of the molecule there is no need for two different heavy chains or different light chains. Thus, there is no possibility of wrong pairing of the two chains.

An antibody of the present invention may consist of a heavy chain and a light chain, which form together a variable region binding to a specific binding partner the second specificity may be formed by a modified loop of any of the structural loops of either the heavy chain or the light chain. The binding site may also be formed by more than one non-CDR loop which may be structurally neighboured (either on the heavy chain or on the light chain or on both chains).

The modified antibody or derivative may be a complete antibody or an antibody fragment (e.g. Fab, CH1-CH2, CH2-CH3).

It may bind mono- or multi-valently to binding partners or even with different valency for the different binding partners, depending on the design.

As there are a number of various loops available for selection and design of a specific binding site in the non-CDR regions of heavy and light chains it is possible to design antibody derivatives with even more than two specificities without the problems mentioned above.

The specific binding domains within one polypeptide chain may be connected with or without a peptide linker.

Some antibody classes can be regarded as multi-specific, in particular bispecific, by nature: They bind to an antigen (which is typically e.g. either a foreign structure or a cancer associated structure) with the variable region and bind to Fc-effector molecules with the Fc part (e.g. Fc receptors on various immune cells or complement protein) thus enabling effects such as ADCC, ADCP or CDC.

The Fc-effector molecules are bound by the Fc-part of an immunoglobulin molecule (for IgG1 it consists of domains CH2 and CH3) and a number of methods have been described to optimize effector function by improvement of binding of the Fc-part of an antibody molecule either by glycoengineering techniques (U.S. Pat. No. 6,602,684) or by protein engineering either directly at the Fc (US 2005/0054832) or indirectly by engineering outside the Fc (US 2005/02444403). Both, binding of the Fc region to Fc receptor and/or binding to complement proteins such Cq1 has been altered by such techniques. Usually the binding affinity to such Fc-effector molecules is seeked to improve as this correlates with improved effector functions.

With the current invention it is possible to design antibody binding to Fc-effector molecules outside the natural Fc binding region. Modified loops in antibody domains other than the loops involved in "natural" Fc-effector molecule binding can be selected from a library or designed to bind to one ore more Fc-effector molecule. An antibody with such additional Fc-effector molecule binding sites would either have stronger avidity to a certain Fc-effector molecule or effector-cell displaying an Fc-effector molecule and therefore may have an even stronger effect than glycoengineered antibodies or otherwise improved Fc regions. However, for certain embodiments of the present invention, the effector characteristics of a given antibody to be modified should not directly be changed but remain unaffected by the modification in the structural loop according to the present invention.

Antibody fragments have certain advantages as compared to whole antibodies. Fragments have usually good biodistribution properties and can more easily be produced. However, most of the antibody fragment designs lack effector functions and have short in vivo half life (Holliger P, et al. Nat Biotechnol. (2005) 23:1126-36.).

Neither CH1 nor Cκ or Cλ domains mediate effector functions which is the reason why Fabs do not show ADCC, ADCP or CDC. The WO 02/44215 describes binding molecules which consists of the antigen binding site of an antibody and a peptide binding Fc-effector molecules. In such a way an antibody fragment displaying effector functions can be constructed. The peptide is being incorporated into the binding molecule at a position that does neither destroy the antigen binding nor the ability of the peptide to bind to an Fc-effector molecule.

According to the present invention however, the binding to Fc-effector molecules may be performed with modified immunoglobulin domains which have been selected for Fc-effector molecule binding from libraries of random loop sequences within a fixed scaffold of an immunoglobulin domain. Therefore, it is possible to select for specific loop sequences which would not bind to Fc-effector molecules outside the Ig-domain scaffold. The polypeptides resulting from the present invention may therefore preferably consist of more than 100 amino acids.

In order to select for potential effector function of such domains according to the present invention, libraries of mutant CH1, Cκ or Cλ domains may be selected for binding to Fc-receptors and/or complement factors such as C1q.

In order to increase in vivo half life of a molecule consisting of or containing such a domain (e.g. CH1, CH2, CH3, CH4, Cκ or Cλ), binding to FcRn may be selected for with libraries of mutant e.g. CH1-, CH2-, CH3-, CH4-, Cκ- or Cλ-domains according to the present invention.

FcRn-receptors for selection may be provided either on the surface of cells expressing naturally the respective receptors or by expression and purification of the extracellular part of the respective receptor. For the purpose of this invention a first screening on FcRn may select for mutant domains which can further be tested in vitro and even further characterized in FACS experiments by binding to cells expressing FcRn receptor. It can be further characterized by affinity ranking of binding to various recombinant FcRn, isoforms and allotypes e.g with surface plasmon resonance techniques.

According to a preferred embodiment of the present invention the immunoglobulin is of human or murine origin.

Since the modified immunoglobulin may be employed for various purposes, in particular in pharmaceutical compositions, the immunoglobulin is preferably of human or murine origin. Of course, the modified immunoglobulin may also be a humanized or chimeric immunoglobulin.

According to another preferred embodiment of the present invention the human immunoglobulin is selected from the group consisting of IgA1, IgA2, IgD, IgE, IgG1, IgG2, IgG3, IgG4 and IgM.

The murine immunoglobulin is preferably selected from the group consisting of IgA, IgD, IgE, IgG1, IgG2A, IgG2B, IgG2C, IgG3 and IgM.

The modified immunoglobulin may be derived from one of the above identified immunoglobulin classes.

The immunoglobulin comprises preferably a heavy and/or light chain of the immunoglobulin or a part thereof.

The modified immunoglobulin may comprise a heavy and/or light chain, at least one variable and/or constant domain.

The immunoglobulin according to the present invention comprises preferably at least one constant and/or at least one variable domain of the immunoglobulin or a part thereof including a minidomain.

A constant domain is an immunoglobulin fold unit of the constant part of an immunoglobulin molecule, also referred to as a domain of the constant region (e.g. CH1, CH2, CH3, CH4, Ck, Cl).

A variable domain is an immunoglobulin fold unit of the variable part of an immunoglobulin, also referred to as a domain of the variable region (e.g. Vh, Vk, Vl, Vd)

A preferred immunoglobulin according to the invention consists of a constant domain selected from the group consisting of CH1, CH2, CH3, CH4, Igk-C, Igl-C, or a part thereof including a minidomain, with at least one loop region, and is characterised in that said at least one loop region comprises at least one amino acid modification forming at least one modified loop region, wherein said at least one modified loop region binds specifically to at least one epitope of an antigen.

Another preferred immunoglobulin according to the invention consists of a variable domain of a heavy or light chain, or a part thereof including a minidomain, with at least one loop region, and is characterised in that said at least one loop region comprises at least one amino acid modification forming at least one modified loop region, wherein said at least one modified loop region binds specifically to at least one epitope of an antigen.

According to a preferred embodiment the constant domain is selected from the group of CH1, CH2, CH3, CH4, Igk-C, Igl-C and combinations thereof.

The modified immunoglobulin according to the present invention may comprise one or more constant domains (e.g. at least two, three, four, five, six, ten domains). If more than one domain is present in the modified immunoglobulin these domains may be of the same type or of varying types (e.g. CH1-CH1-CH2, CH3-CH3). Of course also the order of the single domains may be of any kind (e.g. CH1-CH3-CH2, CH4-CH1-CH3-CH2).

All numbering of the amino acid sequences of the immunoglobulins is according to the IMGT numbering scheme (IMGT, the international ImMunoGeneTics information; Lefranc et al., 1999, Nucleic Acids Res. 27: 209-212; Ruiz et al., 2000 Nucleic Acids Res. 28: 219-221; Lefranc et al., 2001, Nucleic Acids Res. 29: 207-209; Lefranc et al., 2003, Nucleic Acids Res. 31: 307-310; Lefranc et al., 2005, Dev Comp Immunol 29:185-203).

According to another preferred embodiment of the present invention the modified loop regions of CH1, CH2, CH3 and CH4 comprise amino acids 7 to 21, amino acids 25 to 39, amino acids 41 to 81, amino acids 83 to 85, amino acids 89 to 103 and amino acids 106 to 117.

The loop regions of Igk-C and Igl-C of human origin comprise preferably amino acids 8 to 18, amino acids 27 to 35, amino acids 42 to 78, amino acids 83 to 85, amino acids 92 to 100, amino acids 108 to 117 and amino acids 123 to 126.

The loop regions of Igk-C and Igl-C of murine origin comprise preferably amino acids 8 to 20, amino acids 26 to 36, amino acids 43 to 79, amino acids 83 to 85, amino acids 90 to 101, amino acids 108 to 116 and amino acids 122 to 125.

The structural loop regions of the variable domain of the immunoglobulin of human origin comprise preferably amino acids 8 to 20, amino acids 44 to 50, amino acids 67 to 76 and amino acids 89 to 101.

According to a preferred embodiment of the present invention the structural loop regions of the variable domain of the immunoglobulin of murine origin comprise amino acids 6 to 20, amino acids 44 to 52, amino acids 67 to 76 and amino acids 92 to 101.

The above identified amino acid regions of the respective immunoglobulins comprise loop regions to be modified.

The immunoglobulin according to the invention is preferably of camel origin.

Camel antibodies comprise only one heavy chain and have the same antigen affinity as normal antibodies consisting of light and heavy chains. Consequently camel antibodies are much smaller than, e.g., human antibodies, which allows them to penetrate dense tissues to reach the antigen, where larger proteins cannot. Moreover, the comparative simplicity, high affinity and specificity and the potential to reach and interact with active sites, camel's heavy chain antibodies present advantages over common antibodies in the design, production and application of clinically valuable compounds.

The immunoglobulin of camel origin comprises preferably at least one constant domain selected from the group consisting of CH1, CH2 and CH3.

According to a preferred embodiment of the present invention the loop regions of CH1, CH2 and CH3 of the camel immunoglobulin comprise amino acids 8 to 20, amino acids 24 to 39, amino acids 42 to 78, amino acids 82 to 85, amino acids 91 to 103 and amino acids 108 to 117.

According to a preferred embodiment of the present invention the specific binding of the modified immunoglobulin to the molecule is determined by a binding assay selected from the group consisting of immunological assays, preferably enzyme linked immunosorbent assays (ELISA), surface plasmon resonance assays, saturation transfer difference nuclear magnetic resonance spectroscopy, transfer NOE (trNOE) nuclear magnetic resonance spectroscopy, competitive assays, tissue binding assays, live cell binding assays and cellular extract assays.

Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration. These and other methods may take advantage of some fusion partner or label.

The modified immunoglobulin is preferably conjugated to a label selected from the group consisting of organic molecules, enzyme labels, radioactive labels, colored labels, fluorescent labels, chromogenic labels, luminescent labels, haptens, digoxigenin, biotin, metal complexes, metals, colloidal gold and mixtures thereof.

The modified immunoglobulin may be conjugated to other molecules which allow the simple detection of said conjugate in, for instance, binding assays (e.g. ELISA) and binding studies.

Another aspect of the present invention relates to a immunoglobulin consisting of a constant domain selected from the group consisting of CH1, CH2, CH3, CH4, Igk-C, Igl-C, or a part thereof including minidomains, or combinations thereof, with at least one loop region, characterised in that said at least one loop region comprises at least one amino acid modification forming at least one modified loop region, wherein said at least one modified loop region binds specifically to at least one epitope of an antigen It is preferred to combine molecularly at least one modified antibody domain (=binding to the specific partner via the non-variable sequences or structural loop) with at least one other binding molecule which can be an antibody, antibody fragment, a soluble receptor, a ligand or another modified antibody domain.

The molecule is selected from the group consisting of proteinaceous molecules, nucleic acids, and carbohydrates.

The loop regions of the modified immunoglobulins may specifically bind to any kind of binding molecules, in particular to proteinaceous molecules, proteins, peptides, polypeptides, nucleic acids, glycans, carbohydrates, lipids, small organic molecules, anorganic molecules. Of course, the modified immunoglobulins may comprise at least two loop regions whereby each of the loop regions may specifically bind to other molecules or epitopes.

According to a preferred embodiment of the present invention the molecule binding to the modified structural loop region is selected from the group consisting of tumor associated antigens, in particular EpCAM, tumor-associated glycoprotein-72 (TAG-72), tumor-associated antigen CA 125, Prostate specific membrane antigen (PSMA), High molecular weight melanoma-associated antigen (HMW-MAA), tumor-associated antigen expressing Lewis Y related carbohydrate, Carcinoembryonic antigen (CEA), CEACAM5, HMFG PEM, mucin MUC1, MUC18 and cytokeratin tumor-associated antigen, bacterial antigens, viral antigens, allergens, fluorescein, lysozyme, toll-like receptor 9, erythropoietin, CD2, CD3, CD3E, CD4, CD11, CD11a, CD14, CD18, CD19, CD20, CD22, CD23, CD25, CD28, CD29, CD30, CD33 (p67 protein), CD38, CD40, CD40L, CD52, CD54, CD56, CD80, CD147, GD3, IL-1, IL-1R, IL-2, IL-2R, IL-4, IL-5, IL-6, IL-6R, IL-8, IL-12, IL-15, IL-18, IL-23, interferon alpha, interferon beta, interferon gamma; TNF-alpha, TNFbeta2, TNF.alpha., TNFalphabeta, TNF-R1, TNF-RII, FasL, CD27L, CD30L, 4-1BBL, TRAIL, RANKL, TWEAK, APRIL, BAFF, LIGHT, VEG1, OX40L, TRAIL Receptor-1, A1 Adenosine Receptor, Lymphotoxin Beta Receptor, TACI, BAFF-R, EPO; LFA-3, ICAM-1, ICAM-3, integrin beta1, integrin beta2, integrin alpha4/beta7, integrin alpha2, integrin alpha3, integrin alpha4, integrin alpha5, integrin alpha6, integrin alphav, alphaVbeta3 integrin, FGFR-3, Keratinocyte Growth Factor, VLA-1, VLA-4, L-selectin, anti-Id, E-selectin, HLA, HLA-DR, CTLA-4, T cell receptor, B7-1, B7-2, VNRintegrin, TGFbeta1, TGFbeta2, eotaxin1, BLyS (B-lymphocyte Stimulator), complement C5, IgE, factor VII, CD64, CBL, NCA 90, EGFR (ErbB-1), Her2/neu (ErbB-2), Her3 (ErbB-3), Her4 (ErbB4), Tissue Factor, VEGF, VEGFR, endothelin receptor, VLA-4, carbohydrates such as blood group antigens and related carbohydrates, Galili-Glycosylation, Gastrin, Gastrin receptors, tumor associated carbohydrates, Hapten NP-cap or NIP-cap, T cell receptor alpha/beta, E-selectin, digoxin, placental alkaline phosphatase (PLAP) and testicular PLAP-like alkaline phosphatase, transferrin receptor, Heparanase I, human cardiac myosin, Glycoprotein IIb/IIIa (GPIIb/IIIa), human cytomegalovirus (HCMV) gH envelope glycoprotein, HIV gp120, HCMV, respiratory syncital virus RSV F, RSVF Fgp, VNRintegrin, Hep B gp120, CMV, gpIIbIIIa, HIV IIIB gp120 V3 loop, respiratory syncytial virus (RSV) Fgp, Herpes simplex virus (HSV) gD glycoprotein, HSV gB glycoprotein, HCMV gB envelope glycoprotein, *Clostridium perfringens* toxin and fragments thereof.

The modified immunoglobulin according to the present invention may preferably bind to one of the molecules disclosed above. These molecules comprise also allergens.

According to another preferred embodiment of the present invention the amino acid residues of positions 15 to 17, 29 to 34, 85.4 to 85.3, 92 to 94, 97 to 98 and/or 108 to 110 of CH3 are modified.

The modification of the immunoglobulin according to the present invention is preferably a deletion, substitution or an insertion.

According to the present invention at least 1, preferably at least 2, 3, 4, 5, 6, 7, 8, 9, 10 and 15, amino acids are deleted, substituted with other amino acids (also with modified amino acids) or inserted into the loop region of the immunoglobulin. However, the maximum number of amino acids inserted into a loop region of an immunoglobulin may not exceed the number of 30, preferably 25, more preferably 20, amino acids. The substitution and the insertion of the amino acids occurs preferably randomly by methods known in the art and as disclosed in the present patent application.

The immunoglobulin according to the invention is according to a specific embodiment characterised in that the CH3 region comprises SEQ ID No. 16 or SEQ ID No. 18, when EpCam binds to said immunoglobulin, SEQ ID No. 20, when fluorescein binds to said immunoglobulin, SEQ ID No. 22, 24, 26, 28, 30 or 32, when lysozyme binds to said immunoglobulin, SEQ ID No. 34, 36, 38 or 40, when TLR9 binds to said immunoglobulin, and SEQ ID No. 42, when lysozyme and/or erythropoietin bind to said immunoglobulin.

According to a specific embodiment of the invention the immunoglobulin is characterised in that it comprises SEQ ID No. 44 or SEQ ID No. 46, when lysozyme and gp41 bind to said immunoglobulin.

The modified immunoglobulin is preferably conjugated to a label or reporter molecule selected from the group consisting of organic molecules, enzyme labels, radioactive labels, colored labels, fluorescent labels, chromogenic labels, luminescent labels, haptens, digoxigenin, biotin, metal complexes, metals, colloidal gold and mixtures thereof.

Modified immunoglobulins conjugated to labels as specified above may be used, for instance, in diagnostic methods.

Another aspect of the present invention relates to the use of an immunoglobulin according to the present invention or obtainable by a method according to the present invention for the preparation of a vaccine for active immunization. Hereby the immunoglobulin is either used as antigenic drug substance to formulate a vaccine or used for fishing or capturing antigenic structures for use in a vaccine formulation.

Another aspect of the present invention relates to the use of an immunoglobulin according to the present invention or obtainable by a method according to the present invention for the preparation of a protein library of immunoglobulins.

Yet another aspect of the present invention relates to a method for specifically binding and/or detecting a molecule comprising the steps of:

(a) contacting a modified immunoglobulin according to the present invention or a modified immunoglobulin obtainable by a method according to the present invention with a test sample suspected to contain said molecule, and (b) detecting the potential formation of a specific immunoglobulin/molecule complex.

Another aspect of the present invention relates to a method for specifically isolating a molecule comprising the steps of:

(a) contacting a modified immunoglobulin according to the present invention or a modified immunoglobulin obtainable by a method according to the present invention with a sample containing said molecule, (b) separating the specific immunoglobulin/molecule complex formed, and (c) optionally isolating the molecule from said complex.

The immunoglobulins according to the present invention may be used to isolate specifically molecules from a sample. If multi-specific immunoglobulins are used more than one molecules may be isolated from a sample. It is especially advantageous using modified immunoglobulins in such methods because it allows, e.g., to generate a matrix having a homogeneous surface with defined amounts of binding partners (i.e. Modified immunoglobulins) immobilised thereon which able to bind to the molecules to be isolated.

In contrast thereto, if mono-specific binding partners are used no homogeneous matrix can be generated because the single binding partners do not bind with the same efficiency to the matrix.

Another aspect of the present invention relates to a method for targeting a compound to a target comprising the steps of:

(a) contacting a modified immunoglobulin according to the present invention or a modified immunoglobulin obtainable by a method according to the present invention capable to specifically bind to said compound, (b) delivering the immunoglobulin/compound complex to the target.

Modified immunoglobulins according to the present invention may be used to deliver at least one compound bound to the CDRs and/or modified loop regions to a target. Such immunoglobulins may be used to target therapeutic substances to a preferred site of action in the course of the treatment of a disease.

Another aspect of the present invention relates to a protein library comprising an immunoglobulin according to the present invention or obtainable by the method according to the present invention.

Preferred methods for constructing said library can be found above and in the examples. The library according to the present invention may be used to identify immunoglobulins binding to a distinct molecule.

In particular the present invention relates to the use of a protein library comprising an immunoglobulin according to the present invention or obtainable by the method according to the present invention for the design of immunoglobulin derivatives. An existing immunoglobulin can be changed to introduce antigen binding sites into any domain or minidomain by using a protein library of the respective domain of at least 10, preferably 100, more preferably 1000, more preferably 10000, more preferably 100000, most preferably more than 1000000 variant domains with at least one modified loop. The library is then screened for binding to the specific antigen. After molecular characterization for the desired properties the selected domain or minidomain is cloned into the original immunoglobulin by genetic engineering techniques so that it replaces the wild type region. Alternatively, only the DNA coding for the loops or coding for the mutated amino acids may be exchanged to obtain an immunoglobulin with the additional binding site for the specific antigen.

The choice of the site for the mutated, antigen-specific structural loop is dependent on the structure of the original immunoglobulin and on the purpose of the additional binding site. If, for example, the original molecule is a complete immunoglobulin which needs to have inserted an additional antigen binding site without disturbance of the effector function, the loops to be modified would be selected from domains distant from CH2 and CH3 which are the natural binding partners to Fc-effector molecules. If the original immunoglobulin is a Fab, modification of loops in constant domains of the light chains or the heavy chains or the respective variable domains is possible. To generate a library one may prepare libraries of mutant original molecules which have mutations in one ore more structural loops of one or more domains. The selection with complete mutated original molecules may have some advantages as the selection for antigen binding with a modified structural loop will deliver the sterically advantageous modifications if tested also for the other properties the mutated immunoglobulin should show.

The size requirement (i.e. the number of variant proteins) of a protein library of a mutated domain or a minidomain or a fusion molecule of a domain is dependent on the task. In general, a library to generate an antigen binding site de novo needs to be larger than a library used to further modify an already existing engineered antigen binding site made of a modified structural loop (e.g. for enhancing affinity or changing fine specificity to the antigen).

The present invention also relates to an immunoglobulin library or a nucleic acid library comprising a plurality of immunoglobulins, e.g. a constant or variable domain, a minidomain and/or at least one structural loop region contained in a minidomain, or nucleic acid molecules encoding the same. The library contains members with different modifications, wherein the plurality is defined by the modifications in the at least one structural loop region. The nucleic acid library preferably includes at least 10 different members (resulting in one amino acid exchange) and more preferably includes at least 100, more preferably 1000 or 10000 different members (e.g. designed by randomisation strategies or combinatory techniques). Even more diversified individual member numbers, such as at least 1000000 or at least 10000000 are also preferred.

A further aspect of the invention is the combination of two different domains or minidomains selected from at least two libraries according to the invention in order to generate multispecific immunoglobulins. These selected specific immunoglobulins may be combined with each other and with other molecules, similar to building blocks, to design the optimal arrangement of the domains or minidomains to get the desired properties.

Furthermore, one or more modified immunoglobulins according to the invention may be introduced at various or all the different sites of a protein possible without destruction of the structure of the protein. By such a "domain shuffling" technique new libraries are created which can again be selected for the desired properties.

The preferred library contains immunoglobulins according to the invention, selected from the group consisting of domains of an immunoglobulin, minidomains or derivatives thereof.

A preferred embodiment of the present invention is a binding molecule for an antigen (antigen binding molecule) comprising at least one immunoglobulin domain and a structural loop region being modified according to the present invention to bind to the antigen, wherein said binding molecule does not comprise variable domains of an antibody. It may comprise other parts useable for antibody activities (e.g. such as natural or modified effector regions (sequences); however, it lacks the "natural" binding region of antibodies, i.e. the variable domains in their naturally occurring position. These antigen binding molecules according to the present invention have the advantages described above for the present molecules, yet without the specific binding activity of antibodies; however with a newly introduced specific binding activity in the structural loop region.

Preferably, these antigen binding molecules according to the present invention comprise CH1, CH2, CH3, CH4, Igk-C, Igl-C and combinations thereof; said combinations comprising at least two, preferably at least four, especially at least six constant domains and at least one structural loop region modified according to the present invention. Preferably these structural loop regions are either connected via structural loop region modified according to the present invention or the structural loops being naturally present between such two constant domains. An embodiment of these antigen binding molecules according to the present invention consists of the Fc region of an antibody with at least one modification in a structural loop according to the present invention. Also for the antigen binding molecules according to the present invention it is preferred that the new antigen binding sites in the structural loops are introduced by randomising technologies, i.e. by exchanging one or more amino acid residues of the loop by randomisation techniques or by introducing randomly generated inserts into such structural loops. Alternatively preferred is the use of combinatorial approaches.

According to another aspect, the present invention relates to a modified immunoglobulin having an antigen binding site foreign to the unmodified immunoglobulin and incorporated in one or more structural loops. The term "foreign" means that the antigen binding site is not naturally formed by the specific region of the immunoglobulin, and a foreign binding partner, but not the natural binding partner of an immunoglobulin, is bound by the antigen binding site. This means that a binding partner, such as a Fc-receptor or an effector of the immune system, is not considered to be bound by the antigen binding site foreign to the unmodified immunoglobulin.

Preferably, the antigen is selected from the group consisting of pathogen antigen, tumour associated antigen, enzyme, substrate, self antigen, organic molecule or allergen. More preferred antigens are selected from the group consisting of viral antigens, bacterial antigens or antigens from pathogens of eukaryote or phages. Preferred viral antigens include HAV-, HBV-, HCV-, HIV I-, HIV II-, Parvovirus-, Influenza-, HSV-, Hepatitis Viruses, Flaviviruses, Westnile Virus, Ebola Virus, Pox-Virus, Smallpox Virus, Measles Virus, Herpes Virus, Adenovirus, Papilloma Virus, Polyoma Virus, Parvovirus, Rhinovirus, Coxsackie virus, Polio Virus, Echovirus, Japanese Encephalitis virus, Dengue Virus, Tick Borne Encephalitis Virus, Yellow Fever Virus, Coronavirus, respiratory syncytial virus, parainfluenza virus, La Crosse Virus, Lassa Virus, Rabies Viruse, Rotavirus antigens; preferred bacterial antigens include *Pseudomonas*-, *Mycobacterium*-, *Staphylococcus*-, *Salmonella*-, Meningococcal-, Borellia-, *Listeria, Neisseria*-, *Clostridium*-, *Escherichia*-, *Legionella*-, *Bacillus*-, *Lactobacillus*-, *Streptococcus*-, *Enterococcus*-, *Corynebacterium*-, *Nocardia*-, *Rhodococcus*-, *Moraxella*-, *Brucella, Campylobacter*-, *Cardiobacterium*-, *Francisella*-, *Helicobacter*-, *Haemophilus*-, *Klebsiella*-, *Shigella*-, *Yersinia*-, *Vibrio*-, *Chlamydia*-, *Leptospira*-, *Rickettsia*-, *Mycobacterium*-, *Treponema*-, *Bartonella*-antigens. Preferred eukaryotic antigens of pathogenic eukaryotes include antigens from *Giardia, Toxoplasma, Cyclospora, Cryptosporidium, Trichinella*, Yeasts, *Candida, Aspergillus, Cryptococcus, Blastomyces, Histoplasma, Coccidioides.*

Preferred immunoglobulins according to the present invention comprise at least two antigen binding sites, the first site binding to a first epitope, and the second site binding to a second epitope.

According to a preferred embodiment, the present immunoglobulin comprises at least two loop regions, the first loop region binding to a first epitope, and the second loop region binding to a second epitope. Either the at least first or at least second loop region or both may be contain a structural loop. The immunoglobulins according to the present inventions include the fragments thereof known in the art to be functional which contain the essential elements according to the present invention: the structural loop region modified according to the present invention.

Preferably, the immunoglobulin according to the present invention is composed of at least two immunoglobulin domains, or a part thereof including a minidomain, and each domain contains at least one antigen binding site.

Also preferred is an immunoglobulin according to the invention, which comprises at least one domain of the constant region and/or at least one domain of the variable region of the immunoglobulin, or a part thereof including a minidomain. Thus, a variable domain, which is for example modified in the C-terminal region, or the variable domain linked to a modified CH1 region, for instance a modified CH1 minidomain, is one of the preferred embodiments.

The preferred immunoglobulin according to the invention comprises a domain that has at least 50% homology with the unmodified domain.

The term "homology" indicates that polypeptides have the same or conserved residues at a corresponding position in their primary, secondary or tertiary structure. The term also extends to two or more nucleotide sequences encoding the homologous polypeptides.

"Homologous immunoglobulin domain" means an immunoglobulin domain according to the invention having at least about 50% amino acid sequence identity with regard to a full-length native sequence immunoglobulin domain sequence or any other fragment of a full-length immunoglobulin domain sequence as disclosed herein. Preferably, a homologous immunoglobulin domain will have at least about 50% amino acid sequence identity, preferably at least about 55% amino acid sequence identity, more preferably at least about 60% amino acid sequence identity, more preferably at least about 65% amino acid sequence identity, more preferably at least about 70% amino acid sequence identity, more preferably at least about 75% amino acid sequence identity, more preferably at least about 80% amino acid sequence identity, more preferably at least about 85% amino acid sequence identity, more preferably at least about 90% amino acid sequence identity, more preferably at least about 95% amino acid sequence identity to a native immunoglobulin domain sequence, or any other specifically defined fragment of a full-length immunoglobulin domain sequence as disclosed herein.

"Percent (%) amino acid sequence identity" with respect to the immunoglobulin domain sequences identified herein is defined as the percentage of amino acid residues in a candidate sequence that are identical with the amino acid residues in the specific immunoglobulin domain sequence, after aligning the sequence and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

% amino acid sequence identity values may be obtained as described below by using the WU-BLAST-2 computer program (Altschul et al., Methods in Enzymology 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the immunoglobulin domain of interest having a sequence derived from the native immunoglobulin domain and the comparison amino acid sequence of interest (i.e., the sequence against which the immunoglobulin domain of interest is being compared which may be the unmodified immunoglobulin domain) as determined by WU-BLAST-2 by (b) the total number of amino acid residues of the non-randomized parts of the immunoglobulin domain of interest. For example, in the statement "a polypeptide comprising an amino acid sequence A which has or having at least 80% amino acid sequence identity to the amino acid sequence B", the amino acid sequence A is the comparison amino acid sequence of interest and the amino acid sequence B is the amino acid sequence of the immunoglobulin domain of interest.

In a preferred embodiment the immunoglobulin according to the invention is a bispecific antibody or a bispecific single chain antibody. Further preferred is that the immunoglobulin comprises a bispecific domain or a part thereof including a minidomain.

The immunoglobulin according to the present invention may be used for any purpose known in the art for immunoglobulins but also enables applications which are depending on the combination of specificities introduced by the present invention. Accordingly, the immunoglobulins according to the present inventions are preferably used for therapeutic and prophylactic use (e.g. as an active or passive immunotherapy); for preparative and analytic use and for diagnostic use.

Another aspect of the present invention relates to a kit of binding partners containing
(a) a modified immunoglobulin having an antigen binding site foreign to the immunoglobulin incorporated in one or more structural loops, and
(b) a binding molecule containing an epitope of said antigen.

Such a binding molecule of this kit according to the present invention may be used for identifying the binding specificity of the modified immunoglobulin according to the present invention. By using the binding molecule of this kit according to the present invention, the potency of the modified immunoglobulins according to the present invention may be determined.

Potency as defined here is the binding property of the modified molecule to its antigen. The binding can be determined quantitatively and/or qualitatively in terms of specificity and/or affinity and/or avidity as used for quality control purposes.

Moreover, the binding molecule of a kit according to the present invention may be used for selecting the modified immunoglobulin according to the present invention from a library consisting of at least 10, preferably at least 100, more preferably at least 1000, more preferred at least 10000, especially at least 100000 immunoglobulins with different modifications in the structural loops.

In accordance with the present invention, one of the key features of the present invention is that the engineering of the immunoglobulin domains takes place in regions which are not normally involved in antigen binding, in other words, in regions other than the CDRs of an antibody. It was observed that the specific fold of immunoglobulin domains allows the introduction of random mutations in regions which are structurally analogous to the CDRs but different in position in sequence. The regions identified by the present invention are, like CDRs, loop regions connecting the beta strands of the immunoglobulin fold.

More specifically, it is described herein that by introducing random mutations in the loops connecting beta strands A-B and E-F of a human IgG1 CH3 domain, mutated CH3 domains were selected that bind specifically to either Toll like receptor 9-peptide (TLR-9) or to hen egg lysozyme, which are a peptide and a protein respectively that are not normally recognized and bound by human CH3 domains of IgG1. The mutations introduced by us include mutations in which selected amino acid residues in the wildtype sequence were replaced by randomly chosen residues, and they also include insertions of extra amino acid residues in the loops mentioned above.

By analogy the immunoglobulin domains from any class of immunoglobulins and from immunoglobulins from any species are amenable to this type of engineering. Furthermore not only the specific loops targeted in the present invention can be manipulated, but any loop connecting beta strands in immunoglobulin domains can be manipulated in the same way.

Engineered immunoglobulin domains from any organism and from any class of immunoglobulin can be used according to the present invention either as such (as single domains), or as part of a larger molecule. For example, they can be part of an intact immunoglobulin, which accordingly would have its "normal" antigen binding region formed by the 6 CDRs and the new, engineered antigen binding region. Like this, a multi-specific, e.g. bispecific, immunoglobulin could be generated. The engineered immunoglobulin domains can also be part of any fusion protein. The use of these engineered immunoglobulin domains is in the general field of the use of immunoglobulins.

The domains of the following immunoglobulins are understood as immunoglobulin domains here:
for IgG, IgD and IgA: VL, CL, VH, CH1, CH2, CH3
for IgM and IgE: VL, CL, VH, CH1, CH2, CH3, CH4

1. Single immunoglobulin domains randomized on one side, i.e. either in loops connecting beta-strands B-C, D-E or F-G (the "tip", with the exception of variable domains which are covered by many patents) or beta-strands A-B, C-D, (C-C' and C"-D in the case of variable domains) or E-F (the "bottom"). Single loops or any combination of loops can be randomized. Residues can be changed, deleted, or additional residues can be inserted.

2. Single immunoglobulin domains randomized on both sides, the tip and the bottom.

3. any protein containing one of the single randomized domains, such as:
   a) "single-chain CH3" dimers (scCH3), scCH2, scCH1/CL, randomized on one or both sides
   b) single-chain Fv randomized on the "bottom", i.e. on the side opposite to the CDRs
   c) Fab fragments randomized at the "bottom", i.e. on the C-terminal end of the CH1 and of the CL domain
   d) Fc fragments (i.e. proteins consisting of CH2-CH3) randomized on one or both sides
   e) complete immunoglobulins randomized on the bottom of the Fc
   f) other suitable domains The primary advantages of the single domains: are very similar to all the arguments that are used to promote camel VH molecules ("nanobodies"). The randomized immunoglobulin domains are very small proteins (molecular weight ca. 12-15 kDa, depending on the number of inserted amino acid residues) and therefore will have the following advantages as compared to conventional antibodies or antibody fragments such as scFv and Fabs: recognizing uncommon or hidden epitopes, binding into cavities or active sites of protein targets, ease of manufacture, and many others. In the case of an immunoglobulin domain that is randomized on both sides, a bivalent or a bispecific molecule can be generated. The main advantages of the single domains as part of fusion proteins is additional binding properties can be engineered on any other protein.

It is contemplated that any expression system can be used to make the proteins. An analogy to the single domains as described here can be found in the antibodies from the camel, which only has a VH but no VL In these proteins, only 3 CDRs (instead of 6 as in "normal" antibodies are responsible for antigen binding).

The following patent references are incorporated herein by reference as if set forth in their entirety herewith:

U.S. Pat. No. 6,294,654 Modified immunoglobulin molecule incorporating an antigen in a non-CDR loop region U.S. Pat. No. 5,844,094 Target binding polypeptide U.S. Pat. No. 5,395,750 Methods for producing proteins which bind to predetermined antigens US 2004/0071690 High avidity polyvalent and polyspecific reagents US 2004/0018508 Surrogate antibodies and methods of preparation and use thereof US 2003/0157091 Multi-functional proteins US 2003/0148372 Method to screen phage display libraries with different ligands US 2002/0103345 Bispecific immunoglobulin-like antigen binding proteins and method of production US 2004/0097711 Immunoglobulin superfamily proteins US 2004/0082508 Secreted proteins US 2004/0063924 Secreted proteins US 2004/0043424 Immunoglobulin superfamily proteins U.S. Pat. No. 5,892,019 Production of a single-gene-encoded immunoglobulin U.S. Pat. No. 5,844,094 Target binding polypeptide

DESCRIPTION OF SPECIFIC EXAMPLES

Example 1: Construction of the CH3 Library and Phage Surface Display

The crystal structure of an IgG1 Fc fragment, which is published in the Brookhaven Database as entry 1OQO.pdb was used to aid in the design of the mutated CH3 domain.

Figure 3:
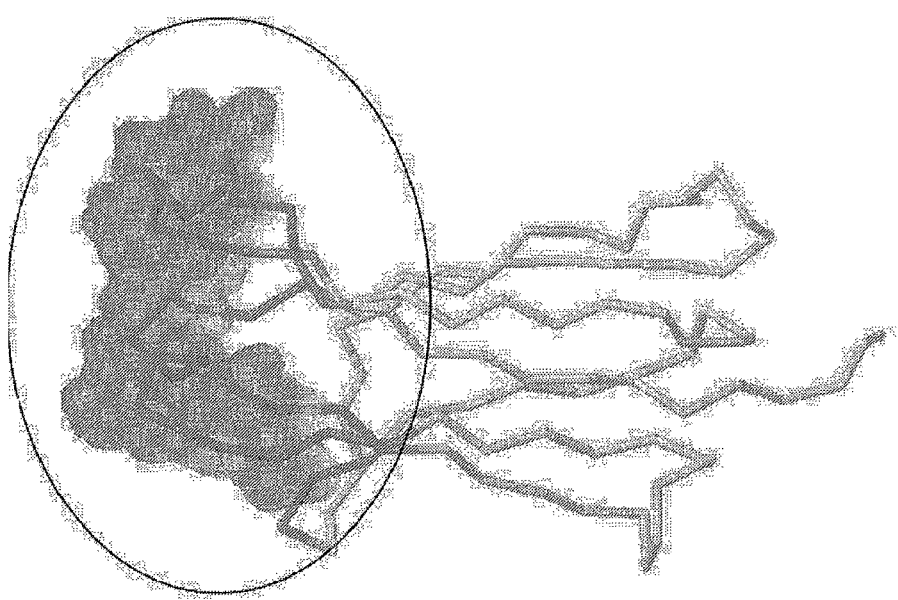
Figure 4:
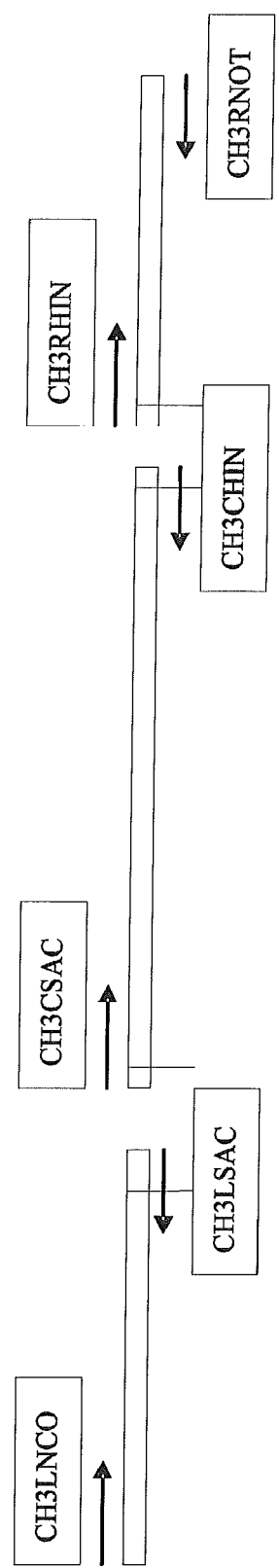
Figure 5:
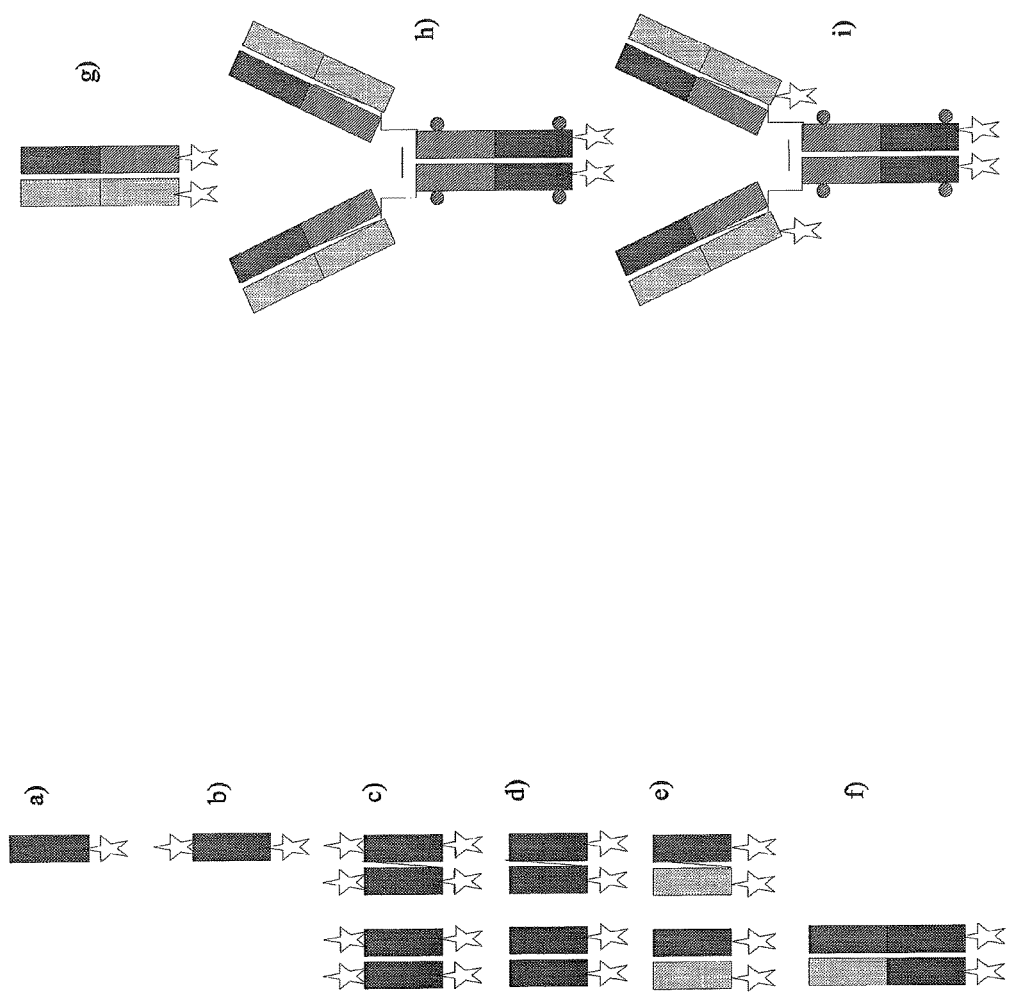
Figure 6:
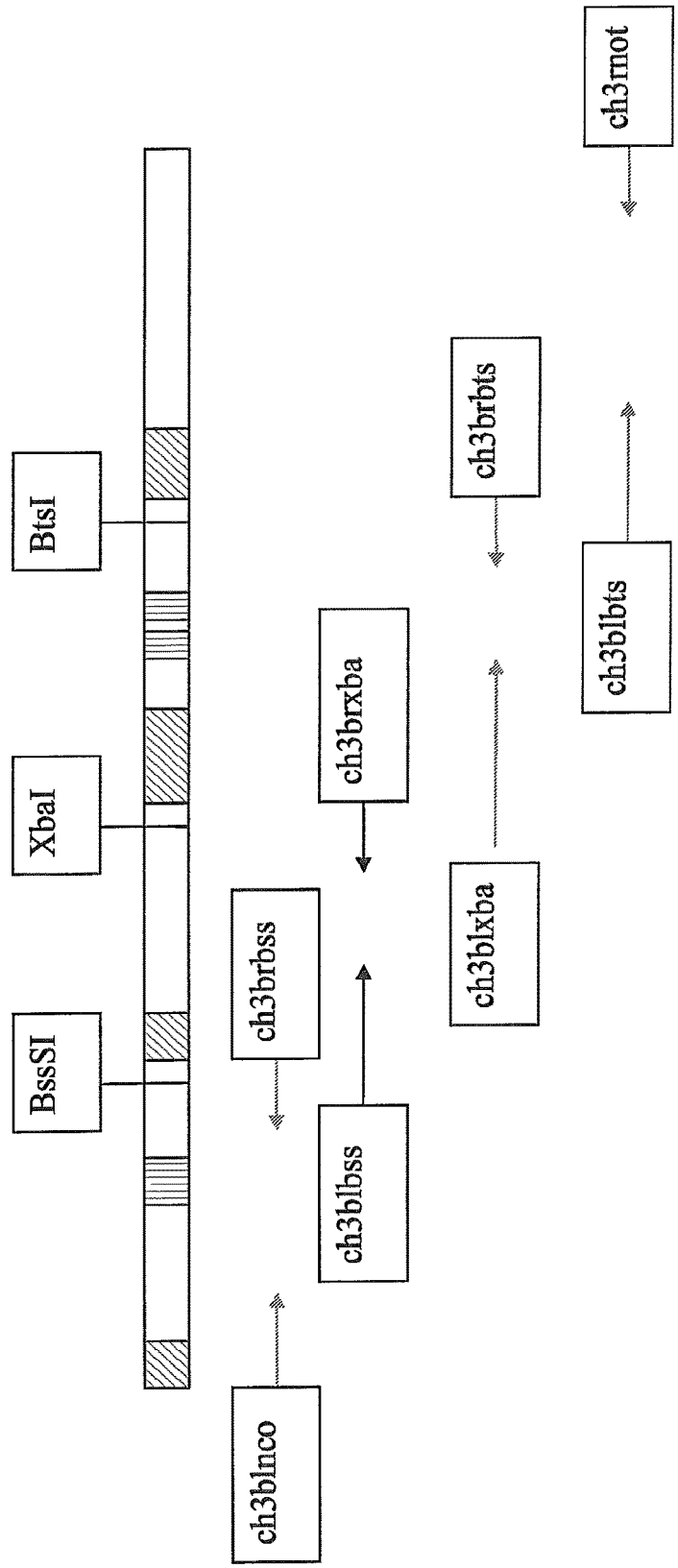

The sequence which was used as the basis for construction of the CH3 library is given in SEQ ID No. 1. In this sequence, the first amino acid corresponds to Proline 343 of chain A of Brookhaven database entry 1ogo.pdb. The last residue contained in 1ogo.pdb is Serine 102 of SEQ ID No. 1. After detailed analysis of the structure of 1ogo.pdb and by visual inspection of the residues forming the loops which connect the beta strands, it was decided to randomize residues 17, 18 and 19, which are part of the loop connecting beta strand A-B as well as 71, 72, 73, 76, and 77, which are part of the loop connecting beta strand E-F of SEQ ID No. 1. A molecular model of the engineered CH3 domain, with the randomized part indicated by a solvent accessible surface is shown in FIG. 3. The engineered gene was produced by a series of PCR reactions followed by ligation of the resulting PCR products. To facilitate ligation, some of the codons of the nucleotide sequence coding for SEQ ID No. 1 were modified to produce restriction sites without changing the amino acid sequences (silent mutations). For insertion into the cloning vector pHEN1 (Nucleic Acids Res. 1991 Aug. 11; 19(15):4133-7. Multi-subunit proteins on the surface of filamentous phage: methodologies for displaying antibody (Fab) heavy and light chains. Hoogenboom H R, Griffiths A D, Johnson K S, Chiswell D J, Hudson P, Winter G.) in frame with the pelB secretion signal, extra nucleotide residues encoding Met-Ala were attached at the 5' end of the sequence to create an NcoI restriction site. For the randomized residues, the codon NNS (IUPAC code, where S means C or G) was chosen which encodes all 20 naturally occurring amino acids, but avoids 2 out of 3 stop codons. The engineered sequence is given as a nucleotide sequence in SEQ ID No. 2 and as an amino acid sequence in SEQ ID No. 3. The Letter X in SEQ ID No. 3 denotes randomized amino acid residues. The sequences of the PCR primers used for assembly of the mutated CH3 domain are given in SEQ ID No. 4 through 9. FIG. 4 shows a schematic presentation of the PCR fragments generated for assembly of the mutated gene, and the primers used therefor.

cDNA of the heavy chain of the human monoclonal antibody 3D6 (Felgenhauer M, Kohl J, Rüker F. Nucleotide sequences of the cDNAs encoding the V-regions of H- and L-chains of a human monoclonal antibody specific to HIV-1-gp41. Nucleic Acids Res. 1990 Aug. 25; 18(16):4927) was used as template for the PCR reactions. The 3 PCR products were digested with SacI and/or HindIII respectively and ligated together. The ligation product was further digested with NcoI and NotI and ligated into the surface display phagemid vector pHEN1, which had previously been digested with NcoI and NotI. A number of selected clones were controlled by restriction analysis and by DNA sequencing and were found to contain the insert as planned, including the correctly inserted randomized sequences. For the following steps of phage preparation, standard protocols were followed. Briefly, the ligation mixture was transformed into E. coli TG1 cells by electroporation. Subsequently, phage particles were rescued from E. coli TG1 cells with helper phage M13-KO7. Phage particles were then precipitated from culture supernatant with PEG/NaCl in 2 steps, dissolved in water and used for selection by panning or, alternatively, they were stored at minus 80° C.

Example 2: Construction of the CH3+3 Library

This library was constructed and cloned in the same way as the CH3 library. The amino acid sequence of the construct is given in SEQ ID No. 10, the corresponding nucleotide sequence in SEQ ID No. 11, and the primers used for construction were SEQ ID No. 4-7, SEQ ID No. 9 and SEQ ID No. 12.

Example 3: Construction of the CH3+5 Library

This library was constructed and cloned in the same way as the CH3 library. The amino acid sequence of the construct is given in SEQ ID No. 13, the corresponding nucleotide sequence in SEQ ID No. 14, and the primers used for construction were SEQ ID No. 4-7, SEQ ID No. 9 and SEQ ID No. 15.

Example 4: Panning of the CH3-Phage Library on TLR-9 Peptide 3 panning rounds were performed according to standard protocols. Briefly, the following method was applied. Maxisorp 96-well plates (Nunc) were coated with a synthetic peptide representing part of the sequence of Toll-like Receptor 9 (TLR-9). 200 μl of the following solution were added per well: 0.1M Na-carbonate buffer, pH 9.6, with the following concentrations of dissolved peptide:
  1st panning round: 1 mg/ml TLR-9 peptide
  2nd panning round: 500 μg/ml TLR-9 peptide
  3rd panning round: 100 μg/ml TLR-9 peptide Incubation was for 1 hour at 37° C., followed by blocking with 2% dry milk (M-PBS) with 200 µl per well for 1 hour at room temperature.

The surface display phage library was then allowed to react with the bound peptide by adding 100 µl phage suspension and 100 µl 4% dry milk (M-PBS), followed by incubation for 45 minutes with shaking and for 90 minutes without shaking at room temperature.

Unbound phage particles were washed away as follows. After the 1st panning round: 10×300 µl T-PBS, 5×300 µl PBS; after the 2nd panning round: 15×300 µl T-PBS, 10×300 µl PBS; after the 3rd panning round: 20×300 µl T-PBS, 20×300 PBS.

Elution of bound phage particles was performed by adding 200 µl per well of 0.1 M glycine, pH 2.2, and incubation with shaking for 30 minutes at room temperature. Subsequently, the phage suspension was neutralized by addition of 60 µl 2M Tris-Base, followed by infection into *E. coli* TG1 cells by mixing 10 ml exponentially growing culture with 0.5 ml eluted phage and incubation for 30 minutes at 37° C. Finally, infected bacteria were plated on TYE medium with 1% glucose and 100 µg/ml ampicillin, and incubated at 30° C. overnight.

TABLE 1

Results of the panning of the CH3 - phage library on TLR-9 peptide (Phage titers)

| Panning round | Concentration TLR-9 at panning | Input (phage/ml) | Output (phage/ml) |
|---|---|---|---|
| 1st | 1 mg/ml | $6 \times 10^{18}$ | $2 \times 10^{10}$ |
| 2nd | 0.5 mg/ml | $4 \times 10^{18}$ | $2 \times 10^{10}$ |
| 3rd | 0.1 mg/ml | $4 \times 10^{22}$ | $6 \times 10^{10}$ |

Example 5: Cloning of Selected Clones of CH3 Mutants Selected Against TLR-9 for Soluble Expression Phagemid DNA from the phage selected through the 3 panning rounds was isolated with a midi-prep. DNA encoding mutated CH3-regions was batch-amplified by PCR and cloned NcoI-NotI into the vector pNOTBAD/Myc-His, which is the *E. coli* expression vector pBAD/Myc-His (Invitrogen) with an inserted NotI restriction site to facilitate cloning. Ligated constructs were transformed into *E. coli* LMG194 cells (Invitrogen) with electroporation, and grown at 30° C. on TYE medium with 1% glucose and ampicillin overnight. Selected clones were inoculated into 200 µl 2×YT medium with ampicillin, grown overnight at 30° C., and induced by adding L-arabinose to an end concentration of 0.1%. After expression at 16° C. overnight, the cells were harvested by centrifugation and treated with 100 µl Na-borate buffer, pH 8.0, at 4° C. overnight for preparation of periplasmic extracts. 50 µl of the periplasmic extracts were used in ELISA (see below).

Example 6: ELISA of CH3 Mutants Selected Against TLR-9 Selected Clones were Assayed for Specific Binding to the TLR-9 Peptide by ELISA Coating: Microtiter plate (NUNC, Maxisorp), 100 µl per well, 20 µg TLR-9 peptide/ml 0.1 M Na-carbonate buffer, pH 9.6, 1 h at 37° C.
Wash: 3×200 µl PBS
Blocking: 1% BSA-PBS, 1 h at RT
Wash: 3×200 µl PBS
Periplasmic extract binding: 50 µl periplasmic extract 50 µl 2% BSA-PBS, at room temperature overnight
Wash: 3×200 µl PBS
1st antibody: anti-His4 (Qiagen), 1:1000 in 1% BSA-PBS, 90 min at RT, 100 µl per well
Wash: 3×200 µl PBS
2nd antibody: goat anti mouse*HRP (SIGMA), 1:1000 in 1% BSA-PBS, 90 min at RT, 100 µl per well
Wash: 3×200 µl PBS
Detection: 3 mg/ml OPD in Na-citrate/phosphate buffer, pH 4.5, 0.4 µl 30% $H_2O_2$
Stopping: 100 ml 3M $H_2SO_4$
Absorbance read: 492/620 nm Clones that gave a high signal in this first, preliminary ELISA were cultured in a 20-ml volume at the same conditions as described above. Their periplasmic extracts were isolated in 1/20 of the culture volume as described above and tested with ELISA (as described above) for confirmation.

TABLE 2

Results of confirmation ELISA

| clone | with antigen $A_{492/620}$ 4 readings | without antigen $A_{492/620}$ 1 reading |
|---|---|---|
| A67 | 0.0435 | 0.019 |
| B54 | 0.0937 | 0.051 |
| C67 | 0.0295 | 0.013 |

Background (antigen alone) (12 parallel readings): 0.0115

Example 7: Panning of the CH3 and of the CH3+5-Phage Library on Hen Egg Lysozyme 3 panning rounds were performed. Maxisorp 96-well plates (Nunc) were coated with hen egg lysozyme, by adding 200 µl of the following solution per well:

PBS, with the following concentrations of dissolved hen egg lysozyme:
1st panning round: 2 mg/ml HEL
2nd panning round: 1 mg/ml HEL
3rd panning round: 1 mg/ml HEL Incubation was for 1 hour at 37° C., followed by blocking with 2% dry milk (M-PBS) with 200 µl per well for 1 hour at room temperature.

The surface display phage library was then allowed to react with the bound hen egg lysozyme by adding 100 µl phage suspension and 100 µl 4% dry milk (M-PBS), followed by incubation for 45 minutes with shaking and for 90 minutes without shaking at room temperature.

Unbound phage particles were washed away as follows:
1st panning round: 10×300 µl T-PBS, 5×300 µl PBS
2nd panning round: 15×300 µl T-PBS, 10×300 µl PBS
3rd panning round: 20×300 µl T-PBS, 20×300 µl PBS Elution of bound phage particles was performed by adding 200 µl per well of 0.1 M glycine, pH 2.2, and incubation with shaking for 30 minutes at room temperature. Subsequently, the phage suspension was neutralized by addition of 60 µl 2M Tris-Base, followed by infection into *E. coli* TG1 cells by mixture of 10 ml exponentially growing culture with 0.5 ml eluted phage and incubation for 30 minutes at 37° C. Finally, infected bacteria were plated on TYE medium with 1% glucose and 100 µg/ml ampicillin, and incubated at 30° C. overnight.

TABLE 3

Results of the panning of phage library CH3 on hen egg lysozyme (Phage titers)

| Panning round | Concentration HEL at panning | Input (phage/ml) | Output (phage/ml) |
|---|---|---|---|
| 1st | 2 mg/ml |  | $4.7 \times 10^{10}$ |
| 2nd | 1 mg/ml | $1.29 \times 10^{22}$ | $8.0 \times 10^{9}$ |
| 3rd | 1 mg/ml | $5.71 \times 10^{20}$ | $4.8 \times 10^{10}$ |

TABLE 4

Results of the panning of the phage library CH3 + 5 on hen egg lysozyme (HEL) (phage titers)

| Panning round | Concentration HEL at panning | Input (phage/ml) | Output (phage/ml) |
|---|---|---|---|
| 1st | 2 mg/ml | $8.3 \times 10^{16}$ | $2.9 \times 10^{9}$ |
| 2nd | 1 mg/ml | $2.1 \times 10^{19}$ | $2.6 \times 10^{9}$ |
| 3rd | 1 mg/ml | $5.4 \times 10^{19}$ | $1.2 \times 10^{10}$ |

Example 8: Cloning of Selected Clones of Example 7 for Soluble Expression

The cloning of selected clones for soluble expression was performed as described above for the CH3 mutants selected against TLR-9.

Example 9: Soluble Expression of Selected Clones of Example 7

The soluble expression of selected clones was performed as described above for the CH3 mutants selected against TLR-9. Periplasmic extracts were tested in a preliminary ELISA (protocol see example 10)

Clones that gave a high signal in this first, preliminary ELISA were cultured in a 20-ml volume at the same conditions as described above. Their periplasmic extracts were isolated in 1/20 of the culture volume as described above and tested with ELISA (as described in example 10) for confirmation.

Example 10: ELISA of CH3 Mutants Selected Against Hen Egg Lysozyme

Coating: Microtiter plate (NUNC, Maxisorp), 100 µl per well, 100 µg hen egg lysozyme/ml in PBS, 1 h at 37° C.
Wash: 3×200 µl PBS
Blocking: 1% BSA-PBS, 1 h at RT
Wash: 3×200 µl PBS
Periplasmic extract binding: 50 µl periplasmic extract 50 µl 2% BSA-PBS, at room temperature overnight
Wash: 3×200 µl PBS
1st antibody: anti-His4 (Qiagen), 1:1000 in 1% BSA-PBS, 90 min at RT, 100 µl per well
Wash: 3×200 µl PBS
2nd antibody: goat anti mouse*HRP (SIGMA), 1:1000 in 1% BSA-PBS, 90 min at RT (room temperature), 100 µl per well
Wash: 3×200 µl PBS
Detection: 3 mg/ml OPD in Na-citrate/phosphate buffer, pH 4.5, 0.4 µl 30% $H_2O_4$
Stopping: 100 ml 3M $H_2SO_4$
Absorbance read: 492/620 nm

TABLE 5

Results of confirmation ELISA of $C_H3$ mutants selected against hen egg lysozyme

| clone | with antigen $A_{492/620}$ 4 readings | without antigen $A_{492/620}$ 1 reading |
|---|---|---|
| B12 | 0.396 | 0.012 |
| D10 | 0.415 | 0.026 |
| D46 | 0.398 | 0.011 |

Background (antigen alone) (12 parallel readings): 0.1763

TABLE 6

Results of confirmation ELISA with antigen dilutions of $C_H3$ mutants selected against hen egg lysozyme

| clone | c (µg/ml) | | | | | | | | | |
|---|---|---|---|---|---|---|---|---|---|---|
|  | 200 | 100 | 50 | 25 | 12.5 | 6.25 | 3.125 | 1.55 | 0.78 | 0.39 |
| B12 | 0.707 | 0.532 | 0.432 | 0.297 | 0.192 | 0.150 | 0.148 | 0.049 | 0.034 | 0.015 |
| D46 | 0.713 | 0.561 | 0.342 | 0.220 | 0.133 | 0.088 | 0.047 | 0.032 | 0.021 | 0.010 |
| D10 | 0.715 | 0.685 | 0.571 | 0.368 | 0.231 | 0.175 | 0.171 | 0.068 | 0.047 | 0.026 |
| — (nc) | 0.449 | 0.360 | 0.165 | 0.072 | 0.038 | 0.023 | 0.017 | 0.013 | 0.009 | 0.007 | nc: no periplasmic extract added

It is noted that hen egg lysozyme reacts with anti-his$_4$ antibody, therefore a relatively high background was observed.

TABLE 7

Results of confirmation ELISA of $C_H3$ + 5 mutants selected against hen egg lysozyme

| clone | with antigen $A_{492/620}$ 4 readings | without antigen $A_{492/620}$ 1 reading |
|---|---|---|
| A13 | 0.197 | 0.016 |
| A66 | 0.461 | 0.019 |
| B18 | 0.533 (5 readings) | Not done |
| B20 | 0.184 | 0.016 |
| B68 | 0.535 | 0.019 |
| B40 | 0.706 | 0.051 |
| C24 | 0.352 | 0.072 |
| D22 | 0.147 | 0.019 |
| C22 | 0.439 | 0.017 |
| D37 | 0.360 | 0.026 |
| D40 | 0.559 | 0.034 |
| D56 | 0.369 | 0.019 |

Background (antigen alone) (12 parallel readings): 0.1334

Note:
hen egg lysozyme reacts with anti-his$_4$ antibody, therefore a relatively high background was observed.

Example 11: CL Library

Visual inspection of the crystal structure of an Fab fragment (the structure of the Fab of the human monoclonal antibody 3D6 is used: RSCB Protein Data Bank Entry 1DFB.PDB (He X M, et al. Proc Natl Acad Sci USA. 1992 Aug. 1; 89(15):7154-8) and computer-aided analysis (e.g. Protein Explorer is used for this purpose) of the secondary and tertiary structure of this protein) allows to identify residues located in loop regions which connect the beta-strands of the CL-domain scaffold. These residues comprise amino acids 8 to 18, amino acids 27 to 35, amino acids 42 to 78, amino acids 83 to 85, amino acids 92 to 100, amino acids 108 to 117 and amino acids 123 to 126 (numbering according to the IMGT numbering system (Lefranc M P, et al. Nucleic Acids Res. 2005 Jan. 1; 33 (Database issue): D593-7; Lefranc M P, et al. Dev Comp Immunol. 2005; 29(3):185-203)).

More specifically, residues 11, 12, 14-18, and 92-95 are randomized within the human CL domain (SEQ ID No. 48). Randomization is achieved by PCR amplification of the coding sequences with PCR primers in which the positions of the relevant codons are encoded by the nucleotide sequence 5'-NNS-3', which potentially encodes for all 20 amino acids while avoiding 2 out of 3 stop codons. The library insert is amplified by two separate PCR reactions, and the two PCR fragments are ligated together via a HpyCH4IV restriction site which is introduced as a silent mutation by the PCR primers. The primers further provide the restriction endonuclease sites NcoI and NotI respectively for cloning into the phage display vector pHEN (Hoogenboom H R, et al. Nucleic Acids Res. 1991 Aug. 11; 19(15): 4133-7). The C-terminal cystein of the CL domain is not included for the phage display, but can be added later on when a modified CL clone is used e.g. for the construction of an Fab fragment.

As a template for PCR amplification, a plasmid such as pRcCMV-3D6LC (Rüker F, et al. Ann N Y Acad Sci. 1991 Dec. 27; 646:212-9), which contains as an insert the complete light chain of the human monoclonal antibody, is used.

For the CL+3 (SEQ ID No. 50, 51) and the CL+5 (SEQ ID No. 52, 53) libraries, which contain additional residues inserted between position 92 and 95 of the CL domain, primer CLRHPY3 and CLRHPY5 are used respectively instead of primer CLRHPY.

The nucleotide and amino acid sequence of the final product of the PCRs and ligations, cloned into the NcoI site of pHEN1, which leads to the attachment of a pelB leader sequence to the N-terminus of the construct is shown below (SEQ ID No. 48, 49):

```
+3         M   K   Y   L   L   P   T   A   A   A   G   L   L   L   L   A   A
 1        ATGAAATACC TATTGCCTAC GGCAGCCGCT GGATTGTTAT TACTCGCGGC

NcoI
+3         Q   P   A   M   A   V   A   A   P   S   V   F   I   F   P   P
51        CCAGCCGGCC ATGGCCGTGG CTGCACCATC TGTCTTCATC TTCCCGCCAT

+3         S       Q                       A   S   V   V   C   L   L   N
101       CTNNSNNSCA GNNSNNSNNS NNSNNSGCCT CTGTTGTGTG CCTGCTGAAT

+3         N   F   Y   P   R   E   A   K   V   Q   W   K   V   D   N   A   L
151       AACTTCTATC CCAGAGAGGC CAAAGTACAG TGGAAGGTGG ATAACGCCCT

+3         Q   S   G   N   S   Q   E   S   V   T   E   Q   D   S   K   D
201       CCAATCGGGT AACTCCCAGG AGAGTGTCAC AGAGCAGGAC AGCAAGGACA

HpyCH4IV
+3         S   T   Y   S   L   S   S   T   L   T   L           Y   E
251       GCACCTACAG CCTCAGCAGC ACCCTGACGTA TGNNSNNSNN SNNSTACGAG

+3         K   H   K   V   Y   A   C   E   V   T   H   Q   G   L   S   S   P
301       AAACACAAAG TCTACGCCTG CGAAGTCACC CATCAGGGCC TGAGCTCGCC

NotI
+3         V   T   K   S   F   N   R   G   E   A   A   A
351       CGTCACAAAG AGCTTCAACA GGGGAGAGGC GGCCGC
```

Primer List for CL Library:

cllnco:
(SEQ ID No. 56)
5'-cttaccatgg ccgtggctgc accatctgtc ttcatcttcc cgccatctnn snnscagnns nnsnnsnnsn nsgcctctgt tgtgtgc-3' cllhpy:
(SEQ ID No. 57)
5'-tgacaacgtc agggtgctgc tgaggc-3' clrhpy:
(SEQ ID No. 58)
5'-tcagaacgtt gnnsnnsnns nnstacgaga aacacaaagt c-3' clrhpy3:
(SEQ ID No. 59)
5'-tcagaacgtt gnnsnnsnns nnsnnsnnsn nstacgagaa acacaaagtc-3' clrhpy5:
(SEQ ID No. 60)
5'-tcagaacgtt gnnsnnsnns nnsnnsnnsn nsnnsnnsta cgagaaacac aaagtc-3' clrnot:
(SEQ ID No. 61)
5'-catcgcggcc gcctctcccc tgttgaagct c-3'

A number of selected library clones (mutated CL domains cloned in the phagmid vector pHEN1) are controlled by restriction analysis and by DNA sequencing to contain the insert as planned, including the correctly inserted randomized sequences. For the following steps of phage preparation, standard protocols are followed. Briefly, the ligation mixture is transformed into E. coli TG1 cells by electroporation. Subsequently, phage particles are rescued from E. coli TG1 cells with helper phage M13-KO7. Phage particles are then precipitated from culture supernatant with PEG/

NaCl in 2 steps, dissolved in water and used for selection by panning or, alternatively, they can be stored at minus 80° C.

Example 12: CH1 Library

Visual inspection of the crystal structure of an Fab fragment (the structure of the Fab of the human monoclonal antibody 3D6 is used: RSCB Protein Data Bank Entry 1DFB.PDB) and computer-aided analysis (Protein Explorer is used for this purpose) of the secondary and tertiary structure of this protein allows to identify residues located in loop regions which connect the beta-strands of the CH1-domain scaffold. These residues comprise amino acids 7 to 21, amino acids 25 to 39, amino acids 41 to 81, amino acids 83 to 85, amino acids 89 to 103 and amino acids 106 to 117 (numbering according to the IMGT numbering system).

More specifically, residues 12-19 and 93-100 are randomized within the human CH1 domain (SEQ ID No. 54, 55). Randomization is achieved by PCR amplification of the coding sequences with PCR primers in which the positions of the relevant codons are encoded by the nucleotide sequence 5'-NNS-3', which potentially encodes for all 20 amino acids while avoiding 2 out of 3 stop codons. The library insert is amplified by two separate PCR reactions, and the two PCR fragments are ligated together via a BstEII restriction site which occurs naturally in the CH1 domain. The primers further provide the restriction endonuclease sites NcoI and NotI respectively for cloning into the phage display vector pHEN. The C-terminal cystein of the CH1 domain is not included for the phage display, but can be added later on when a modified CH1 clone is used e.g. for the construction of an Fab fragment.

As a template for PCR amplification, a plasmid such as pRcCMV-3D6HC, which contains as an insert the complete heavy chain of the human monoclonal antibody, is used.

The nucleotide and amino acid sequence of the final product of the PCRs and ligations, cloned into the NcoI site of pHEN1, which leads to the attachment of a pelB leader sequence to the N-terminus of the construct is shown below (SEQ ID No. 54, 55):

Primer List for CH1 Library

```
CH1LNCO:
                                           (SEQ ID No. 62)
5'-acgtccatgg ccgcctccac caagggccca tcggtcttcc
ccctggcacc ctcctccnns nnsnnsnnsn nsnnsnnsnn
sgccctgggc tgcctggtc-3'

CH1LBST:
                                           (SEQ ID No. 63)
5'-ggcacggtca ccacgctgct gag-3'

CH1RBST:
                                           (SEQ ID No. 64)
5'-agcgtggtga ccgtgcccnn snnsnnsnns nnsnnsnnsa
cctacatctg caacgtgaat c-3'

CH1RNOT:
                                           (SEQ ID No. 65)
5'-catagoggcc gcagatttgg gctcaacttt cttgtc-3'
```

A number of selected library clones (mutated CH1 domains cloned in the phagmid vector pHEN1) are controlled by restriction analysis and by DNA sequencing to contain the insert as planned, including the correctly inserted randomized sequences. For the following steps of phage preparation, standard protocols are followed. Briefly, the ligation mixture is transformed into *E. coli* TG1 cells by electroporation. Subsequently, phage particles are rescued from *E. coli* TG1 cells with helper phage M13-KO7. Phage particles are then precipitated from culture supernatant with PEG/NaCl in 2 steps, dissolved in water and used for selection by panning or, alternatively, they can be stored at minus 80° C.

Example 13: Panning of the CH1-Phage Library on Hen Egg Lysozyme (HEL)

3 panning rounds are performed with the CH1-phage library (see example 12). Maxisorp 96-well plates (Nunc) are coated with hen egg lysozyme, by adding 200 µl of the following solution per well: PBS, with the following concentrations of dissolved hen egg lysozyme:

1$^{st}$ panning round: 2 mg/ml HEL
2$^{nd}$ panning round: 1 mg/ml HEL

```
+3    M   K   Y   L   L   P   T   A   A   A   G   L   L   L   L   A   A
  1   ATGAAATACC TATTGCCTAC GGCAGCCGCT GGATTGTTAT TACTCGCGGC

NcoI
+3    Q   P   A   M   A   A   S   T   K   G   P   S   V   F   P   L
 51   CCAGCCGGCC ATGGCCGCCT CCACCAAGGG CCCATCGGTC TTCCCCCTGG

+3    A   P   S   S                       A   L   G   C   L
101   CACCCTCCTC CNNSNNSNNS NNSNNSNNSN NSNNSGCCCT GGGCTGCCTG

+3    V   K   D   Y   F   P   E   P   V   T   V   S   W   N   S   G   A
151   GTCAAGGACT ACTTCCCCGA ACCGGTGACG GTGTCGTGGA ACTCAGGCGC

+3    L   T   S   G   V   H   T   F   P   A   V   L   Q   S   S   G
201   CCTGACCAGC GGCGTGCACA CCTTCCCGGC TGTCCTACAG TCCTCAGGAC

BstEII
+3    L   Y   S   L   S   S   V   V   T   V   P
251   TCTACTCCCT CAGCAGCGTG GTGACCGTGC CCNNSNNSNN SNNSNNSNNS

+3        T   Y   I   C   N   V   N   H   K   P   S   N   T   K   V   D
301   NNSACCTACA TCTGCAACGT GAATCACAAG CCCAGCAACA CCAAGGTGGA

NotI
+3    K   K   V   E   P   K   S   A   A   A
351   CAAGAAAGTT GAGCCCAAAT CTGCGGCCGC A
```

3$^{rd}$ panning round: 1 mg/ml HEL

Incubation is for 1 hour at 37° C., followed by blocking with 2% dry milk (M-PBS) with 200 µl per well for 1 hour at room temperature.

The surface display phage library is then allowed to react with the bound hen egg lysozyme by adding 100 µl phage suspension and 100 µl 4% dry milk (M-PBS), followed by incubation for 45 minutes with shaking and for 90 minutes without shaking at room temperature.

Unbound phage particles are washed away as follows:
1$^{st}$ panning round: 10×300 µl T-PBS, 5×300 µl PBS
2$^{nd}$ panning round: 15×300 µl T-PBS, 10×300 µl PBS
3$^{rd}$ panning round: 20×300 µl T-PBS, 20×300 µl PBS Elution of bound phage particles is performed by adding 200 µl per well of 0.1 M glycine, pH 2.2, and incubation with shaking for 30 minutes at room temperature. Subsequently, the phage suspension is neutralized by addition of 60 µl 2M Tris-Base, followed by infection into *E. coli* TG1 cells by mixture of 10 ml exponentially growing culture with 0.5 ml eluted phage and incubation for 30 minutes at 37° C. Finally, infected bacteria are plated on TYE medium with 1% glucose and 100 µg/ml ampicillin, and incubated at 30° C. overnight.

Cloning of Selected Clones of CH1 Mutants Selected Against Lysozyme for Soluble Expression Phagmid DNA from the phage selected through the 3 panning rounds is isolated with a midi-prep. DNA encoding mutated CH1-domains is batch-amplified by PCR and cloned NcoI-NotI into the vector pNOTBAD/Myc-His, which is the *E. coli* expression vector pBAD/Myc-His (Invitrogen) with an inserted NotI restriction site to facilitate cloning. Ligated constructs are transformed into *E. coli* LMG194 cells (Invitrogen) with electroporation, and grown at 30° C. on TYE medium with 1% glucose and ampicillin overnight. Selected clones are inoculated into 200 µl 2×YT medium with ampicillin, grown overnight at 30° C., and induced by adding L-arabinose to an end concentration of 0.1%. After expression at 16° C. overnight, the cells are harvested by centrifugation and treated with 100 µl Na-borate buffer, pH 8.0, at 4° C. overnight for preparation of periplasmic extracts. 50 µl of the periplasmic extracts are used in ELISA.

Clones that give a high signal in this first, preliminary ELISA are cultured in a 20-ml volume at the same conditions as described above. Their periplasmic extracts are isolated in 1/20 of the culture volume as described above and tested with ELISA (as described below) for confirmation.

ELISA of CH1 Mutants Selected Against Hen Egg Lysozyme

Coating: Microtiter plate (NUNC, Maxisorp), 100 µl per well, 100 µg hen egg lysozyme/ml in PBS, 1 h at 37° C.
Wash: 3×200 µl PBS
Blocking: 1% BSA-PBS, 1 h at RT
Wash: 3×200 µl PBS
Periplasmic extract binding: 50 µl periplasmic extract
50 µl 2% BSA-PBS, at room temperature overnight
Wash: 3×200 µl PBS
1$^{st}$ antibody: anti-His$_4$ (Qiagen), 1:1000 in 1% BSA-PBS, 90 min at RT, 100 µl per well
Wash: 3×200 µl PBS
2$^{nd}$ antibody: goat anti mouse*HRP (SIGMA), 1:1000 in 1% BSA-PBS, 90 min at RT, 100 µl per well
Wash: 3×200 µl PBS
Detection: 3 mg/ml OPD in Na-citrate/phosphate buffer, pH 4.5, 0.4 µl 30% H$_2$O$_2$
Stopping: 100 ml 3M H$_2$SO$_4$
Absorbance read: 492/620 nm Clones are interpreted as positive when their ELISA signal is at least three times that of the background signal.

Example 14: Panning of the CL-Phage Library on Hen Egg Lysozyme (HEL)

3 panning rounds are performed with the CL-phage library (see example 11). Maxisorp 96-well plates (Nunc) are coated with hen egg lysozyme, by adding 200 µl of the following solution per well: PBS, with the following concentrations of dissolved hen egg lysozyme:
1$^{st}$ panning round: 2 mg/ml HEL
2$^{nd}$ panning round: 1 mg/ml HEL
3$^{rd}$ panning round: 1 mg/ml HEL Incubation is for 1 hour at 37° C., followed by blocking with 2% dry milk (M-PBS) with 200 µl per well for 1 hour at room temperature.

The surface display phage library is then allowed to react with the bound hen egg lysozyme by adding 100 µl phage suspension and 100 µl 4% dry milk (M-PBS), followed by incubation for 45 minutes with shaking and for 90 minutes without shaking at room temperature.

Unbound phage particles are washed away as follows:
1$^{st}$ panning round: 10×300 µl T-PBS, 5×300 µl PBS
2$^{nd}$ panning round: 15×300 µl T-PBS, 10×300 µl PBS
3$^{rd}$ panning round: 20×300 µl T-PBS, 20×300 µl PBS Elution of bound phage particles is performed by adding 200 µl per well of 0.1 M glycine, pH 2.2, and incubation with shaking for 30 minutes at room temperature. Subsequently, the phage suspension is neutralized by addition of 60 µl 2M Tris-Base, followed by infection into *E. coli* TG1 cells by mixture of 10 ml exponentially growing culture with 0.5 ml eluted phage and incubation for 30 minutes at 37° C. Finally, infected bacteria are plated on TYE medium with 1% glucose and 100 µg/ml Ampicillin, and incubated at 30° C. overnight.

Cloning of Selected Clones of CL Mutants Selected Against Lysozyme for Soluble Expression Phagmid DNA from the phage selected through the 3 panning rounds is isolated with a midi-prep. DNA encoding mutated CL-domains is batch-amplified by PCR and cloned NcoI-NotI into the vector pNOTBAD/Myc-His, which is the *E. coli* expression vector pBAD/Myc-His (Invitrogen) with an inserted NotI restriction site to facilitate cloning. Ligated constructs are transformed into *E. coli* LMG194 cells (Invitrogen) with electroporation, and grown at 30° C. on TYE medium with 1% glucose and ampicillin overnight. Selected clones are inoculated into 200 µl 2×YT medium with ampicillin, grown overnight at 30° C., and induced by adding L-arabinose to an end concentration of 0.1%. After expression at 16° C. overnight, the cells are harvested by centrifugation and treated with 100 µl Na-borate buffer, pH 8.0, at 4° C. overnight for preparation of periplasmic extracts. 50 µl of the periplasmic extracts are used in ELISA.

Clones that give a high signal in this first, preliminary ELISA are cultured in a 20-ml volume at the same conditions as described above. Their periplasmic extracts are isolated in 1/20 of the culture volume as described above and tested with ELISA (as described below) for confirmation.

ELISA of CL Mutants Selected Against Hen Egg Lysozyme

Coating: Microtiter plate (NUNC, Maxisorp), 100 µl per well, 100 µg hen egg lysozyme/ml in PBS, 1 h at 37° C.
Wash: 3×200 µl PBS
Blocking: 1% BSA-PBS, 1 h at RT Wash: 3×200 μl PBS
Periplasmic extract binding: 50 μl periplasmic extract
  50 μl 2% BSA-PBS, at room temperature overnight
  Wash: 3×200 μl PBS
$1^{st}$ antibody: anti-His$_4$ (Qiagen), 1:1000 in 1% BSA-PBS, 90 min at RT, 100 μl per well
Wash: 3×200 μl PBS
$2^{nd}$ antibody: goat anti mouse*HRP (SIGMA), 1:1000 in 1% BSA-PBS, 90 min at RT, 100 μl per well
Wash: 3×200 μl PBS
Detection: 3 mg/ml OPD in Na-citrate/phosphate buffer, pH 4.5, 0.4 μl 30% $H_2O_2$
Stopping: 100 ml 3M $H_2SO_4$
Absorbance read: 492/620 nm
Clones are interpreted as positive when their ELISA signal is at least three times that of the background signal.

Example 15: Construction of an Immunoglobulin Domain which is Randomized on Both Sides (Bispecific Engineered $C_H3$ Domain)

This example describes an engineered immunoglobulin domain with two binding specificities.
The design of this engineered immunoglobulin domain comprised the following strategy:
an engineered $C_H3$ domain, clone C24 (see example 10), derived from the $C_H3+5$ library binding specifically to lysozyme was used as starting point
residues to be randomized were identified in this modified CH3 domain which are connecting β-strands of the immunoglobulin fold, and which lie on the opposite side of the domain compared to the residues that were mutated when generating clone C24.
PCR primers were designed that allowed randomization of these residues and synthesis of this engineered immunoglobulin domain in a procedure similar to the one described above for the $C_H3$, the $C_H3+3$ and the $C_H3+5$ libraries.
4 PCR products containing randomised positions were ligated and full-length inserts were amplified by PCR. Subsequently, they were cloned in pHEN-1 via NcoI-NotI sites and transformed into E. coli TG-1 cells to construct the library of about $10^8$ colonies. 20 randomly chosen colonies were sequenced and randomised positions were found to be independently mutated. Also no "wild type" (C24) sequence was observed. The phage library was generated following standard protocols, and a phage titer of $6.32 \times 10^{10}$ TU/ml was achieved.
In order to test bispecificity, recombinant human Erythropoietin (rhEPO) was chosen as second antigen, while it was expected that the construct retained its originally engineered specificity for hen egg lysozyme. rhEPO-reactive phage was selected in 4 panning rounds. In order to preserve the population of C24 clones that after mutagenesis still should bind hen egg lysozyme, the first round of selection on rhEPO was followed by a round of panning of the phage population on hen egg lysozyme (1 mg/ml in PBS). 200 μl of rhEPO was coated on the 5 wells of microtitre plate (Maxisorp, Nunc) in 0.1 M Na-carbonate buffer, pH 9.6, in decreasing concentrations in subsequent panning rounds (see Table below). After blocking with 2% M-PBS, phage in the blocking agent was allowed to bind at room temperature for 2 h. After 20 washes with T-PBS and 20 with PBS, it was eluted with 0.1 M glycine, pH 2.2, and neutralised with 2M Tris. Eluted phage was used immediately to infect exponentially growing TG-1. Infected cells were selected on ampicilline-containing medium. Phage particles were rescued from culture supernatants upon superinfection with helper phage M13-KO7, concentrated with PEG and used in another panning round. Input and output phage numbers were determined as transforming units of E. coli after every panning round (Table 8).

TABLE 8

| panning round | antigen | phage input (TU/ml) | phage output (TU/ml) |
|---|---|---|---|
| 1 | rhEPO, 500 μg/ml | $6.32 \times 10^{10}$ | $1.9 \times 10^5$ |
| 2 | lysozyme, 1 mg/ml | $6.16 \times 10^{15}$ | $4.53 \times 10^{10}$ |
| 3 | rhEPO, 100 μg/ml | $6.07 \times 10^{15}$ | $6.78 \times 10^{10}$ |
| 4 | rhEPO, 50 μg/ml | $8.42 \times 10^{15}$ | $3.0 \times 10^{11}$ |
| 5 | rhEPO, 50 μg/ml | $5.12 \times 10^{15}$ | $4.28 \times 10^{10}$ |

Resulting colonies were scraped off the plates, cultured in 2×YT with ampicilline and their plasmid DNA was isolated with a midi-prep. Inserts were amplified with a PCR, and then subcloned into vector pNOTBAD and transformed into an E. coli strain E104. 4×72 colonies were cultured in 200 μl 2×YT with ampicilline and induced with 0.1% L-arabinose on the following day. After 24 h expression at 16° C., they were lysed with 200 μl Na-borate buffer, pH 8.0 for 6 h at 4° C. and periplasmic extract was used in ELISA.
For ELISA, Maxisorp plates were coated with hen egg lysozyme in PBS (20 μg/ml) or rhEPO in 0.1 M Na-carbonate buffer, pH 9.6, respectively, for 1 h at 37° C. After blocking with 1% BSA-PBS, periplasmic extract in the same blocking agent was allowed to bind overnight. Binding was revealed with an anti-His-(4) antibody and a goat anti-mouse IgG antibody, conjugated with HRP (for hen egg lysozyme detection) or AP (for rhEPO detection). Colour reaction of OPD conversion (HRP) was read at 492/620 nm after being stopped with 1.25 M $H_2SO_4$, and pNPP conversion (AP) was read at 405/620 nm. 14 clones with promising absorbance values were selected for expression at 20-ml-scale. After 24 h arabinose induction at 16° C., the cells were collected and lysed overnight in 1 ml Na-borate buffer at 4° C., and the lysate was used for ELISA. ELISA was performed as above in 4 parallels, and wells without periplasmic extract and without antigen were used as negative controls. Results (Table 9) were achieved with clone according to SEQ ID No. 42, 43.

TABLE 9

| antigen | | absorbance on binding | no periplasmic extract | no antigen |
|---|---|---|---|---|
| lysozyme | $A_{492/620\,nm}$ | 0.299 | 0.110 | 0.018 |
| rhEPO | $A_{405/620\,nm}$ | 0.258 | 0.095 | 0.090 |

Example 16: Engineered $C_H3$ Domains Provide Bispecificity in an Fab-Like Format In the construct used in this example, both the $V_L$ and the $V_H$ chain of an antibody are fused to an engineered $C_H3$ domain.
The VL and VH region of the human monoclonal antibody 3D6 (He X M, et al. Proc Natl Acad Sci USA. 1992 89:7154-8.; Kohl J, et al. Ann N Y Acad Sci. 1991 646:106-14.; Felgenhauer M, et al. Nucleic Acids Res. 1990 18:4927), which recognizes an epitope on gp41 of HIV-1 was used as fusion partner for the engineered $C_H3$ domain clone C24 which binds specifically to hen egg lysozyme.

In order to promote the formation of the VL-CH3/VH-CH3 dimer via a disulfide bond, the residues Ser-Cys were added to the C-terminus of the C24 sequence.

The nucleotide- and amino acid sequences respectively of the two chains, 3D6VL-C24 and 3D6VH-C24 are given in SEQ ID No. 47, 46 and SEQ ID No. 45, 44, respectively.

Primers were designed that allow the amplification of the coding regions, introducing restriction sites at the same time (silent mutations) which were used to ligate the coding regions together. For expression of the genes, the *Pichia pastoris* expression system was chosen. Constructs were cloned in suitable *Pichia pastoris* expression vectors: 3D6VL-C24 was cloned in the pPIC9K (final name: pPIC9K3LC) and 3D6VH-C24 (final name: pPICZ3HC) was cloned in pPICZalphaA. Construct pPICZ3HC was linearized with Bgl II, transformed into *Pichia pastoris* GS115 and transformants were selected on zeocin-containing solid medium. One of the transformants was subsequently used as a host cell for the Sal I-linearized construct pPIC9K3LC. Double transformants were then selected on RDB-medium.

Clones were inoculated into 30 ml YPG medium and grown until $OD_{600}$=10, and were then induced by the addition of 1% methanol in BMMY medium. The induction was continued for 36 hours at 16° C. Supernatants were removed by centrifugation and were then concentrated about 10-times. Presence of the recombinant protein was confirmed by a Western blot with an anti-His (4) antibody, and was estimated to be at a concentration of approximately 50-100 µg/l initial culture.

First functional tests were performed with 10×-concentrated supernatant. Firstly, wells of Maxisorp plates were coated with 20 µg/ml hen egg lysozyme in PBS or 20 µg/ml epitope of the antibody 3D6 in 0.1 M Na-carbonate buffer, pH 9.6, respectively, for 1 h at 37° C. The 3D6 epitope was used in the form of a recombinantly produced GST-fusion protein. After blocking with 1% BSA-PBS, concentrated supernatants were allowed to bind overnight in the same blocking agent. Binding was revealed with an anti-His (4) antibody and goat anti-mouse antibody, conjugated to HRP, and visualised as colour reaction resulting from OPD conversion at 492/620 nm (Table 10).

TABLE 10

| antigen | ELISA signal ($A_{492/620}$) | Background (no antigen) | Background (no supernatant) |
|---|---|---|---|
| lysozyme | 0.198 | 0.003 | 0.043 |
| 3D6 epitope | 0.061 | 0.001 | 0.007 |

The invention claimed is:

1. A polypeptide scaffold comprising an immunoglobulin fold of a constant domain comprising six structural loops connected by beta strands, three of said six structural loops corresponding to three structural loops of a human IgG1 constant region CH3 domain, said three structural loops of said human IgG1 constant region CH3 domain consisting of the AB loop (positions 17-19 of SEQ ID NO:1), the CD loop (positions 44-47 of SEQ ID NO:1), and the EF loop (positions 71-73 and 76-77 of SEQ ID NO:1), wherein said scaffold comprises an amino acid sequence which is 85% identical to amino acids 1-104 of SEQ ID NO: 1; and wherein said scaffold comprises a minimum number of residues which differ from corresponding residues of SEQ ID NO: 1 selected from the group consisting of:

a) wherein two or more of said three structural loops of said scaffold comprise a total of at least three residues which are different from corresponding residues of SEQ ID NO: 1;

and/or b) wherein one of said three structural loops of said scaffold comprise at least four residues which are different from corresponding residues of SEQ ID NO: 1; and wherein said structural loops of (a) and (b) of said polypeptide scaffold form a solvent accessible surface.

2. The polypeptide scaffold of claim 1, wherein scaffold comprises an amino acid sequence which is 90% identical to amino acids 1-96 of SEQ ID NO: 1.

3. The polypeptide scaffold of claim 1, wherein scaffold comprises an amino acid sequence which is 95% identical to amino acids 1-96 of SEQ ID NO: 1.

4. The polypeptide scaffold of claim 1, wherein in (a) each of said two or more of said three structural loops of said scaffold comprises at least three residues which are different from corresponding residues of SEQ ID NO: 1.

5. The polypeptide scaffold of claim 1, wherein said structural loops of (a) and (b) of claim 1 do not comprise an inserted peptide of predetermined sequence that specifically binds an epitope independently of its insertion into said structural loops of (a) and/or (b).

6. The polypeptide scaffold of claim 1, wherein said scaffold comprises an amino acid sequence selected from the group consisting of: SEQ ID NO: 16, 18, 20, 22, 24, 26, 28, 30, 32, 34, 36, 38, 40 and 42.

* * * * *

SEQUENCE LISTING

```
<160> NUMBER OF SEQ ID NOS: 67

<210> SEQ ID NO 1
<211> LENGTH: 108
<212> TYPE: PRT
<213> ORGANISM: Homo sapiens

<400> SEQUENCE: 1

Pro Arg Glu Pro Gln Val Tyr Thr Leu Pro Pro Ser Arg Asp Glu Leu
1               5                   10                  15

Thr Lys Asn Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60

Tyr Ser Lys Leu Thr Val Asp Lys Ser Arg Trp Gln Gln Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Pro Gly Lys Ala Ala Ala
            100                 105

<210> SEQ ID NO 2
<211> LENGTH: 332
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t
```

```
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (219)..(220)
<223> OTHER INFORMATION: n is a, c, g, or t
<220> FEATURE:
<221> NAME/KEY: misc_feature
<222> LOCATION: (222)..(223)
<223> OTHER INFORMATION: n is a, c, g, or t
<220> FEATURE:
<221> NAME/KEY: misc_feature
<222> LOCATION: (225)..(226)
<223> OTHER INFORMATION: n is a, c, g, or t
<220> FEATURE:
<221> NAME/KEY: misc_feature
<222> LOCATION: (234)..(235)
<223> OTHER INFORMATION: n is a, c, g, or t
<220> FEATURE:
<221> NAME/KEY: misc_feature
<222> LOCATION: (237)..(238)
<223> OTHER INFORMATION: n is a, c, g, or t

<400> SEQUENCE: 2
ccatggcccc cgagaaacca caggtgtaca ccctgccccc atcccgggat gagctcnnsn      60
nsnnscaggt cagcctgacc tgcctggtca aaggcttcta tcccagcgac atcgccgtgg     120
agtgggagag caatgggcag ccggagaaca actacaagac cacgcctccc gtgctggact     180
ccgacggctc cttcttcctc tacagcaagc ttaccgtgnn snnsnnsagg tggnnsnnsg     240
ggaacgtctt ctcatgctcc gtgatgcatg aggctctgca caaccactac acacagaaga     300
gcctctccct gtctccgggt aaagcggccg ca                                   332

<210> SEQ ID NO 3
<211> LENGTH: 110
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (19)..(21)
<223> OTHER INFORMATION: Xaa can be any naturally occurring amino acid
<220> FEATURE:
<221> NAME/KEY: misc_feature
<222> LOCATION: (73)..(75)
<223> OTHER INFORMATION: Xaa can be any naturally occurring amino acid
<220> FEATURE:
<221> NAME/KEY: misc_feature
<222> LOCATION: (78)..(79)
<223> OTHER INFORMATION: Xaa can be any naturally occurring amino acid

<400> SEQUENCE: 3

Met Ala Pro Arg Glu Pro Gln Val Tyr Thr Leu Pro Pro Ser Arg Asp
1               5                   10                  15

Glu Leu Xaa Xaa Xaa Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Xaa Xaa Xaa Arg Trp Xaa Xaa Gly
65                  70                  75                  80

Asn Val Phe Ser Cys Ser Val Met His Glu Ala Leu His Asn His Tyr
                85                  90                  95
```

Thr Gln Lys Ser Leu Ser Leu Ser Pro Gly Lys Ala Ala Ala
            100                 105                 110

<210> SEQ ID NO 4
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 4
cttgccatgg ccccccgaga accacaggtg tac                               33

<210> SEQ ID NO 5
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 5
agtcgagctc gtcacgggat gggggcaggg                                  30

<210> SEQ ID NO 6
<211> LENGTH: 41
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t

<400> SEQUENCE: 6
gtacgagctc nnsnnsnnsc aagtcagcct gacctgcctg g                     41

<210> SEQ ID NO 7
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 7
tgccaagctt gctgtagagg aagaaggagc cg                               32

<210> SEQ ID NO 8
<211> LENGTH: 59
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:

```
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 8
tgccaagctt accgtgnnsn nsnnsaggtg gnnsnnsggg aacgtcttct catgctccg      59

<210> SEQ ID NO 9
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 9
agttgcggcc gctttacccg gagacaggga gag                                 33

<210> SEQ ID NO 10
<211> LENGTH: 113
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (19)..(21)
<223> OTHER INFORMATION: Xaa can be any naturally occurring amino acid
<220> FEATURE:
<221> NAME/KEY: misc_feature
<222> LOCATION: (73)..(78)
<223> OTHER INFORMATION: Xaa can be any naturally occurring amino acid
<220> FEATURE:
<221> NAME/KEY: misc_feature
<222> LOCATION: (81)..(82)
<223> OTHER INFORMATION: Xaa can be any naturally occurring amino acid

<400> SEQUENCE: 10

Met Ala Pro Arg Glu Pro Gln Val Tyr Thr Leu Pro Pro Ser Arg Asp
 1               5                  10                  15

Glu Leu Xaa Xaa Xaa Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
         50                  55                  60

Phe Leu Tyr Ser Lys Leu Thr Val Xaa Xaa Xaa Xaa Xaa Xaa Arg Trp
 65                  70                  75                  80

Xaa Xaa Gly Asn Val Phe Ser Cys Ser Val Met His Glu Ala Leu His
                85                  90                  95

Asn His Tyr Thr Gln Lys Ser Leu Ser Leu Ser Pro Gly Lys Ala Ala
            100                 105                 110

Ala

<210> SEQ ID NO 11
<211> LENGTH: 341
<212> TYPE: DNA
<213> ORGANISM: Artificial sequence
<220> FEATURE:
```

```
<223> OTHER INFORMATION: Synthetic oligonucleotide
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (219)..(220)
<223> OTHER INFORMATION: n is a, c, g, or t
<220> FEATURE:
<221> NAME/KEY: misc_feature
<222> LOCATION: (222)..(223)
<223> OTHER INFORMATION: n is a, c, g, or t
<220> FEATURE:
<221> NAME/KEY: misc_feature
<222> LOCATION: (225)..(226)
<223> OTHER INFORMATION: n is a, c, g, or t
<220> FEATURE:
<221> NAME/KEY: misc_feature
<222> LOCATION: (228)..(229)
<223> OTHER INFORMATION: n is a, c, g, or t
<220> FEATURE:
<221> NAME/KEY: misc_feature
<222> LOCATION: (231)..(232)
<223> OTHER INFORMATION: n is a, c, g, or t
<220> FEATURE:
<221> NAME/KEY: misc_feature
<222> LOCATION: (234)..(235)
<223> OTHER INFORMATION: n is a, c, g, or t
<220> FEATURE:
<221> NAME/KEY: misc_feature
<222> LOCATION: (243)..(244)
<223> OTHER INFORMATION: n is a, c, g, or t
<220> FEATURE:
<221> NAME/KEY: misc_feature
<222> LOCATION: (246)..(247)
<223> OTHER INFORMATION: n is a, c, g, or t

<400> SEQUENCE: 11
ccatggcccc ccgagaacca caggtgtaca ccctgccccc atcccgtgac gagctcnnsn      60
nsnnscaagt cagcctgacc tgcctggtca aaggcttcta tcccagcgac atcgccgtgg     120
agtgggagag caatgggcag ccggagaaca actacaagac cacgcctccc gtgctggact     180
ccgacggctc cttcttcctc tacagcaagc ttaccgtgnn snnsnnsnns nnsnnsaggt     240
ggnnsnnsgg gaacgtcttc tcatgctccg tgatgcatga ggctctgcac aaccactaca     300
cacagaagag cctctccctg tctccgggta aagcggccgc a                         341

<210> SEQ ID NO 12
<211> LENGTH: 68
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
```

```
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t

<400> SEQUENCE: 12
tgccaagctt accgtgnnsn nsnnsnnsnn snnsaggtgg nnsnnsggga acgtcttctc    60
atgctccg                                                            68

<210> SEQ ID NO 13
<211> LENGTH: 115
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (19)..(21)
<223> OTHER INFORMATION: Xaa can be any naturally occurring amino acid
<220> FEATURE:
<221> NAME/KEY: misc_feature
<222> LOCATION: (73)..(80)
<223> OTHER INFORMATION: Xaa can be any naturally occurring amino acid
<220> FEATURE:
<221> NAME/KEY: misc_feature
<222> LOCATION: (83)..(84)
<223> OTHER INFORMATION: Xaa can be any naturally occurring amino acid

<400> SEQUENCE: 13

Met Ala Pro Arg Glu Pro Gln Val Tyr Thr Leu Pro Pro Ser Arg Asp
1               5                   10                  15

Glu Leu Xaa Xaa Xaa Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Lys Leu Thr Val Xaa Xaa Xaa Xaa Xaa Xaa Xaa Xaa
65                  70                  75                  80

Arg Trp Xaa Xaa Gly Asn Val Phe Ser Cys Ser Val Met His Glu Ala
            85                  90                  95

Leu His Asn His Tyr Thr Gln Lys Ser Leu Ser Leu Ser Pro Gly Lys
            100                 105                 110

Ala Ala Ala
        115

<210> SEQ ID NO 14
<211> LENGTH: 347
<212> TYPE: DNA
<213> ORGANISM: Artificial sequence
<220> FEATURE:
```

```
<223> OTHER INFORMATION: Synthetic oligonucleotide
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (219)..(220)
<223> OTHER INFORMATION: n is a, c, g, or t
<220> FEATURE:
<221> NAME/KEY: misc_feature
<222> LOCATION: (222)..(223)
<223> OTHER INFORMATION: n is a, c, g, or t
<220> FEATURE:
<221> NAME/KEY: misc_feature
<222> LOCATION: (225)..(226)
<223> OTHER INFORMATION: n is a, c, g, or t
<220> FEATURE:
<221> NAME/KEY: misc_feature
<222> LOCATION: (228)..(229)
<223> OTHER INFORMATION: n is a, c, g, or t
<220> FEATURE:
<221> NAME/KEY: misc_feature
<222> LOCATION: (231)..(232)
<223> OTHER INFORMATION: n is a, c, g, or t
<220> FEATURE:
<221> NAME/KEY: misc_feature
<222> LOCATION: (234)..(235)
<223> OTHER INFORMATION: n is a, c, g, or t
<220> FEATURE:
<221> NAME/KEY: misc_feature
<222> LOCATION: (237)..(238)
<223> OTHER INFORMATION: n is a, c, g, or t
<220> FEATURE:
<221> NAME/KEY: misc_feature
<222> LOCATION: (240)..(241)
<223> OTHER INFORMATION: n is a, c, g, or t
<220> FEATURE:
<221> NAME/KEY: misc_feature
<222> LOCATION: (249)..(250)
<223> OTHER INFORMATION: n is a, c, g, or t
<220> FEATURE:
<221> NAME/KEY: misc_feature
<222> LOCATION: (252)..(253)
<223> OTHER INFORMATION: n is a, c, g, or t

<400> SEQUENCE: 14
ccatggcccc ccgagaacca caggtgtaca ccctgccccc atcccgtgac gagctcnnsn      60
nsnnscaagt cagcctgacc tgcctggtca aaggcttcta tcccagcgac atcgccgtgg     120
agtgggagag caatgggcag ccggagaaca actacaagac cacgcctccc gtgctggact     180
ccgacggctc cttcttcctc tacagcaagc ttaccgtgnn snnsnnsnns nnsnnsnnsn     240
nsaggtggnn snnsgggaac gtcttctcat gctccgtgat gcatgaggct ctgcacaacc     300
actacacaca gaagagcctc tccctgtctc cgggtaaagc ggccgca                   347

<210> SEQ ID NO 15
<211> LENGTH: 74
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (17)..(18)
<223> OTHER INFORMATION: n is a, c, g, or t
```

```
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t

<400> SEQUENCE: 15
tgccaagctt accgtgnnsn nsnnsnnsnn snnsnnsnns aggtggnnsn nsgggaacgt    60
cttctcatgc tccg                                                     74

<210> SEQ ID NO 16
<211> LENGTH: 110
<212> TYPE: PRT
<213> ORGANISM: Artificial sequence
<220> FEATURE:
<223> OTHER INFORMATION: Synthetic peptide

<400> SEQUENCE: 16

Pro Arg Glu Pro Gln Val Tyr Thr Leu Pro Pro Ser Arg Asp Glu Leu
1               5                   10                  15

Gly Trp Pro Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60

Tyr Ser Lys Leu Thr Val Pro Lys Arg Trp Cys Val Ser Val Arg Trp
65                  70                  75                  80

Pro Pro Gly Asn Val Phe Ser Cys Ser Val Met His Glu Ala Leu His
                85                  90                  95

Asn His Tyr Thr Gln Lys Ser Leu Ser Leu Ser Pro Gly Lys
            100                 105                 110

<210> SEQ ID NO 17
<211> LENGTH: 330
<212> TYPE: DNA
<213> ORGANISM: Artificial sequence
```

<220> FEATURE:
<223> OTHER INFORMATION: Synthetic oligonucleotide

<400> SEQUENCE: 17

```
ccccgagaac cacaggtgta caccctgccc ccatcccgtg acgagctcgg ctggccgcaa        60
gtcagcctaa cctgcctggt caaaggcttc tatcccagcg acatcgccgt ggagtgggag       120
agcaatgggc agccggagaa caactacaag accacgcctc ccgtgctgga ctccgacggc       180
tccttcttcc tctacagcaa gcttaccgtg cccaagcggt ggtgcgtgag cgtcaggtgg       240
cccccgggga acgtcttctc atgctccgtg atgcatgagg ctctgcacaa ccactacaca       300
cagaagagcc tctccctgtc tccgggtaaa                                        330
```

<210> SEQ ID NO 18
<211> LENGTH: 110
<212> TYPE: PRT
<213> ORGANISM: Artificial sequence
<220> FEATURE:
<223> OTHER INFORMATION: Synthetic peptide

<400> SEQUENCE: 18

```
Pro Arg Glu Pro Gln Val Tyr Thr Leu Pro Pro Ser Arg Asp Glu Leu
1               5                   10                  15
Ser Val Ser Gln Val Ser Pro Thr Cys Leu Val Lys Gly Phe Tyr Pro
                20                  25                  30
Ser Asp Ile Ala Val Glu Trp Glu Ser Asn Gly Gln Pro Glu Asn Asn
            35                  40                  45
Tyr Lys Thr Thr Pro Pro Val Leu Asp Ser Asp Gly Ser Phe Phe Leu
        50                  55                  60
Tyr Ser Lys Leu Thr Val Ile Pro Phe Cys Arg Met Ser Pro Arg Trp
65                  70                  75                  80
Trp Ile Gly Asn Val Phe Ser Cys Ser Val Met His Glu Ala Leu His
                85                  90                  95
Asn His Tyr Thr Gln Lys Ser Leu Ser Leu Ser Pro Gly Lys
                100                 105                 110
```

<210> SEQ ID NO 19
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 19

```
ccccgagaac cacaggtgta caccctgccc ccatcccgtg acgagctctc ggtgtcgcaa        60
gtcagcccga cctgcctggt caaaggcttc tatcccagcg acatcgcagt ggagtgggag       120
agcaatgggc agccggagaa caactacaag accacgcctc ccgtgctgga ctccgacggc       180
tccttcttcc tctacagcaa gcttaccgtg atcccttct gcaggatgag ccccaggtgg       240
tggatcggga acgtcttctc atgctccgtg atgcatgagg ctctgcacaa ccactacaca       300
cagaagagcc tctccctgtc tccgggtaaa                                        330
```

<210> SEQ ID NO 20
<211> LENGTH: 105
<212> TYPE: PRT
<213> ORGANISM: Artificial sequence
<220> FEATURE:
<223> OTHER INFORMATION: Synthetic peptide

<400> SEQUENCE: 20

```
Pro Arg Glu Pro Gln Val Tyr Thr Leu Pro Pro Ser Arg Asp Glu Leu
1               5                   10                  15

Glu Ala Leu Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
50                  55                  60

Tyr Ser Lys Leu Thr Val Arg Arg Asn Arg Trp Ser Trp Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Pro Gly Lys
                100                 105
```

<210> SEQ ID NO 21
<211> LENGTH: 315
<212> TYPE: DNA
<213> ORGANISM: Artificial sequence
<220> FEATURE:
<223> OTHER INFORMATION: Synthetic oligonucleotide

<400> SEQUENCE: 21

```
cctcgagaac acaggtgta caccctgccc ccatcccgtg acgagctcga ggcgctgcaa     60
gtcagcctga cctgcctggt caaaggcttc tatcccagcg acatcgccgt ggagtgggag    120
agcaatgggc agccggagaa caactacaag accacgcctc ccgtgctgga ctccgacggc    180
tccttcttcc tctacagcaa gcttaccgtg cggcgcaaca ggtggtcctg ggggaacgtc    240
ttctcatgct ccgtgatgca tgaggctctg cacaaccact acacacagaa gagcctctcc    300
ctgtctccgg gtaaa                                                     315
```

<210> SEQ ID NO 22
<211> LENGTH: 108
<212> TYPE: PRT
<213> ORGANISM: Artificial sequence
<220> FEATURE:
<223> OTHER INFORMATION: Synthetic peptide

<400> SEQUENCE: 22

```
Pro Arg Glu Pro Gln Val Tyr Thr Leu Pro Pro Ser Arg Asp Glu Leu
1               5                   10                  15

Gln Gly Ser Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
50                  55                  60

Tyr Ser Lys Leu Thr Val Lys Ser Arg Ala Thr Arg Arg Trp Val Val
65                  70                  75                  80

Gly Asn Val Phe Ser Cys Ser Val Met His Glu Ala Leu His Asn His
                85                  90                  95

Tyr Thr Gln Lys Asn Leu Ser Leu Ser Pro Gly Lys
                100                 105
```

<210> SEQ ID NO 23
<211> LENGTH: 324
<212> TYPE: DNA

<213> ORGANISM: Artificial sequence
<220> FEATURE:
<223> OTHER INFORMATION: Synthetic oligonucleotide

<400> SEQUENCE: 23

```
ccccgagaac cacaggtgta caccctgccc ccatcccgtg acgagctcca ggggagccaa    60
gtcagcctga cctgcctggt caaaggcttc tatcccagcg acatcgccgt ggagtgggag   120
agcaatgggc agccggagaa caactacaag accacgcctc ccgtgctgga ctccgacggc   180
tccttcttcc tctacagcaa gcttaccgtg aagtcgcgcg ccacccggag gtgggtggtg   240
gggaacgtct tttcttgctc cgtgatgcat gaggctctgc acaaccacta cacacagaag   300
aacctctccc tgtctccggg taaa                                          324
```

<210> SEQ ID NO 24
<211> LENGTH: 107
<212> TYPE: PRT
<213> ORGANISM: Artificial sequence
<220> FEATURE:
<223> OTHER INFORMATION: Synthetic peptide

<400> SEQUENCE: 24

```
Pro Arg Glu Pro Gln Val Tyr Thr Leu Pro Pro Ser Arg Asp Glu Leu
1               5                   10                  15
Ala Ile Gly Gln Val Ser Leu Thr Cys Leu Val Lys Gly Phe Tyr Pro
            20                  25                  30
Ser Asp Ile Ala Val Glu Trp Glu Ser Asn Gly Gln Pro Glu Asn Asn
        35                  40                  45
Tyr Lys Thr Thr Pro Pro Val Leu Asp Ser Asp Gly Ser Phe Phe Leu
    50                  55                  60
Tyr Ser Lys Leu Thr Val Arg Ser Thr Arg Asp Asn Arg Trp Leu Val
65                  70                  75                  80
Gly Asn Val Phe Ser Cys Ser Val Met His Glu Ala Leu His Asn His
                85                  90                  95
Tyr Thr Gln Lys Ser Leu Ser Leu Ser Pro Gly
            100                 105
```

<210> SEQ ID NO 25
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 25

```
ccccgagaac cacaggtgta caccctgccc ccatcccgtg acgagctcgc gatcggccaa    60
gtcagcctga cctgcctggt caaaggcttc tatcccagcg acatcgccgt ggagtgggag   120
agcaatgggc agccggagaa caactacaag accacgcctc ccgtgctgga ctccgacggc   180
tccttcttcc tctacagcaa gcttaccgtg cgctcgacga gggacaacag gtggctggtg   240
gggaacgtct tctcatgctc cgtgatgcat gaggctctgc acaaccacta cacacagaag   300
agcctctccc tgtctccggg taaa                                          324
```

<210> SEQ ID NO 26
<211> LENGTH: 110
<212> TYPE: PRT
<213> ORGANISM: Artificial sequence
<220> FEATURE:
<223> OTHER INFORMATION: Synthetic peptide

<400> SEQUENCE: 26

Pro Arg Glu Pro Gln Val Tyr Thr Leu Pro Pro Ser Arg Asp Glu Leu
1               5                   10                  15

Ser Gly Ala Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
50                  55                  60

Tyr Ser Lys Leu Thr Val Trp Phe Arg Gln Glu Gly Gly Met Arg Trp
65                  70                  75                  80

Phe Ala Gly Asn Val Phe Ser Cys Ser Val Met His Glu Ala Leu His
                85                  90                  95

Asn His Tyr Thr Gln Lys Ser Leu Ser Leu Ser Pro Gly Lys
            100                 105                 110

<210> SEQ ID NO 27
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 27
ccccgagaac acaggtgta caccctgccc ccatcccgtg acgagctcag cggggcgcaa      60
gtcagcctga cctgcctggt caaaggcttc tatcccagcg acatcgccgt ggagtgggag     120
agcaatgggc agccggagaa caactacaag accacgcctc ccgtgctgga ctccgacggc    180
tccttcttcc tctacagcaa gcttaccgtg tggttcaggc aggagggcgg catgaggtgg    240
ttcgcgggga acgtcttctc atgctccgtg atgcatgagg ctctgcacaa ccactacaca    300
cagaagagcc tctccctgtc tccgggtaaa                                     330

<210> SEQ ID NO 28
<211> LENGTH: 110
<212> TYPE: PRT
<213> ORGANISM: Artificial sequence
<220> FEATURE:
<223> OTHER INFORMATION: Synthetic peptide

<400> SEQUENCE: 28

Pro Arg Glu Pro Gln Val Tyr Thr Leu Pro Pro Ser Arg Asp Glu Leu
1               5                   10                  15

Val Leu Gly Gln Val Ser Pro Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
50                  55                  60

Tyr Gly Lys Leu Thr Val Pro Pro Arg Leu Lys Gly Trp Pro Arg Trp
65                  70                  75                  80

Gly Trp Gly Asn Val Phe Ser Cys Ser Val Met His Glu Ala Leu His
                85                  90                  95

Asn His Tyr Thr Gln Lys Ser Leu Ser Leu Ser Pro Gly Lys
            100                 105                 110

<210> SEQ ID NO 29
<211> LENGTH: 330

<212> TYPE: DNA
<213> ORGANISM: Artificial sequence
<220> FEATURE:
<223> OTHER INFORMATION: Synthetic oligonucleotide

<400> SEQUENCE: 29

```
ccccgagaac cacaggtgta caccctgccc ccatcccgtg acgagctcgt cttggggcaa    60
gtcagcccga cctgcctggt caaaggcttc tatcccagcg acatcgccgt ggagtgggag   120
agcaatgggc agccggagaa caactacaag accacgcctc ccgtgctgga ctccgacggc   180
tccttcttcc tctacggcaa gcttaccgtg ccccgcggt tgaagggctg ccgaggtgg     240
ggctggggga acgtcttctc atgctccgtg atgcatgagg ctctgcacaa ccactacaca   300
cagaagagcc tctccctgtc tccgggtaaa                                    330
```

<210> SEQ ID NO 30
<211> LENGTH: 105
<212> TYPE: PRT
<213> ORGANISM: Artificial sequence
<220> FEATURE:
<223> OTHER INFORMATION: Synthetic peptide

<400> SEQUENCE: 30

```
Pro Arg Glu Pro Gln Val Tyr Thr Leu Pro Pro Ser Arg Asp Glu Leu
1               5                   10                  15
Leu Ala Tyr Gln Val Ser Leu Thr Cys Leu Val Lys Gly Phe Tyr Pro
            20                  25                  30
Ser Asp Ile Ala Val Glu Trp Glu Ser Asn Gly Gln Pro Glu Asn Asn
        35                  40                  45
Tyr Lys Thr Thr Pro Pro Val Leu Asp Ser Asp Gly Ser Phe Phe Leu
    50                  55                  60
Tyr Ser Lys Leu Thr Val Val Ala Gly Arg Trp Thr Cys Gly Asn Val
65                  70                  75                  80
Phe Ser Cys Ser Val Met His Glu Ala Leu His Asn His Tyr Thr Gln
                85                  90                  95
Lys Ser Leu Ser Leu Ser Pro Gly Lys
            100                 105
```

<210> SEQ ID NO 31
<211> LENGTH: 315
<212> TYPE: DNA
<213> ORGANISM: Artificial sequence
<220> FEATURE:
<223> OTHER INFORMATION: Synthetic oligonucleotide

<400> SEQUENCE: 31

```
ccccgagaac cacaggtgta caccctgccc ccatcccgtg acgagctcct ggcgtaccaa    60
gtcagcctga cctgcctggt caaaggcttc tatcccagcg acatcgccgt ggagtgggag   120
agcaatgggc agccggagaa caactacaag accacgcctc ccgtgctgga ctccgacggc   180
tccttcttcc tctacagcaa gcttaccgtg gtggccggca ggtggacgtg cgggaacgtc   240
ttctcatgct ccgtgatgca tgaggctctg cacaaccact acacacagaa gagcctctcc   300
ctgtctccgg gtaaa                                                    315
```

<210> SEQ ID NO 32
<211> LENGTH: 110
<212> TYPE: PRT
<213> ORGANISM: Artificial sequence
<220> FEATURE:
<223> OTHER INFORMATION: Synthetic peptide

<400> SEQUENCE: 32

Pro Arg Glu Pro Gln Val Tyr Thr Leu Pro Pro Ser Arg Asp Glu Leu
1               5                   10                  15

Cys Val Pro Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60

Tyr Ser Lys Leu Thr Val Val Leu Lys Val Val Gln Ala Arg Arg Trp
65                  70                  75                  80

Glu Val Gly Asn Val Phe Ser Cys Ser Val Met His Glu Ala Leu His
                85                  90                  95

Asn His Tyr Thr Gln Lys Ser Leu Ser Leu Ser Pro Gly Lys
            100                 105                 110

<210> SEQ ID NO 33
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 33
ccccgagaac acaggtgta caccctgccc ccatcccgtg acgagctctg cgtcccgcaa      60
gtcagcctga cctgcctggt caaaggcttc tatcccagcg acatcgccgt ggagtgggag     120
agcaatgggc agccggagaa caactacaag accacgcctc ccgtgctgga ctccgacggc    180
tccttcttcc tctacagcaa gcttaccgtg gtgctcaagg tcgtgcaggc gcgcaggtgg    240
gaggtgggga acgtcttctc atgctccgtg atgcatgagg ctctgcacaa ccactacaca    300
cagaagagcc tctccctgtc tccgggtaaa                                     330

<210> SEQ ID NO 34
<211> LENGTH: 105
<212> TYPE: PRT
<213> ORGANISM: Artificial sequence
<220> FEATURE:
<223> OTHER INFORMATION: Synthetic peptide

<400> SEQUENCE: 34

Pro Arg Glu Pro Gln Val Tyr Thr Leu Pro Pro Ser Arg Asp Glu Leu
1               5                   10                  15

Gly Ile Ala Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60

Tyr Ser Lys Leu Thr Val Leu Gly Arg Arg Trp Thr Leu Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Pro Gly Lys
            100                 105

<210> SEQ ID NO 35

<211> LENGTH: 315
<212> TYPE: DNA
<213> ORGANISM: Artificial sequence
<220> FEATURE:
<223> OTHER INFORMATION: Synthetic oligonucleotide

<400> SEQUENCE: 35

```
ccccgagaac cacaggtgta caccctgccc ccatcccggg acgagctcgg catcgcgcaa    60
gtcagcctga cctgcctggt caaaggcttc tatcccagcg acatcgccgt ggagtgggag   120
agcaacgggc agccggagaa caactacaag accacgcctc ccgtgctgga ctccgacggc   180
tccttcttcc tctacagcaa gcttaccgtg ttgggccgca ggtggaccct ggggaacgtc   240
ttctcatgct ccgtgatgca tgaggctctg cacaaccact acacacagaa gagcctctcc   300
ctgtctccgg gtaaa                                                    315
```

<210> SEQ ID NO 36
<211> LENGTH: 105
<212> TYPE: PRT
<213> ORGANISM: Artificial sequence
<220> FEATURE:
<223> OTHER INFORMATION: Synthetic peptide

<400> SEQUENCE: 36

```
Pro Arg Glu Pro Gln Val Tyr Thr Leu Pro Pro Ser Arg Asp Glu Leu
1               5                   10                  15
Gly Ile Ala Gln Val Ser Leu Thr Cys Leu Val Lys Gly Phe Tyr Pro
            20                  25                  30
Ser Asp Ile Ala Val Glu Trp Glu Ser Asn Gly Gln Pro Glu Asn Asn
        35                  40                  45
Tyr Lys Thr Thr Pro Pro Val Leu Asp Ser Asp Gly Ser Phe Phe Leu
    50                  55                  60
Tyr Ser Lys Leu Thr Val Leu Gly Arg Arg Trp Thr Leu Gly Asn Val
65                  70                  75                  80
Phe Ser Cys Ser Val Met His Glu Ala Leu His Asn His Tyr Thr Gln
                85                  90                  95
Lys Ser Leu Ser Leu Ser Pro Gly Lys
            100                 105
```

<210> SEQ ID NO 37
<211> LENGTH: 315
<212> TYPE: DNA
<213> ORGANISM: Artificial sequence
<220> FEATURE:
<223> OTHER INFORMATION: Synthetic oligonucleotide

<400> SEQUENCE: 37

```
ccccgagaac cacaggtgta caccctgccc ccatcccgtg acgagctcgg catcgcgcaa    60
gtcagcttga cctgcctggt caaaggcttt tatcccagcg acatcgccgt ggagtgggag   120
agcaacgggc agccggagaa caactacaag accacgcctc ccgtgctgga ctccgacggc   180
tccttcttcc tctacagcaa gcttaccgtg ttgggccgca ggtggaccct ggggaacgtc   240
ttctcatgct ccgtgatgca tgaggctctg cacaaccact acacacagaa gagcctctcc   300
ctgtctccgg gtaaa                                                    315
```

<210> SEQ ID NO 38
<211> LENGTH: 105
<212> TYPE: PRT
<213> ORGANISM: Artificial sequence
<220> FEATURE:

<223> OTHER INFORMATION: Synthetic peptide

<400> SEQUENCE: 38

Pro Arg Glu Pro Gln Val Tyr Thr Leu Pro Pro Ser Arg Asp Glu Leu
1               5                   10                  15

Leu Pro Cys Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60

Tyr Ser Lys Leu Thr Val Phe Cys Pro Arg Trp Leu Gly Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Pro Gly Lys
            100                 105

<210> SEQ ID NO 39
<211> LENGTH: 315
<212> TYPE: DNA
<213> ORGANISM: Artificial sequence
<220> FEATURE:
<223> OTHER INFORMATION: Synthetic oligonucleotide

<400> SEQUENCE: 39
ccccgagaac acaggtgta caccctgccc ccatcccgtg acgagctctt gccctgccaa      60
gtcagcctga cctgcctggt caaaggcttc tatcccagcg acatcgccgt ggagtgggag    120
agcaatgggc agccggagaa caactacaag accacgcctc ccgtgctgga ctccgacggc    180
tctttcttcc tctacagcaa gcttaccgtg ttctgcccca ggtggctggg ggggaacgtc    240
ttctcatgct ccgtgatgca tgaggctctg cacaaccact acacacagaa gagcctctcc    300
ctgtctccgg gtaaa                                                     315

<210> SEQ ID NO 40
<211> LENGTH: 105
<212> TYPE: PRT
<213> ORGANISM: Artificial sequence
<220> FEATURE:
<223> OTHER INFORMATION: Synthetic peptide

<400> SEQUENCE: 40

Pro Arg Glu Pro Gln Val Tyr Thr Leu Pro Pro Ser Arg Asp Glu Leu
1               5                   10                  15

Thr Lys Asn Gln Val Ser Leu Thr Cys Leu Val Lys Gly Phe Tyr Pro
            20                  25                  30

Ser Asp Ile Ala Val Glu Trp Glu Ser Asn Gly Gln Pro Glu Asn Asn
        35                  40                  45

Tyr Lys Thr Thr Pro Pro Val Leu Asp Ser Asp Gly Ser Phe Phe Leu
    50                  55                  60

Tyr Ser Lys Leu Thr Val Pro Cys Met Arg Trp Trp Gly Gly Asn Val
65                  70                  75                  80

Phe Ser Cys Ser Val Met His Glu Ala Leu His Asn His Tyr Thr Gln
                85                  90                  95

Lys Ser Leu Ser Leu Ser Pro Gly Lys
            100                 105

<210> SEQ ID NO 41
<211> LENGTH: 315
<212> TYPE: DNA
<213> ORGANISM: Artificial sequence
<220> FEATURE:
<223> OTHER INFORMATION: Synthetic oligonucleotide

<400> SEQUENCE: 41

```
ccccgagaac cacaggtgta caccctgccc ccatcccggg atgagctgac caagaaccag      60
gtcagcctga cctgcctggt caaaggcttc tatcccagcg acatcgccgt ggagtgggag     120
agcaatgggc agccggagaa caactacaag accacgcctc ccgtgctgga ctccgacggc     180
tccttcttcc tctacagcaa gcttaccgtg ccctgcatga ggtggtgggg cgggaacgtc     240
ttctcatgct ccgtgatgca tgaggctctg cacaaccact acacacagaa gagcctctcc     300
ctgtctccgg gtaaa                                                     315
```

<210> SEQ ID NO 42
<211> LENGTH: 115
<212> TYPE: PRT
<213> ORGANISM: Artificial sequence
<220> FEATURE:
<223> OTHER INFORMATION: Synthetic peptide

<400> SEQUENCE: 42

```
Arg Arg Glu Pro Gln Val Tyr Thr Leu Pro Pro Ser Arg Asp Glu Leu
1               5                   10                  15
Val Leu Gly Gln Val Ser Leu Ala Cys Leu Val Lys Gly Phe Val Val
            20                  25                  30
Arg Leu Ile Ala Val Glu Trp Glu Ser Asn Gly Gln Pro Glu Asn Asn
        35                  40                  45
Tyr Lys Thr Thr Pro Pro Val Leu Asp Ser Asp Gly Arg Gln Leu Ala
    50                  55                  60
Asp Ser Phe Phe Leu Tyr Ser Lys Leu Thr Val Pro Pro Arg Leu Lys
65                  70                  75                  80
Gly Trp Pro Arg Trp Gly Trp Gly Asn Val Phe Ser Cys Ser Val Met
                85                  90                  95
Phe Leu Ala Leu His Asn His Tyr Thr Gln Lys Ser Leu Ser Leu Ser
            100                 105                 110
Pro Gly Lys
        115
```

<210> SEQ ID NO 43
<211> LENGTH: 345
<212> TYPE: DNA
<213> ORGANISM: Artificial sequence
<220> FEATURE:
<223> OTHER INFORMATION: Synthetic oligonucleotide

<400> SEQUENCE: 43

```
cggcgagaac cacaggtgta caccctgccc ccatcccgtg acgagctcgt cttggggcaa      60
gtcagcctgg cctgcctcgt gaaaggcttc gtggtccggt tgatcgccgt ggagtgggag     120
agcaatgggc agccggagaa caactacaag accacgcctc ccgttctaga ctccgacggc     180
cggcagttgg cggactcctt cttcctctac agcaagctta ccgtgccccc gcggttgaag     240
ggctggccga ggtggggctg ggggaacgtc ttctcatgca gtgtgatgtt cctggcgctg     300
cacaaccact acacacagaa gagcctctcc ctgtctccgg gtaaa                    345
```

<210> SEQ ID NO 44

<211> LENGTH: 238
<212> TYPE: PRT
<213> ORGANISM: Artificial sequence
<220> FEATURE:
<223> OTHER INFORMATION: Synthetic peptide

<400> SEQUENCE: 44

Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asn Asp Tyr
            20                  25                  30
Ala Met His Trp Val Arg Gln Ala Pro Gly Lys Gly Leu Glu Trp Val
        35                  40                  45
Ser Gly Ile Ser Trp Asp Ser Ser Ile Gly Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Met Ala Leu Tyr Tyr Cys
                85                  90                  95
Val Lys Gly Arg Asp Tyr Tyr Asp Ser Gly Gly Tyr Phe Thr Val Ala
            100                 105                 110
Phe Asp Ile Trp Gly Gln Gly Thr Met Val Thr Val Ser Ser Ala Ser
        115                 120                 125
Thr Lys Gly Pro Gln Val Tyr Thr Leu Pro Pro Ser Arg Asp Glu Leu
    130                 135                 140
Val Leu Gly Gln Val Ser Pro Thr Cys Leu Val Lys Gly Phe Tyr Pro
145                 150                 155                 160
Ser Asp Ile Ala Val Glu Trp Glu Ser Asn Gly Gln Pro Glu Asn Asn
                165                 170                 175
Tyr Lys Thr Thr Pro Pro Val Leu Asp Ser Asp Gly Ser Phe Phe Leu
            180                 185                 190
Tyr Gly Lys Leu Thr Val Pro Pro Arg Leu Lys Gly Trp Pro Arg Trp
        195                 200                 205
Gly Trp Gly Asn Val Phe Ser Cys Ser Val Met His Glu Ala Leu His
    210                 215                 220
Asn His Tyr Thr Gln Lys Ser Leu Ser Leu Ser Pro Gly Lys
225                 230                 235

<210> SEQ ID NO 45
<211> LENGTH: 714
<212> TYPE: DNA
<213> ORGANISM: Artificial sequence
<220> FEATURE:
<223> OTHER INFORMATION: Synthetic oligonucleotide

<400> SEQUENCE: 45
gaagtgcagc tggtggagtc tgggggaggc ttggtacagc ctggcaggtc cctgagactc      60
tcctgtgcag cctctggatt cacctttaat gattatgcca tgcactgggt ccggcaagct     120
ccagggaagg gcctggagtg gtctcaggt ataagttggg atagtagtag tataggctat     180
gcggactctg tgaagggccg attcaccatc tccagagaca cgccaagaa ctccctgtat     240 ctgcaaatga acagtctgag agctgaggac atggccttat attactgtgt aaaaggcaga     300
gattactatg atagtggtgg ttatttcacg gttgcttttg atatctgggg ccaagggaca     360
atggtcaccg tctcttcagc ctccaccaag ggcccacagg tgtacaccct gcccccatcc     420
cgtgacgagc tcgtcttggg gcaagtcagc ccgacctgcc tggtcaaagg cttctatccc     480

```
agcgacatcg ccgtggagtg ggagagcaat gggcagccgg agaacaacta caagaccacg    540
cctcccgtgc tggactccga cggctccttc ttcctctacg gcaagcttac cgtgcccccg    600
cggttgaagg gctggccgag gtggggctgg gggaacgtct tctcatgctc cgtgatgcat    660
gaggctctgc acaaccacta cacacagaag agcctctccc tgtctccggg taaa          714
```

<210> SEQ ID NO 46
<211> LENGTH: 217
<212> TYPE: PRT
<213> ORGANISM: Artificial sequence
<220> FEATURE:
<223> OTHER INFORMATION: Synthetic peptide

<400> SEQUENCE: 46

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Val Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Phe
                85                  90                  95

Gly Pro Gly Thr Lys Val Asp Ile Lys Arg Thr Val Ala Glu Pro Gln
            100                 105                 110

Val Tyr Thr Leu Pro Pro Ser Arg Asp Glu Leu Val Leu Gly Gln Val
        115                 120                 125

Ser Pro Thr Cys Leu Val Lys Gly Phe Tyr Pro Ser Asp Ile Ala Val
130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Gly Lys Leu Thr
                165                 170                 175

Val Pro Pro Arg Leu Lys Gly Trp Pro Arg Trp Gly Trp Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 47
<211> LENGTH: 651
<212> TYPE: DNA
<213> ORGANISM: Artificial sequence
<220> FEATURE:
<223> OTHER INFORMATION: Synthetic oligonucleotide

<400> SEQUENCE: 47

```
gacatccaga tgacccagtc tccttccacc ctgtctgcat ctgtaggaga cagagtcacc     60
atcacttgcc gggccagtca gagtattagt aggtggttgg cctggtatca gcagaaacca    120
gggaaagtcc ctaagctcct gatctataag gcatctagtt tagaaagtgg ggtcccatca    180
aggttcagcg gcagtggatc tgggacagaa ttcactctca ccatcagcag cctgcagcct    240
gatgattttg caacttatta ctgccaacag tataatagtt attctttcgg ccctgggacc    300
```

```
aaagtggata tcaaacgaac tgtggctgaa ccacaggtgt acaccctgcc cccatcccgt    360
gacgagctcg tcttggggca agtcagcccg acctgcctgg tcaaaggctt ctatcccagc    420
gacatcgccg tggagtggga gagcaatggg cagccggaga caactacaa gaccacgcct     480 cccgtgctgg actccgacgg ctccttcttc ctctacggca gcttaccgt gccccgcgg     540 ttgaagggct ggccgaggtg gggctggggg aacgtcttct catgctccgt gatgcatgag    600
gctctgcaca accactacac acagaagagc ctctccctgt ctccgggtaa a            651
```

```
<210> SEQ ID NO 48
<211> LENGTH: 129
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (38)..(42)
<223> OTHER INFORMATION: Xaa can be any naturally occurring amino acid
<220> FEATURE:
<221> NAME/KEY: misc_feature
<222> LOCATION: (95)..(98)
<223> OTHER INFORMATION: Xaa can be any naturally occurring amino acid

<400> SEQUENCE: 48

Met Lys Tyr Leu Leu Pro Thr Ala Ala Ala Gly Leu Leu Leu Leu Ala
1               5                   10                  15

Ala Gln Pro Ala Met Ala Val Ala Ala Pro Ser Val Phe Ile Phe Pro
            20                  25                  30

Pro Ser Xaa Xaa Gln Xaa Xaa Xaa Xaa Ala Ser Val Val Cys Leu
        35                  40                  45

Leu Asn Asn Phe Tyr Pro Arg Glu Ala Lys Val Gln Trp Lys Val Asp
50                  55                  60

Asn Ala Leu Gln Ser Gly Asn Ser Gln Glu Ser Val Thr Glu Gln Asp
65                  70                  75                  80

Ser Lys Asp Ser Thr Tyr Ser Leu Ser Ser Thr Leu Thr Leu Xaa Xaa
                85                  90                  95

Xaa Xaa Tyr Glu Lys His Lys Val Tyr Ala Cys Glu Val Thr His Gln
            100                 105                 110

Gly Leu Ser Ser Pro Val Thr Lys Ser Phe Asn Arg Gly Glu Ala Ala
        115                 120                 125

Ala
```

```
<210> SEQ ID NO 49
<211> LENGTH: 387
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (103)..(104)
<223> OTHER INFORMATION: n is a, c, g, or t
<220> FEATURE:
<221> NAME/KEY: misc_feature
<222> LOCATION: (106)..(107)
<223> OTHER INFORMATION: n is a, c, g, or t
<220> FEATURE:
<221> NAME/KEY: misc_feature
<222> LOCATION: (112)..(113)
```

```
<223> OTHER INFORMATION: n is a, c, g, or t
<220> FEATURE:
<221> NAME/KEY: misc_feature
<222> LOCATION: (115)..(116)
<223> OTHER INFORMATION: n is a, c, g, or t
<220> FEATURE:
<221> NAME/KEY: misc_feature
<222> LOCATION: (118)..(119)
<223> OTHER INFORMATION: n is a, c, g, or t
<220> FEATURE:
<221> NAME/KEY: misc_feature
<222> LOCATION: (121)..(122)
<223> OTHER INFORMATION: n is a, c, g, or t
<220> FEATURE:
<221> NAME/KEY: misc_feature
<222> LOCATION: (124)..(125)
<223> OTHER INFORMATION: n is a, c, g, or t
<220> FEATURE:
<221> NAME/KEY: misc_feature
<222> LOCATION: (283)..(284)
<223> OTHER INFORMATION: n is a, c, g, or t
<220> FEATURE:
<221> NAME/KEY: misc_feature
<222> LOCATION: (286)..(287)
<223> OTHER INFORMATION: n is a, c, g, or t
<220> FEATURE:
<221> NAME/KEY: misc_feature
<222> LOCATION: (289)..(290)
<223> OTHER INFORMATION: n is a, c, g, or t
<220> FEATURE:
<221> NAME/KEY: misc_feature
<222> LOCATION: (292)..(293)
<223> OTHER INFORMATION: n is a, c, g, or t

<400> SEQUENCE: 49
atgaaatacc tattgcctac ggcagccgct ggattgttat tactcgcggc ccagccggcc      60
atggccgtgg ctgcaccatc tgtcttcatc ttcccgccat ctnnsnnsca gnnsnnsnns     120
nnsnnsgcct ctgttgtgtg cctgctgaat aacttctatc ccagagaggc caaagtacag     180
tggaaggtgg ataacgccct ccaatcgggt aactcccagg agagtgtcac agagcaggac     240
agcaaggaca gcacctacag cctcagcagc accctgacgt tgnnsnnsnn snnstacgag     300
aaacacaaag tctacgcctg cgaagtcacc catcagggcc tgagctcgcc cgtcacaaag     360
agcttcaaca ggggagaggc ggccgca                                         387

<210> SEQ ID NO 50
<211> LENGTH: 132
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (38)..(42)
<223> OTHER INFORMATION: Xaa can be any naturally occurring amino acid
<220> FEATURE:
<221> NAME/KEY: misc_feature
<222> LOCATION: (95)..(101)
<223> OTHER INFORMATION: Xaa can be any naturally occurring amino acid

<400> SEQUENCE: 50

Met Lys Tyr Leu Leu Pro Thr Ala Ala Ala Gly Leu Leu Leu Leu Ala
1               5                   10                  15

Ala Gln Pro Ala Met Ala Val Ala Ala Pro Ser Val Phe Ile Phe Pro
            20                  25                  30

Pro Ser Xaa Xaa Gln Xaa Xaa Xaa Xaa Xaa Ala Ser Val Val Cys Leu
```

```
                35                  40                  45
Leu Asn Asn Phe Tyr Pro Arg Glu Ala Lys Val Gln Trp Lys Val Asp
 50                  55                  60

Asn Ala Leu Gln Ser Gly Asn Ser Gln Glu Ser Val Thr Glu Gln Asp
 65                  70                  75                  80

Ser Lys Asp Ser Thr Tyr Ser Leu Ser Ser Thr Leu Thr Leu Xaa Xaa
                 85                  90                  95

Xaa Xaa Xaa Xaa Xaa Tyr Glu Lys His Lys Val Tyr Ala Cys Glu Val
            100                 105                 110

Thr His Gln Gly Leu Ser Ser Pro Val Thr Lys Ser Phe Asn Arg Gly
        115                 120                 125

Glu Ala Ala Ala
    130

<210> SEQ ID NO 51
<211> LENGTH: 396
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (103)..(104)
<223> OTHER INFORMATION: n is a, c, g, or t
<220> FEATURE:
<221> NAME/KEY: misc_feature
<222> LOCATION: (106)..(107)
<223> OTHER INFORMATION: n is a, c, g, or t
<220> FEATURE:
<221> NAME/KEY: misc_feature
<222> LOCATION: (112)..(113)
<223> OTHER INFORMATION: n is a, c, g, or t
<220> FEATURE:
<221> NAME/KEY: misc_feature
<222> LOCATION: (115)..(116)
<223> OTHER INFORMATION: n is a, c, g, or t
<220> FEATURE:
<221> NAME/KEY: misc_feature
<222> LOCATION: (118)..(119)
<223> OTHER INFORMATION: n is a, c, g, or t
<220> FEATURE:
<221> NAME/KEY: misc_feature
<222> LOCATION: (121)..(122)
<223> OTHER INFORMATION: n is a, c, g, or t
<220> FEATURE:
<221> NAME/KEY: misc_feature
<222> LOCATION: (124)..(125)
<223> OTHER INFORMATION: n is a, c, g, or t
<220> FEATURE:
<221> NAME/KEY: misc_feature
<222> LOCATION: (283)..(284)
<223> OTHER INFORMATION: n is a, c, g, or t
<220> FEATURE:
<221> NAME/KEY: misc_feature
<222> LOCATION: (286)..(287)
<223> OTHER INFORMATION: n is a, c, g, or t
<220> FEATURE:
<221> NAME/KEY: misc_feature
<222> LOCATION: (289)..(290)
<223> OTHER INFORMATION: n is a, c, g, or t
<220> FEATURE:
<221> NAME/KEY: misc_feature
<222> LOCATION: (292)..(293)
<223> OTHER INFORMATION: n is a, c, g, or t
<220> FEATURE:
<221> NAME/KEY: misc_feature
<222> LOCATION: (295)..(296)
<223> OTHER INFORMATION: n is a, c, g, or t
<220> FEATURE:
<221> NAME/KEY: misc_feature
<222> LOCATION: (298)..(299)
<223> OTHER INFORMATION: n is a, c, g, or t
```

<220> FEATURE:
<221> NAME/KEY: misc_feature
<222> LOCATION: (301)..(302)
<223> OTHER INFORMATION: n is a, c, g, or t

<400> SEQUENCE: 51

```
atgaaatacc tattgcctac ggcagccgct ggattgttat tactcgcggc ccagccggcc      60
atggccgtgg ctgcaccatc tgtcttcatc ttcccgccat ctnnsnnsca gnnsnnsnns     120
nnsnnsgcct ctgttgtgtg cctgctgaat aacttctatc ccagagaggc caaagtacag     180
tggaaggtgg ataacgccct ccaatcgggt aactcccagg agagtgtcac agagcaggac     240
agcaaggaca gcacctacag cctcagcagc accctgacgt tgnnsnnsnn snnsnnsnns     300
nnstacgaga acacaaagt ctacgcctgc gaagtcaccc atcagggcct gagctcgccc      360
gtcacaaaga gcttcaacag gggagaggcg gccgca                                396
```

<210> SEQ ID NO 52
<211> LENGTH: 134
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (38)..(42)
<223> OTHER INFORMATION: Xaa can be any naturally occurring amino acid
<220> FEATURE:
<221> NAME/KEY: misc_feature
<222> LOCATION: (95)..(103)
<223> OTHER INFORMATION: Xaa can be any naturally occurring amino acid

<400> SEQUENCE: 52

```
Met Lys Tyr Leu Leu Pro Thr Ala Ala Ala Gly Leu Leu Leu Leu Ala
1               5                   10                  15

Ala Gln Pro Ala Met Ala Val Ala Ala Pro Ser Val Phe Ile Phe Pro
                20                  25                  30

Pro Ser Xaa Xaa Gln Xaa Xaa Xaa Xaa Xaa Ala Ser Val Val Cys Leu
            35                  40                  45

Leu Asn Asn Phe Tyr Pro Arg Glu Ala Lys Val Gln Trp Lys Val Asp
        50                  55                  60

Asn Ala Leu Gln Ser Gly Asn Ser Gln Glu Ser Val Thr Glu Gln Asp
65                  70                  75                  80

Ser Lys Asp Ser Thr Tyr Ser Leu Ser Ser Thr Leu Thr Leu Xaa Xaa
                85                  90                  95

Xaa Xaa Xaa Xaa Xaa Xaa Xaa Tyr Glu Lys His Lys Val Tyr Ala Cys
            100                 105                 110

Glu Val Thr His Gln Gly Leu Ser Ser Pro Val Thr Lys Ser Phe Asn
        115                 120                 125

Arg Gly Glu Ala Ala Ala
            130
```

<210> SEQ ID NO 53
<211> LENGTH: 402
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature

```
<222> LOCATION: (103)..(104)
<223> OTHER INFORMATION: n is a, c, g, or t
<220> FEATURE:
<221> NAME/KEY: misc_feature
<222> LOCATION: (106)..(107)
<223> OTHER INFORMATION: n is a, c, g, or t
<220> FEATURE:
<221> NAME/KEY: misc_feature
<222> LOCATION: (112)..(113)
<223> OTHER INFORMATION: n is a, c, g, or t
<220> FEATURE:
<221> NAME/KEY: misc_feature
<222> LOCATION: (115)..(116)
<223> OTHER INFORMATION: n is a, c, g, or t
<220> FEATURE:
<221> NAME/KEY: misc_feature
<222> LOCATION: (118)..(119)
<223> OTHER INFORMATION: n is a, c, g, or t
<220> FEATURE:
<221> NAME/KEY: misc_feature
<222> LOCATION: (121)..(122)
<223> OTHER INFORMATION: n is a, c, g, or t
<220> FEATURE:
<221> NAME/KEY: misc_feature
<222> LOCATION: (124)..(125)
<223> OTHER INFORMATION: n is a, c, g, or t
<220> FEATURE:
<221> NAME/KEY: misc_feature
<222> LOCATION: (283)..(284)
<223> OTHER INFORMATION: n is a, c, g, or t
<220> FEATURE:
<221> NAME/KEY: misc_feature
<222> LOCATION: (286)..(287)
<223> OTHER INFORMATION: n is a, c, g, or t
<220> FEATURE:
<221> NAME/KEY: misc_feature
<222> LOCATION: (289)..(290)
<223> OTHER INFORMATION: n is a, c, g, or t
<220> FEATURE:
<221> NAME/KEY: misc_feature
<222> LOCATION: (292)..(293)
<223> OTHER INFORMATION: n is a, c, g, or t
<220> FEATURE:
<221> NAME/KEY: misc_feature
<222> LOCATION: (295)..(296)
<223> OTHER INFORMATION: n is a, c, g, or t
<220> FEATURE:
<221> NAME/KEY: misc_feature
<222> LOCATION: (298)..(299)
<223> OTHER INFORMATION: n is a, c, g, or t
<220> FEATURE:
<221> NAME/KEY: misc_feature
<222> LOCATION: (301)..(302)
<223> OTHER INFORMATION: n is a, c, g, or t
<220> FEATURE:
<221> NAME/KEY: misc_feature
<222> LOCATION: (304)..(305)
<223> OTHER INFORMATION: n is a, c, g, or t
<220> FEATURE:
<221> NAME/KEY: misc_feature
<222> LOCATION: (307)..(308)
<223> OTHER INFORMATION: n is a, c, g, or t

<400> SEQUENCE: 53
atgaaatacc tattgcctac ggcagccgct ggattgttat tactcgcggc ccagccggcc      60
atggccgtgg ctgcaccatc tgtcttcatc ttcccgccat ctnnsnnsca gnnsnnsnns     120
nnsnnsgcct ctgttgtgtg cctgctgaat aacttctatc ccagagaggc caaagtacag     180
tggaaggtgg ataacgccct ccaatcgggt aactcccagg agagtgtcac agagcaggac     240
agcaaggaca gcacctacag cctcagcagc accctgacgt tgnnsnnsnn snnsnnsnns     300
nnsnnsnnst acgagaaaca caaagtctac gcctgcgaag tcacccatca gggcctgagc     360
tcgcccgtca caaagagctt caacagggga gaggcggccg ca                        402
```

```
<210> SEQ ID NO 54
<211> LENGTH: 127
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (38)..(45)
<223> OTHER INFORMATION: Xaa can be any naturally occurring amino acid
<220> FEATURE:
<221> NAME/KEY: misc_feature
<222> LOCATION: (95)..(101)
<223> OTHER INFORMATION: Xaa can be any naturally occurring amino acid

<400> SEQUENCE: 54

Met Lys Tyr Leu Leu Pro Thr Ala Ala Ala Gly Leu Leu Leu Leu Ala
1               5                   10                  15

Ala Gln Pro Ala Met Ala Ala Ser Thr Lys Gly Pro Ser Val Phe Pro
            20                  25                  30

Leu Ala Pro Ser Ser Xaa Xaa Xaa Xaa Xaa Xaa Xaa Ala Leu Gly
        35                  40                  45

Cys Leu Val Lys Asp Tyr Phe Pro Glu Pro Val Thr Val Ser Trp Asn
50                  55                  60

Ser Gly Ala Leu Thr Ser Gly Val His Thr Phe Pro Ala Val Leu Gln
65                  70                  75                  80

Ser Ser Gly Leu Tyr Ser Leu Ser Ser Val Val Thr Val Pro Xaa Xaa
                85                  90                  95

Xaa Xaa Xaa Xaa Xaa Thr Tyr Ile Cys Asn Val Asn His Lys Pro Ser
            100                 105                 110

Asn Thr Lys Val Asp Lys Lys Val Glu Pro Lys Ser Ala Ala Ala
        115                 120                 125

<210> SEQ ID NO 55
<211> LENGTH: 381
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (112)..(113)
<223> OTHER INFORMATION: n is a, c, g, or t
<220> FEATURE:
<221> NAME/KEY: misc_feature
<222> LOCATION: (115)..(116)
<223> OTHER INFORMATION: n is a, c, g, or t
<220> FEATURE:
<221> NAME/KEY: misc_feature
<222> LOCATION: (118)..(119)
<223> OTHER INFORMATION: n is a, c, g, or t
<220> FEATURE:
<221> NAME/KEY: misc_feature
<222> LOCATION: (121)..(122)
<223> OTHER INFORMATION: n is a, c, g, or t
<220> FEATURE:
<221> NAME/KEY: misc_feature
<222> LOCATION: (124)..(125)
<223> OTHER INFORMATION: n is a, c, g, or t
<220> FEATURE:
<221> NAME/KEY: misc_feature
<222> LOCATION: (127)..(128)
<223> OTHER INFORMATION: n is a, c, g, or t
<220> FEATURE:
<221> NAME/KEY: misc_feature
<222> LOCATION: (130)..(131)
<223> OTHER INFORMATION: n is a, c, g, or t
<220> FEATURE:
<221> NAME/KEY: misc_feature
```

<222> LOCATION: (133)..(134)
<223> OTHER INFORMATION: n is a, c, g, or t
<220> FEATURE:
<221> NAME/KEY: misc_feature
<222> LOCATION: (283)..(284)
<223> OTHER INFORMATION: n is a, c, g, or t
<220> FEATURE:
<221> NAME/KEY: misc_feature
<222> LOCATION: (286)..(287)
<223> OTHER INFORMATION: n is a, c, g, or t
<220> FEATURE:
<221> NAME/KEY: misc_feature
<222> LOCATION: (289)..(290)
<223> OTHER INFORMATION: n is a, c, g, or t
<220> FEATURE:
<221> NAME/KEY: misc_feature
<222> LOCATION: (292)..(293)
<223> OTHER INFORMATION: n is a, c, g, or t
<220> FEATURE:
<221> NAME/KEY: misc_feature
<222> LOCATION: (295)..(296)
<223> OTHER INFORMATION: n is a, c, g, or t
<220> FEATURE:
<221> NAME/KEY: misc_feature
<222> LOCATION: (298)..(299)
<223> OTHER INFORMATION: n is a, c, g, or t
<220> FEATURE:
<221> NAME/KEY: misc_feature
<222> LOCATION: (301)..(302)
<223> OTHER INFORMATION: n is a, c, g, or t

<400> SEQUENCE: 55

```
atgaaatacc tattgcctac ggcagccgct ggattgttat tactcgcggc ccagccggcc      60
atggccgcct ccaccaaggg cccatcggtc ttccccctgg cacctcctc cnnsnnsnns     120
nnsnnsnnsn nsnnsgccct gggctgcctg gtcaaggact acttccccga accggtgacg     180
gtgtcgtgga actcaggcgc cctgaccagc ggcgtgcaca ccttcccggc tgtcctacag     240
tcctcaggac tctactccct cagcagcgtg gtgaccgtgc cnnsnnsnn snnsnnsnns     300
nnsacctaca tctgcaacgt gaatcacaag cccagcaaca ccaaggtgga caagaaagtt     360
gagcccaaat ctgcggccgc a                                              381
```

<210> SEQ ID NO 56
<211> LENGTH: 87
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:

<221> NAME/KEY: misc_feature
<222> LOCATION: (70)..(71)
<223> OTHER INFORMATION: n is a, c, g, or t

<400> SEQUENCE: 56
cttaccatgg ccgtggctgc accatctgtc ttcatcttcc cgccatctnn snnscagnns    60
nnsnnsnnsn nsgcctctgt tgtgtgc    87

<210> SEQ ID NO 57
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 57
tgacaacgtc agggtgctgc tgaggc    26

<210> SEQ ID NO 58
<211> LENGTH: 41
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t

<400> SEQUENCE: 58
tcagaacgtt gnnsnnsnns nnstacgaga aacacaaagt c    41

<210> SEQ ID NO 59
<211> LENGTH: 50
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature

```
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t

<400> SEQUENCE: 59
tcagaacgtt gnnsnnsnns nnsnnsnnsn nstacgagaa acacaaagtc            50

<210> SEQ ID NO 60
<211> LENGTH: 56
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t

<400> SEQUENCE: 60
tcagaacgtt gnnsnnsnns nnsnnsnnsn nsnnsnnsta cgagaaacac aaagtc     56

<210> SEQ ID NO 61
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 61
catcgcggcc gcctctcccc tgttgaagct c                                31

<210> SEQ ID NO 62
<211> LENGTH: 99
<212> TYPE: DNA
<213> ORGANISM: Artificial sequence
<220> FEATURE:
<223> OTHER INFORMATION: Synthetic oligonucleotide
<220> FEATURE:
```

```
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (67)..(68)
<223> OTHER INFORMATION: n is a, c, g, or t
<220> FEATURE:
<221> NAME/KEY: misc_feature
<222> LOCATION: (70)..(71)
<223> OTHER INFORMATION: n is a, c, g, or t
<220> FEATURE:
<221> NAME/KEY: misc_feature
<222> LOCATION: (73)..(74)
<223> OTHER INFORMATION: n is a, c, g, or t
<220> FEATURE:
<221> NAME/KEY: misc_feature
<222> LOCATION: (76)..(77)
<223> OTHER INFORMATION: n is a, c, g, or t
<220> FEATURE:
<221> NAME/KEY: misc_feature
<222> LOCATION: (79)..(80)
<223> OTHER INFORMATION: n is a, c, g, or t

<400> SEQUENCE: 62
acgtccatgg ccgcctccac caagggccca tcggtcttcc ccctggcacc ctcctccnns    60
nnsnnsnnsn nsnnsnnsnn sgccctgggc tgcctggtc                          99

<210> SEQ ID NO 63
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 63
ggcacggtca ccacgctgct gag                                           23

<210> SEQ ID NO 64
<211> LENGTH: 61
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
```

<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t

<400> SEQUENCE: 64
agcgtggtga ccgtgcccnn snnsnnsnns nnsnnsnnsa cctacatctg caacgtgaat    60
c                                                                  61

<210> SEQ ID NO 65
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 65
catagcggcc gcagatttgg gctcaacttt cttgtc                              36

<210> SEQ ID NO 66
<211> LENGTH: 339
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (91)..(92)
<223> OTHER INFORMATION: n is a, c, g, or t
<220> FEATURE:
<221> NAME/KEY: misc_feature
<222> LOCATION: (94)..(95)
<223> OTHER INFORMATION: n is a, c, g, or t
<220> FEATURE:
<221> NAME/KEY: misc_feature
<222> LOCATION: (97)..(98)
<223> OTHER INFORMATION: n is a, c, g, or t
<220> FEATURE:
<221> NAME/KEY: misc_feature
<222> LOCATION: (100)..(101)
<223> OTHER INFORMATION: n is a, c, g, or t
<220> FEATURE:
<221> NAME/KEY: misc_feature
<222> LOCATION: (181)..(182)
<223> OTHER INFORMATION: n is a, c, g, or t
<220> FEATURE:
<221> NAME/KEY: misc_feature
<222> LOCATION: (184)..(185)
<223> OTHER INFORMATION: n is a, c, g, or t
<220> FEATURE:
<221> NAME/KEY: misc_feature
<222> LOCATION: (187)..(188)
<223> OTHER INFORMATION: n is a, c, g, or t
<220> FEATURE:
<221> NAME/KEY: misc_feature
<222> LOCATION: (190)..(191)

<223> OTHER INFORMATION: n is a, c, g, or t
<220> FEATURE:
<221> NAME/KEY: misc_feature
<222> LOCATION: (193)..(194)
<223> OTHER INFORMATION: n is a, c, g, or t
<220> FEATURE:
<221> NAME/KEY: misc_feature
<222> LOCATION: (226)..(227)
<223> OTHER INFORMATION: n is a, c, g, or t
<220> FEATURE:
<221> NAME/KEY: misc_feature
<222> LOCATION: (229)..(230)
<223> OTHER INFORMATION: n is a, c, g, or t
<220> FEATURE:
<221> NAME/KEY: misc_feature
<222> LOCATION: (232)..(233)
<223> OTHER INFORMATION: n is a, c, g, or t
<220> FEATURE:
<221> NAME/KEY: misc_feature
<222> LOCATION: (241)..(242)
<223> OTHER INFORMATION: n is a, c, g, or t
<220> FEATURE:
<221> NAME/KEY: misc_feature
<222> LOCATION: (244)..(245)
<223> OTHER INFORMATION: n is a, c, g, or t
<220> FEATURE:
<221> NAME/KEY: misc_feature
<222> LOCATION: (274)..(275)
<223> OTHER INFORMATION: n is a, c, g, or t
<220> FEATURE:
<221> NAME/KEY: misc_feature
<222> LOCATION: (277)..(278)
<223> OTHER INFORMATION: n is a, c, g, or t
<220> FEATURE:
<221> NAME/KEY: misc_feature
<222> LOCATION: (280)..(281)
<223> OTHER INFORMATION: n is a, c, g, or t

<400> SEQUENCE: 66

| | | | | | |
|---|---|---|---|---|---|
| nnscgagaac | cacaggtgta | caccctgccc | ccatcccgtg | acgagctcnn | snnsnnscaa | 60 |
| gtcagcctga | cctgcctcgt | gaaaggcttc | nnsnnsnnsn | nsatcgccgt | ggagtgggag | 120 |
| agcaatgggc | agccggagaa | caactacaag | accacgcctc | ccgttctaga | ctccgacggc | 180 |
| nnsnnsnnsn | nsnnstcctt | cttcctctac | agcaagctta | ccgtgnnsnn | snnsaggtgg | 240 |
| nnsnnsggga | acgtcttctc | atgcagtgtg | atgnnsnnsn | nsctgcacaa | ccactacaca | 300 |
| cagaagagcc | tctccctgtc | tccgggtaaa | gcggccgca | | | 339 |

<210> SEQ ID NO 67
<211> LENGTH: 339
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (91)..(92)
<223> OTHER INFORMATION: n is a, c, g, or t -continued

```
<220> FEATURE:
<221> NAME/KEY: misc_feature
<222> LOCATION: (94)..(95)
<223> OTHER INFORMATION: n is a, c, g, or t
<220> FEATURE:
<221> NAME/KEY: misc_feature
<222> LOCATION: (97)..(98)
<223> OTHER INFORMATION: n is a, c, g, or t
<220> FEATURE:
<221> NAME/KEY: misc_feature
<222> LOCATION: (100)..(101)
<223> OTHER INFORMATION: n is a, c, g, or t
<220> FEATURE:
<221> NAME/KEY: misc_feature
<222> LOCATION: (181)..(182)
<223> OTHER INFORMATION: n is a, c, g, or t
<220> FEATURE:
<221> NAME/KEY: misc_feature
<222> LOCATION: (184)..(185)
<223> OTHER INFORMATION: n is a, c, g, or t
<220> FEATURE:
<221> NAME/KEY: misc_feature
<222> LOCATION: (187)..(188)
<223> OTHER INFORMATION: n is a, c, g, or t
<220> FEATURE:
<221> NAME/KEY: misc_feature
<222> LOCATION: (190)..(191)
<223> OTHER INFORMATION: n is a, c, g, or t
<220> FEATURE:
<221> NAME/KEY: misc_feature
<222> LOCATION: (193)..(194)
<223> OTHER INFORMATION: n is a, c, g, or t
<220> FEATURE:
<221> NAME/KEY: misc_feature
<222> LOCATION: (226)..(227)
<223> OTHER INFORMATION: n is a, c, g, or t
<220> FEATURE:
<221> NAME/KEY: misc_feature
<222> LOCATION: (229)..(230)
<223> OTHER INFORMATION: n is a, c, g, or t
<220> FEATURE:
<221> NAME/KEY: misc_feature
<222> LOCATION: (232)..(233)
<223> OTHER INFORMATION: n is a, c, g, or t
<220> FEATURE:
<221> NAME/KEY: misc_feature
<222> LOCATION: (241)..(242)
<223> OTHER INFORMATION: n is a, c, g, or t
<220> FEATURE:
<221> NAME/KEY: misc_feature
<222> LOCATION: (244)..(245)
<223> OTHER INFORMATION: n is a, c, g, or t
<220> FEATURE:
<221> NAME/KEY: misc_feature
<222> LOCATION: (274)..(275)
<223> OTHER INFORMATION: n is a, c, g, or t
<220> FEATURE:
<221> NAME/KEY: misc_feature
<222> LOCATION: (277)..(278)
<223> OTHER INFORMATION: n is a, c, g, or t
<220> FEATURE:
<221> NAME/KEY: misc_feature
<222> LOCATION: (280)..(281)
<223> OTHER INFORMATION: n is a, c, g, or t

<400> SEQUENCE: 67
nnsgctcttg gtgtccacat gtgggacggg ggtagggcac tgctcgagnn snnsnnsgtt      60
cagtcggact ggacggagca ctttccgaag nnsnnsnnsn nstagcggca cctcaccctc     120
tcgttacccg tcggcctctt gttgatgttc tggtgcggag ggcaagatct gaggctgccg     180
nnsnnsnnsn nsnnsaggaa gaaggagatg tcgttcgaat ggcacnnsnn snnstccacc     240 nnsnnscccct tgcagaagag tacgtcacac tacnnsnnsn nsgacgtgtt ggtgatgtgt    300
gtcttctcgg agagggacag aggcccattt cgccggcgt                           339
```